United States Patent
Hill et al.

(10) Patent No.: US 11,662,343 B2
(45) Date of Patent: May 30, 2023

(54) CELLULAR POPULATIONS AND USES THEREOF

(71) Applicant: The Council of the Queensland Institute of Medical Research, Herston (AU)

(72) Inventors: Geoffrey R. Hill, Herston (AU); Ping Zhang, Herston (AU)

(73) Assignee: THE COUNCIL OF THE QUEENSLAND INSTITUTE OF MEDICAL RESEARCH, Herston (AU)

( * ) Notice: Subject to any disclaimer, the term of this patent is extended or adjusted under 35 U.S.C. 154(b) by 638 days.

(21) Appl. No.: 16/603,454

(22) PCT Filed: Apr. 9, 2018

(86) PCT No.: PCT/AU2018/050322
§ 371 (c)(1),
(2) Date: Oct. 7, 2019

(87) PCT Pub. No.: WO2018/184075
PCT Pub. Date: Oct. 11, 2018

(65) Prior Publication Data
US 2020/0150108 A1    May 14, 2020

(30) Foreign Application Priority Data

Apr. 7, 2017  (AU) .................................. 2017901292

(51) Int. Cl.
*G01N 33/50* (2006.01)
*C07K 14/535* (2006.01)
*C07K 14/54* (2006.01)
*C07K 14/73* (2006.01)
*C12N 5/0783* (2010.01)

(52) U.S. Cl.
CPC ......... *G01N 33/505* (2013.01); *C07K 14/535* (2013.01); *C07K 14/5412* (2013.01); *C07K 14/5428* (2013.01); *C07K 14/5446* (2013.01); *C07K 14/70514* (2013.01); *C12N 5/0637* (2013.01)

(58) Field of Classification Search
None
See application file for complete search history.

(56) References Cited

FOREIGN PATENT DOCUMENTS

WO    WO 2013/192215    12/2013

OTHER PUBLICATIONS

Ghosh et al., LPS Stimulates and Hsp70 Down-Regulates TLR4 to Orchestrate Differential Cytokine Response of Culture-Differentiated Innate Memory CD8(+) T Cells. Cytokine. May 2015;73(1):44-52.
Kara et al., CCR2 Defines in Vivo Development and Homing of IL-23-driven GM-CSF-producing Th17 Cells. Nat Commun. Oct. 29, 2015;6:8644.
Lupar et al., Eomesodermin Expression in CD4+ T Cells Restricts Peripheral Foxp3 Induction. J Immunol. Nov. 15, 2015;195(10):4742-52.
Qui et al., CD134 Plus CD137 Dual Costimulation Induces Eomesodermin in CD4 T Cells to Program Cytotoxic Th1 Differentiation. J Immunol. Oct. 1, 2011;187(7):3555-64.
Shashkova et al., Osteoclast-Primed Foxp3+ CD8 T Cells Induce T-bet, Eomesodermin, and IFN-γ To Regulate Bone Resorption. J Immunol. Aug. 1, 2016;197(3):726-35.
Zhang et al., Eomesodermin Promotes the Development of Type 1 Regulatory T (T R 1) Cells. Sci Immunol. Apr. 7, 2017;2(10):eaah7152.
Zhou et al., The IL-10 and IFN-gamma Pathways Are Essential to the Potent Immunosuppressive Activity of Cultured CD8+ NKT-like Cells. Genome Biol. 2008;9(7):R119.
International Search Report for PCT/AU2018/050322, dated Jun. 20, 2018, 5 pages.

*Primary Examiner* — Amy E Juedes
(74) *Attorney, Agent, or Firm* — Casimir Jones, S.C.; Mary Ann D. Brow

(57) ABSTRACT

Disclosed are methods of identifying immunosuppressive $T_R1$ regulatory T cells, including in methods of diagnosing the presence of immune tolerance, methods of producing immunosuppressive regulatory T cells, and methods of eliciting immune tolerance in a subject. These methods include screening T cells to detect Eomes$^+$IL-10$^+$ T cells or expressing recombinant Eomes in T cell populations to generate immunosuppressive regulatory T cells.

13 Claims, 64 Drawing Sheets

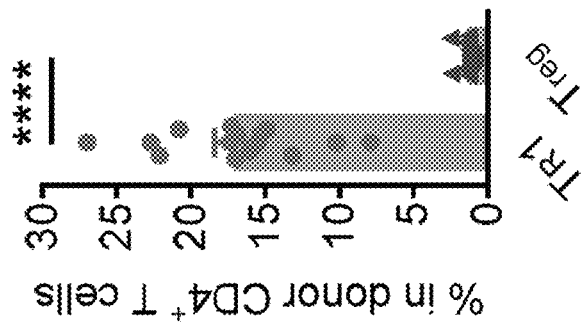
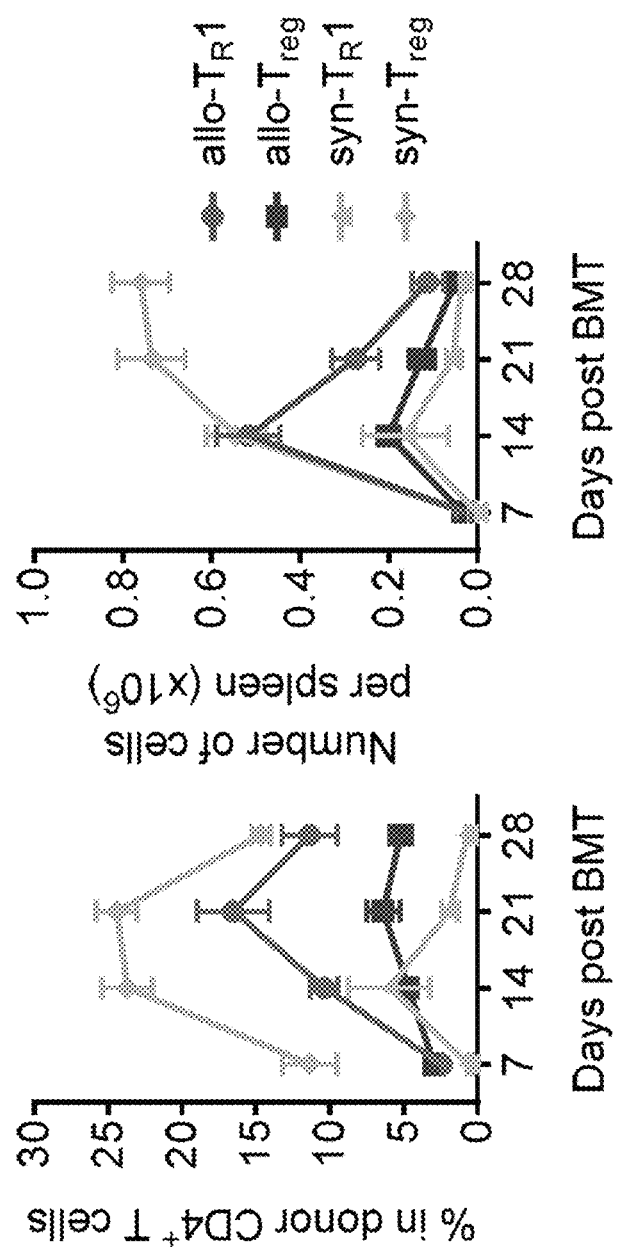
FIG. 1F
FIG. 1E

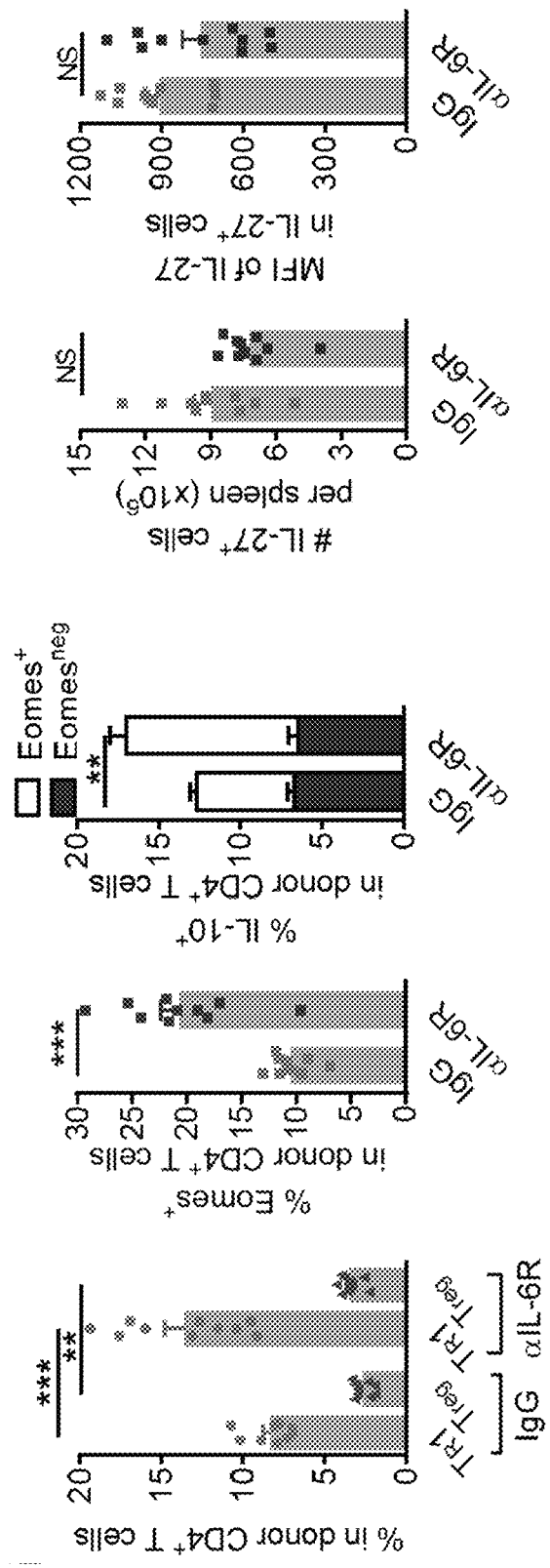

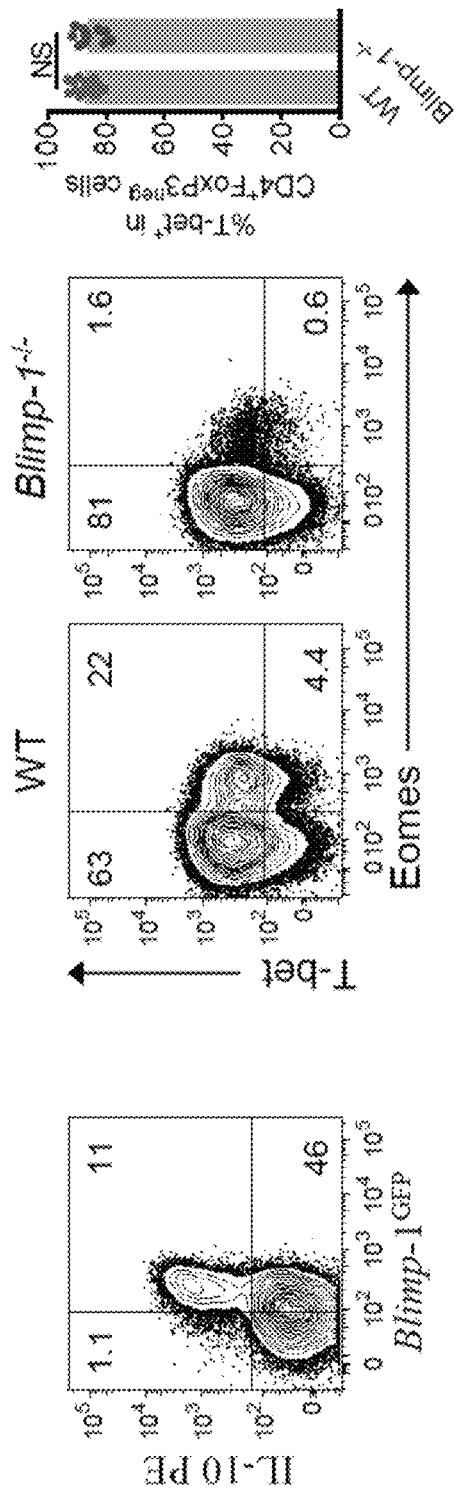
FIG. 14A
FIG. 14B
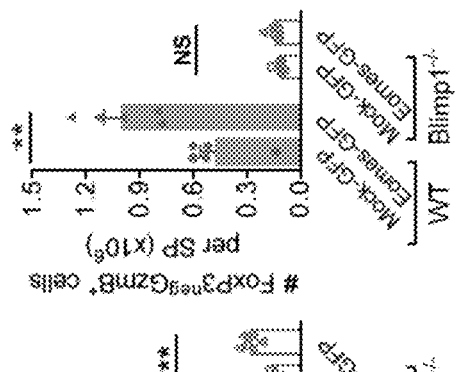
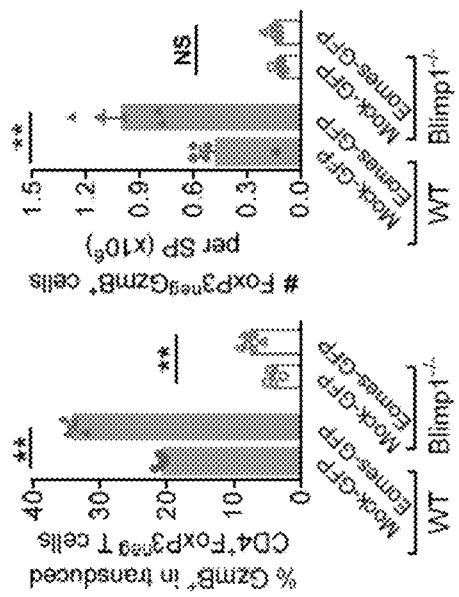
FIG. 14C

CELLULAR POPULATIONS AND USES THEREOF

FIELD OF THE INVENTION

This application claims priority to Australian Provisional Application No. 2017901292 entitled "Cellular populations and uses therefor" filed 7 Apr. 2017, the contents of which are incorporated herein by reference in their entirety.

This invention relates generally to methods of identifying immunosuppressive $T_R1$ regulatory T cells, including in methods of diagnosing the presence of immune tolerance, methods of producing immunosuppressive regulatory T cells, and methods of eliciting immune tolerance in a subject.

Bibliographic details of certain publications numerically referred to in this specification are collected at the end of the description.

BACKGROUND OF THE INVENTION

Type-1 regulatory T ($T_R1$) cells are a FoxP3 negative, IL-10 producing T cell population, which have potent immune suppressive functions and bear alloantigen specificity (1, 2). IL-10 is the major mediator by which $T_R1$ cells assert their immunomodulatory role. Direct and bystander-mediated T cell suppression by TGFβ and granzyme B-dependent killing of antigen presenting cells (APC) have also been described (reviewed in (3)). In addition to IL-10, $T_R1$ cells show high expression of TGF-β, secrete intermediate amounts of IFNγ but no IL-2 or IL-4 (3-5). Extensive studies have demonstrated the importance of $T_R1$ cells in maintaining immune tolerance or limiting overt inflammation after transplantation, during autoimmune disease or after infections (6-9). IL-27 has been identified as a main driver of $T_R1$ cell differentiation via the activation of transcription factors that include B-lymphocyte-induced maturation protein-1 (Blimp-1), the aryl hydrocarbon receptor (AhR) and c-Maf (5-8, 10-12). However, the function, phenotype and lineage development of $T_R1$ cells in disease states remains poorly understood (5, 13).

Graft-versus-host disease (GVHD) is a common complication of allogeneic bone marrow transplantation (BMT), limiting survival and quality of life (14). $CD4^+FoxP3^+$ regulatory T ($T_{reg}$) cells are a well defined regulatory population important for the generation of tolerance after BMT (15). Due to impaired homeostasis of $T_{reg}$ cells after allogenenic BMT (16), other suppressive cell populations such as $T_R1$ cells may be imperative for the prevention and treatment of GVHD. Consistent with this idea, IL-10 deficiency in donor T cells results in more severe GVHD (17, 18).

SUMMARY OF THE INVENTION

In work leading up to the present invention, a mouse model was developed using a dual $Il10^{GFP}$/Fox3$^{RFP}$ reporter mouse strain (19, 20) to delineate regulatory T cell responses after experimental BMT. Using GVHD as a disease model, it was found that $T_R1$ cells are the most abundant IL-10 producing regulatory T cell population after experimental BMT. Further analyses demonstrated unexpectedly that $T_R1$ cells that develop during GVHD express high amounts of Eomes, which is required for their development and that over-expression of Eomes promotes $T_R1$ cell development both in vivo and in vitro. Eomes acts in concert with Blimp-1, a known transcriptional regulator of $T_R1$ cell differentiation (6-8, 21), to induce IL-10 expression. The present inventors also found that Eomes expression and $T_R1$ cell development require T-bet and donor macrophage-derived IL-27, resulting in a T-bet$^{lo}$Eomes$^{hi}$ phenotype. Additionally, it was found that Eomes$^+$ $T_R1$ cells are abundant after clinical BMT. These findings permit the development of new therapeutic strategies in detecting immunosuppressive $T_R1$ cells, including the presence of immune response that is anergic or tolergenic, and in eliciting immune tolerance, as described hereafter.

Accordingly, in one aspect, the present invention provides methods of identifying immunosuppressive T cells (e.g., $T_R1$ regulatory T cells) in a sample. These methods generally comprise: screening T cells in the sample to detect Eomes$^+$IL-10$^+$ T cells; and identifying the detected T-cells as immunosuppressive (e.g., $T_R1$) regulatory T cells. Suitably the methods further comprise isolating the identified immunosuppressive regulatory T-cells. In some embodiments, the screening step is further characterized by detection of Eomes$^{hi}$ T cells, IL-10$^{hi}$ T cells or Eomes$^{hi}$IL-10$^{hi}$ T cells. In some of the same and other embodiments, the screening step is further characterized by detection of T-bet$^{lo}$Eomes$^+$IL-10$^+$ T cells. In some of the same and other embodiments, the screening step is further characterized by detection of Eomes$^+$IL-10$^+$ T cells that are positive or high for IFNγ. In some of the same and other embodiments, the screening step is further characterized by detection of Eomes$^+$IL-10$^+$ T cells that are positive for at least one (e.g., 1, 2, 3, 4, 5, 6) of CD4, CD122, α4β7, LAG-3, Ly6C and TIGIT, and/or negative or low for one or more (e.g., 1, 2, 3) of CD25, CD69 and FoxP3. In some of the same and other embodiments, the screening step is further characterized by detection of Eomes$^+$IL-10$^+$CD4$^+$ T cells. In some of the same and other embodiments, the screening step is further characterized by detection of Eomes$^+$IL-10$^+$ T cells, suitably Eomes$^+$IL-10$^+$CD4$^+$ T cells, that are negative or low for $T_H2$ cytokines such as IL-4, IL-13 and IL-5, and/or for $T_H17$ cytokines such as IL-17, IL-6 and GM-CSF. Suitably, the screening methods further comprise detecting suppression by the Eomes$^+$IL-10$^+$ T cells of at least one immune function selected from the group consisting of IL-2 production, cell proliferation, cytokine production, cell migration, and effector functions, killing, and T-cell proliferation. The sample may be a peripheral blood mononuclear cell (PBMC) sample or a lymphoid tissue sample.

In a related aspect, the present invention provides methods of diagnosing the presence of immune tolerance in a subject. These methods generally comprise detecting the presence in the subject of Eomes$^+$IL-10$^+$ T cells, suitably Eomes$^+$IL-10$^+$CD4$^+$ T cells, as broadly described above and elsewhere herein to thereby diagnose the presence of immune tolerance in the subject. Suitably, the methods comprise detecting the presence of Eomes$^+$IL-10$^+$ T cells in a sample obtained from the subject. In specific embodiments, the immune tolerance is an antigen-specific immune tolerance. In illustrative examples of this type, the antigen is associated with a disease or disorder such as but not limited to an inflammatory disorder, a cancer, an autoimmune disorder (e.g., type 1 diabetes, rheumatoid arthritis, Systemic Lupus Erythematosus (SLE), multiple sclerosis, or myasthenia gravis), a graft vs. host disease, an organ transplantation rejection, an allergy, allergic rhinitis, a food allergy or asthma.

Another aspect of the present invention provides methods of producing an isolated population of immunosuppressive regulatory (e.g., $T_R1$) T cells. These methods generally comprise: isolating a heterogenous population of cells (e.g., PBMC) comprising regulatory T cells; optionally enriching for T cells that are positive or high for at least one (e.g., 1, 2, 3, 4, 5, 6) of CD4, CD122, α4β7, LAG-3, Ly6C and TIGIT, and/or negative or low for one or more (e.g., 1, 2, 3) of CD25, CD69 and FoxP3; and expressing Eomes in the T cells to thereby make an isolated population of immunosuppressive regulatory T cells. In specific embodiments, the methods comprise isolating and/or enriching for T cells that are positive CD4 and that express Eomes. In representative examples of this type, the methods comprise isolating and/or enriching for T cells that are also positive for at least one (e.g., 1, 2, 3, 4, 5) of CD122, α4β7, LAG-3, Ly6C and TIGIT, and/or negative or low for at least one (e.g., 1, 2, 3) of CD25, CD69 and FoxP3. Suitably, these methods further comprise isolating Eomes$^+$IL-10$^+$ T cells, suitably Eomes$^+$IL-10$^+$CD4$^+$ T cells, from the heterogenous population or enriched T cell population. In specific embodiments, the production methods comprise introducing into the T cells a construct that comprises an Eomes coding sequence in operable connection with a regulatory sequence that is operable in the T cells. In some of the same and other embodiments, the production methods further comprise expanding the population, for example, by contacting the isolated T cells of the population with antigen or alloantigen, and/or anti-CD3/anti-CD28 antibodies plus IL-2 in the presence of TGFβ and/or IL-27. In representative examples of this type, the Eomes$^+$IL-10$^+$ T cells are antigen-specific immunoregulatory T cells.

In a related aspect, the present invention provides methods of producing an immunosuppressive regulatory (e.g., $T_R1$) T cell. These methods generally comprise, consist or consist essentially of: expressing in a T cell that is positive or high for at least one (e.g., 1, 2, 3, 4, 5, 6) of CD4, CD122, α4β7, LAG-3, Ly6C and TIGIT, and/or negative or low for one or more (e.g., 1, 2, 3) of CD25, CD69 and FoxP3, a recombinant Eomes coding sequence to thereby produce an immunosuppressive regulatory (e.g., $T_R1$) T cell. Suitably, the T cell is positive or high for CD4. Suitably, the immunosuppressive regulatory T cell is an IL-10$^+$CD4$^+$ T cell. In some embodiments, the immunosuppressive regulatory T cell is an Eomes$^{hi}$ T cell. In some of the same and other embodiments, the immunosuppressive regulatory T cell is a T-bet$^{lo}$T cell. In some of the same and other embodiments, the immunosuppressive regulatory T cell is an IFNγ$^+$ T cell. In representative examples, the immunosuppressive regulatory T cell is high for one or both of IL-10 and IFNγ. In some of the same and other embodiments, the immunosuppressive regulatory T cell is negative or low for any one or more $T_H2$ cytokines such as IL-4, IL-13 and IL-5, and/or any one or more $T_H17$ cytokines such as IL-17, IL-6 and GM-CSF. Suitably, the immunosuppressive regulatory T cell is capable of suppressing at least one immune function selected from the group consisting of IL-2 production, cell proliferation, cytokine production, cell migration, and effector functions, killing, and T-cell proliferation. In specific embodiments, the production methods further comprise introducing into the T cell a construct that comprises an Eomes coding sequence in operable connection with a regulatory sequence that is operable in the T cell. In some of the same and other embodiments, the production methods comprise expressing the recombinant Eomes coding sequence in the absence of contacting the T cell with IL-27 (e.g., in the absence of culturing the T cell with exogenous IL-27 or with an IL-27-producing cell such as an IL-27-producing antigen-presenting cell (e.g., an IL-27-producing DC or monocytes)). In specific embodiments, the methods further comprise contacting the T cell with an antigen or alloantigen. In some of the same and other embodiments, the methods further comprise contacting the T cell with one or both of an anti-CD3 antibody and an anti-CD28 antibody.

In another related aspect, the present invention provides an immunosuppressive regulatory (e.g., $T_R1$) T cell comprising, consisting or consisting essentially of a construct that comprises an Eomes coding sequence in operable connection with a regulatory sequence that is operable in the T cell. Suitably the immunosuppressive regulatory T cell is an IL-10$^+$CD4$^+$ T cell. In some embodiments, the T cell is an Eomes$^{hi}$ T cell. In some of the same and other embodiments, the T cell is a T-bet$^{lo}$ T cell. In some of the same and other embodiments, the T cell is an IFNγ$^+$ T cell. In representative examples, the T cell is high for one or both of IL-10 and IFNγ. In some of the same and other embodiments, the T cell is negative or low for any one or more $T_H2$ cytokines such as IL-4, IL-13 and IL-5, and/or any one or more $T_H17$ cytokines such as IL-17, IL-6 and GM-CSF. Suitably, the immunosuppressive regulatory T cell is capable of suppressing at least one immune function selected from the group consisting of IL-2 production, cell proliferation, cytokine production, cell migration, and effector functions, killing, and T-cell proliferation.

In yet another aspect, methods are provided for eliciting immune tolerance in a subject (e.g., a mammal including a primate such as a human). These methods generally comprise administering to the subject a population of immunoregulatory (e.g., $T_R1$) T cells comprising Eomes$^+$IL-10$^+$ T cells to thereby elicit immune tolerance in the subject. Suitably the Eomes$^+$IL-10$^+$ T cells comprise Eomes$^+$IL-10$^+$CD4$^+$ T cells. In some embodiments, the Eomes$^+$IL-10$^+$ T cells comprise Eomes$^{hi}$ T cells. In some of the same and other embodiments, the Eomes$^+$IL-10$^+$ T cells comprise T-bet$^{lo}$ T cells. In some of the same and other embodiments, the Eomes$^+$IL-10$^+$ T cells comprise IFNγ$^+$ T cells. In representative examples, the Eomes$^+$IL-10$^+$ T cells are high for one or both of IL-10 and IFNγ. In some of the same and other embodiments, the Eomes$^+$IL-10$^+$ T cells are negative or low for $T_H2$ cytokines such as IL-4, IL-13 and IL-5, and/or $T_H17$ cytokines such as IL-17, IL-6 and GM-CSF. Suitably, the immunosuppressive regulatory (e.g., $T_R1$) T cells are capable of suppressing at least one immune function selected from the group consisting of IL-2 production, cell proliferation, cytokine production, cell migration, and effector functions, killing, and T-cell proliferation.

In specific embodiments, the Eomes$^+$IL-10$^+$ T cells, which suitably comprise Eomes$^+$IL-10$^+$CD4$^+$ T cells, contain a construct comprising an Eomes coding sequence that is operably connected to a regulatory sequence that is operable in the Eomes$^+$IL-10$^+$ T cells. In related embodiments, the immune tolerance elicitation methods further comprise introducing the construct into the Eomes$^+$IL-10$^+$ T cells.

Suitably, the population of immunoregulatory $T_R1$) T cells is enriched for Eomes$^+$IL-10$^+$ T cells, suitably Eomes$^+$IL-10$^+$CD4$^+$ T cells. In related embodiments, the immune tolerance elicitation methods further comprise isolating a heterogenous population of cells (e.g., PBMC) and enriching for T cells that are positive or high for at least one (e.g., 1, 2, 3, 4, 5, 6) of CD4, CD122, α4β7, LAG-3, Ly6C and TIGIT, and/or negative or low for one or more (e.g., 1, 2, 3) of CD25, CD69 and FoxP3. In specific embodiments, the methods comprise isolating and/or enriching for T cells that are positive CD4 and that express Eomes. In representative examples of this type, the methods comprise isolating and/or enriching for T cells that are also positive for at least one (e.g., 1, 2, 3, 4, 5) of CD122, α4β7, LAG-3, Ly6C and TIGIT, and/or negative or low for at least one (e.g., 1, 2, 3) of CD25, CD69 and FoxP3.

The population of immunoregulatory (e.g., $T_R1$) T cells (e.g., an isolated heterogeneous population or enriched population as described for example above) may be expanded to provide an expanded population of immunoregulatory (e.g., $T_R1$) T cells. Thus, in related embodiments, the immune tolerance elicitation methods further comprise expanding the population, for example, by contacting the isolated T cells of the population with antigen or alloantigen, and/or anti-CD3/anti-CD28 antibodies plus IL-2 in the presence of TGFβ and/or IL-27. In representative examples of this type, the Eomes$^+$IL-10$^+$ T cells, suitably Eomes$^+$IL-10$^+$CD4$^+$ T cells, are antigen-specific immunoregulatory T cells.

The Eomes$^+$IL-10$^+$ T cells, suitably Eomes$^+$IL-10$^+$CD4$^+$ T cells, may be autologous or allogeneic to the subject.

Suitably, the subject has an immune or autoimmune disorder (e.g., type 1 diabetes, rheumatoid arthritis, Systemic Lupus Erythematosus (SLE), multiple sclerosis, or myasthenia gravis) and is in need of immunosuppression. In some embodiments, the immune disorder is selected from the group consisting of graft vs. host disease, an organ transplantation rejection, and allergy. In other embodiments, the immune disorder is allergic rhinitis, a food allergy, or asthma.

In specific embodiments, the subject is a recipient of a transplant. The transplant may be recipient autologous) or donor-derived (allogeneic or xenogeneic). In specific embodiments, the transplant is a bone marrow transplant. Suitably, the immune system of the subject is not systemically suppressed. In representative examples of the type, the immunoregulatory T cells are administered concurrently with exposure of the subject to the transplant. In some embodiments, the immunoregulatory T cells are administered simultaneously with exposure of the subject to the transplant. In other embodiments, the immunoregulatory T cells are administered before transplant exposure (e.g., within 1, 2, 3, 4, 5, 6, 7 days) or after transplant exposure (e.g., after 1, 2, 3, 4, 5, 6, 7 days).

In a related aspect, the present invention provides methods for attenuating or inhibiting the development of graft-versus-host disease (GVHD) in a subject receiving a graft. These methods generally comprise administering to the subject a population of immunoregulatory (e.g., $T_R1$) T cells comprising Eomes$^+$IL-10$^+$ T cells, to thereby attenuate or inhibit the development of GVHD in the subject.

Figure 15:
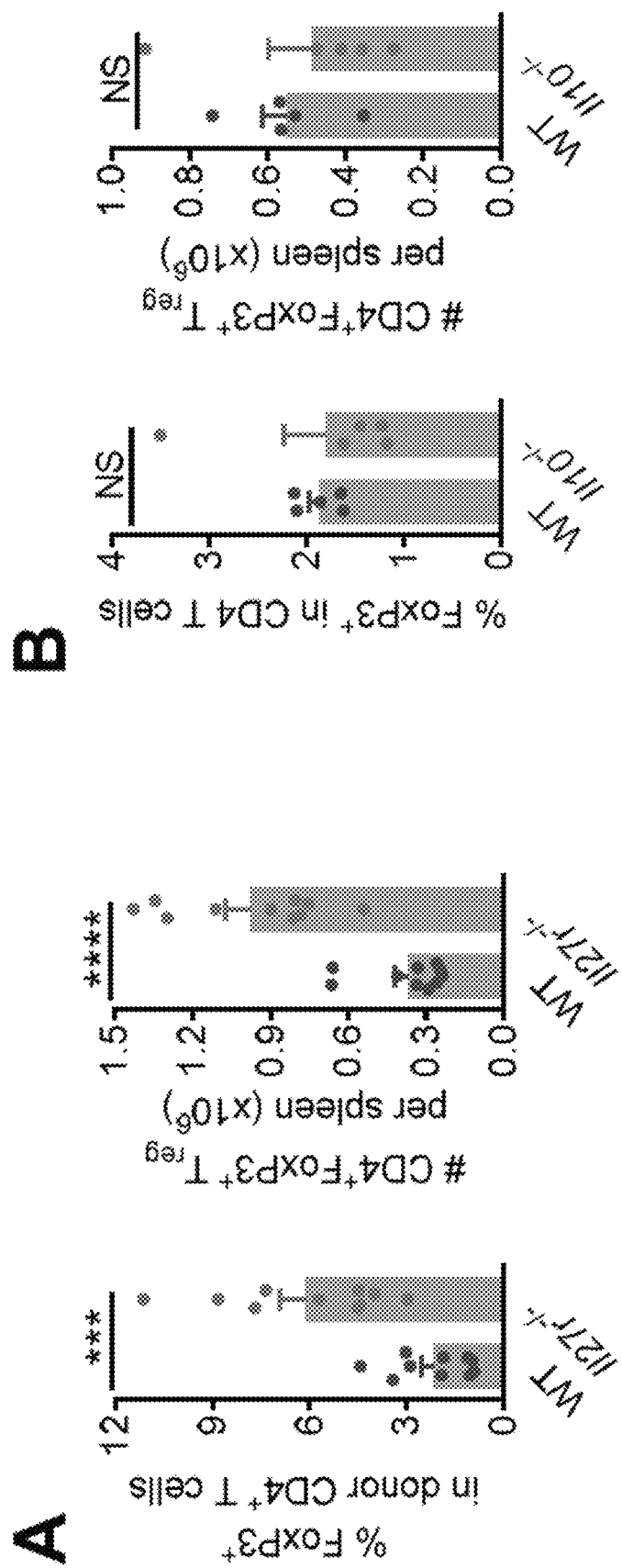

FIG. 15 is a graphical representation showing $T_{reg}$ development in Il27r−/− and Il10−/− cells after BMT. B6D2F1 recipients were transplanted with WT or gene deficient CD4+ T cells and spleens taken at d14. (A) Frequencies and number of $T_{reg}$ cells in recipients of WT or Il27r−/−CD4+ T cells (n=10 per group). (8) Frequencies and number of $T_{reg}$ cells in recipients of WT or Il10−/− CD4+CD25$^{neg}$ T cells (n=5 per group).

FIG. 16 is a graphical representation showing that both T-bet and Eomes are required for $T_R1$ cell generation. (A-D) B6.WT or Tbx21−/− CD4+ T cells were transplanted into B6D2F1 mice and spleen examined at d12. (A) Number of donor CD4+ T cells and IFNγ+IL-10+ $T_R1$ cells. (8) Expression of IL-4, IL-17A, IL-10 and IFNγ in CD4+ T cells (n=10 per group). (C) Gene expression profile of WT or Tbx21−/− CD4+ T cells 012 after BMT (n=4 per group, representative of 2 independent experiments). (D) Expression of IFNγ and Eomes in donor CD4+ T cells and of IL-4 and Eomes in CD4+ IL-10+ cells (representative of 4 experiments). (E and F) B6D2F1 mice were transplanted with retrovirally (Mock-GFP and Eomes-GFP) transduced B6.WT or Tbx21−/−CD4+ T cells and spleen examined at d7. (E) Expression of IFNγ and Eomes in donor CD4+ T cells and (f) frequencies and numbers of CD4+IL-17A T cells. (G) B6 CD4+ T cells were transplanted into B6D2F1 recipients and spleens examined. Expression of Eomes in $T_R1$, $T_{reg}$ and $T_{con}$ cells over time (n=7-8 each time-point). (H) B6 Foxp3$^{RFP}$/Il10$^{GFP}$ CD4+ T cells were transplanted into B6D2F1 recipients. Donor CD4+ T cells (2×10$^6$) were FACS purified from spleens (B6D2F1) d14 days after primary transplant and transplanted into secondary B6D2F1 recipients. Expression of T-bet, Eomes and $T_R1$ cells in CD4+ T cells at 4 weeks after transfer into secondary BMT recipients are shown (representative 2 experiments). (1) Expression of T-bet and Eomes in retrovirally transduced CD4+ T cells d7-10 after BMT (representative >3 experiments). Data represents mean±S.E.M.

Figure 17:
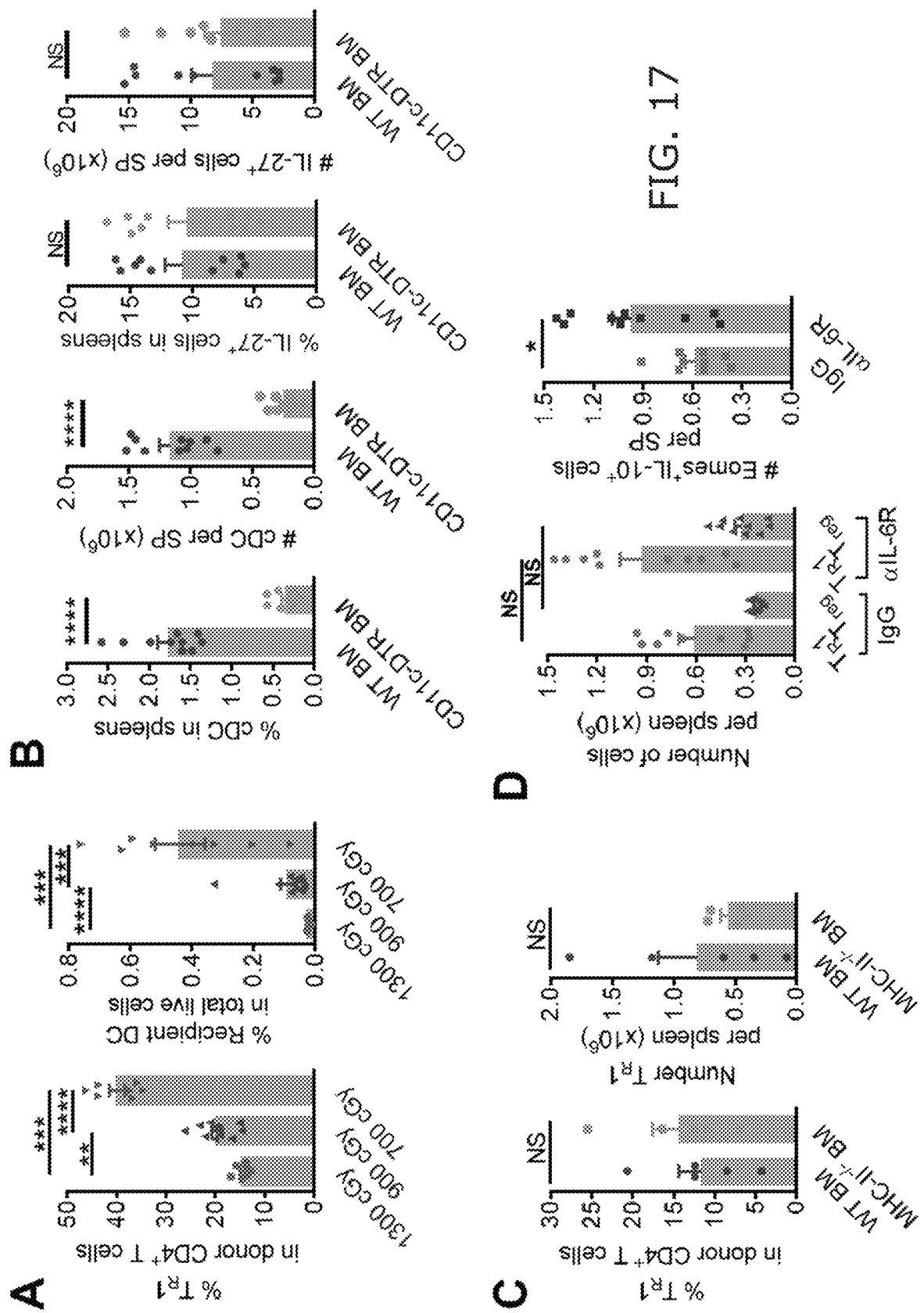

FIG. 17 is a graphical representation showing that recipient DC and donor IL-27 promote $T_R1$ cell development after experimental BMT. (A-D) B6D2F1 mice were transplanted with TCD BM and WT or gene deficient CD4+ T cells and spleen examined. (A) B6 Il10$^{GFP}$ Foxp3$^{RFP}$ CD4+ T were transplanted into differentially irradiated (1300, 900 or 700 cGy) B6D2F1 mice and frequencies of $T_R1$ cells and recipient DC in spleen determined at d14 (n=7, 11 and 8 respectively). (8) Recipients were transplanted with WT or CD11c-DOG BM and treated with DT after BMT to deplete donor cDC. Expression of cDC and IL-27 in the spleen at d10 is shown (n=10 per group). (C) B6 Il10$^{GFP}$ Foxp3$^{RFP}$ CD4+ T and B6.WT or MHC-II−/− BM were transplanted into WT B6D2F1 mice and expression of $T_R1$ cells determined in spleen at d14 (n=5 per group). (D) Recipients were treated with IL-6R and spleens taken for analysis at d10. Number of Foxp3$^{RFPneg}$ Il10$^{GFP+}$ $T_R1$, Foxp3$^{RFP}$ $T_{reg}$ and Eomes+IL-10+ cells (n=9-10 per group). Data represents mean±S.E.M.

Figure 18:
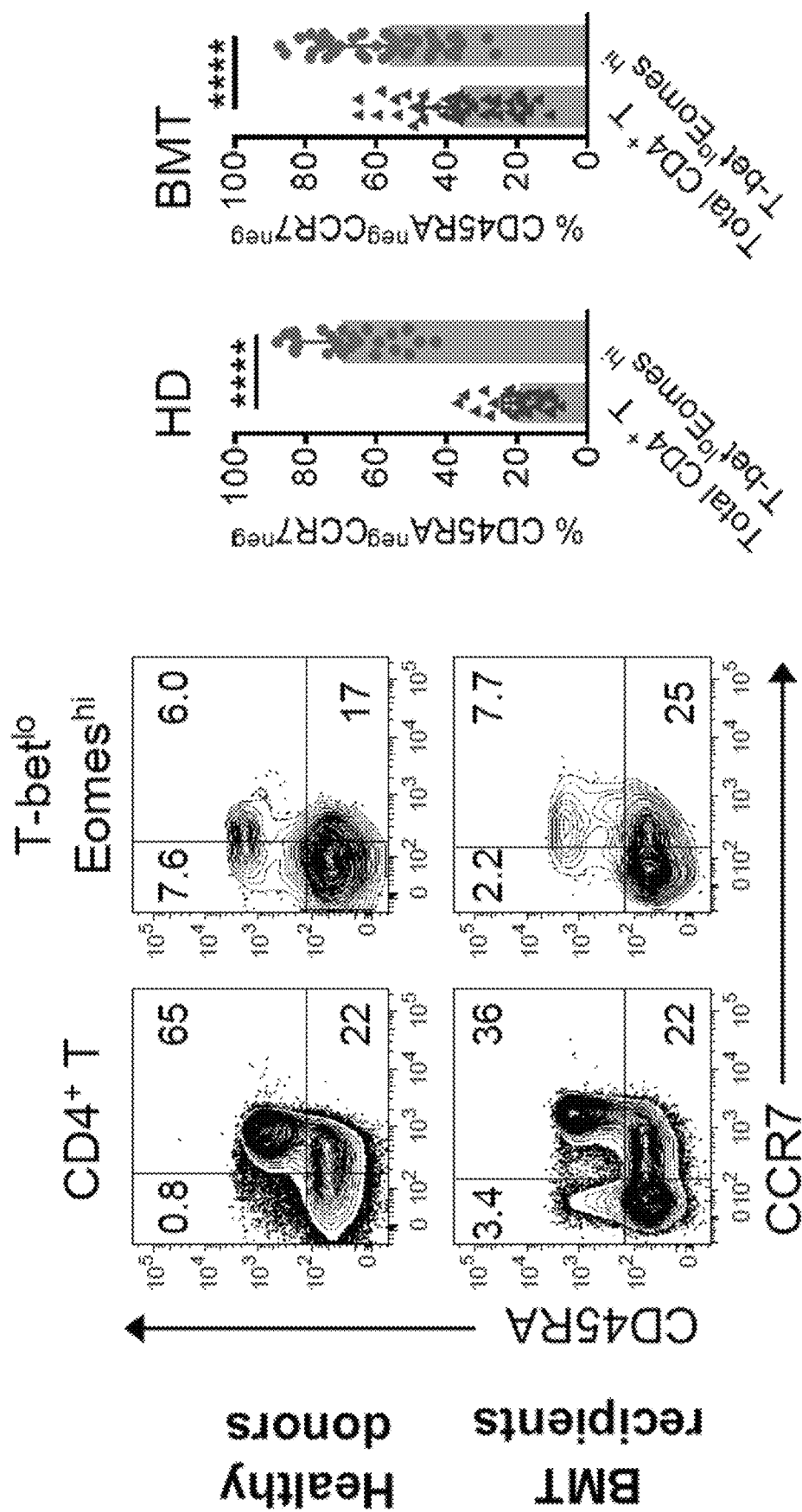

FIG. 18 is a graphical representation showing that Eomes and T-bet can be used to identify $T_R1$ cells in humans. Expression of memory markers in the T-bet$^{lo}$Eomes$^{hi}$ population relative to total CD4+ T cells in healthy individuals (n=27) or at d60 after clinical BMT (n=43). Data represents median±interquartile range.

Figure 19:
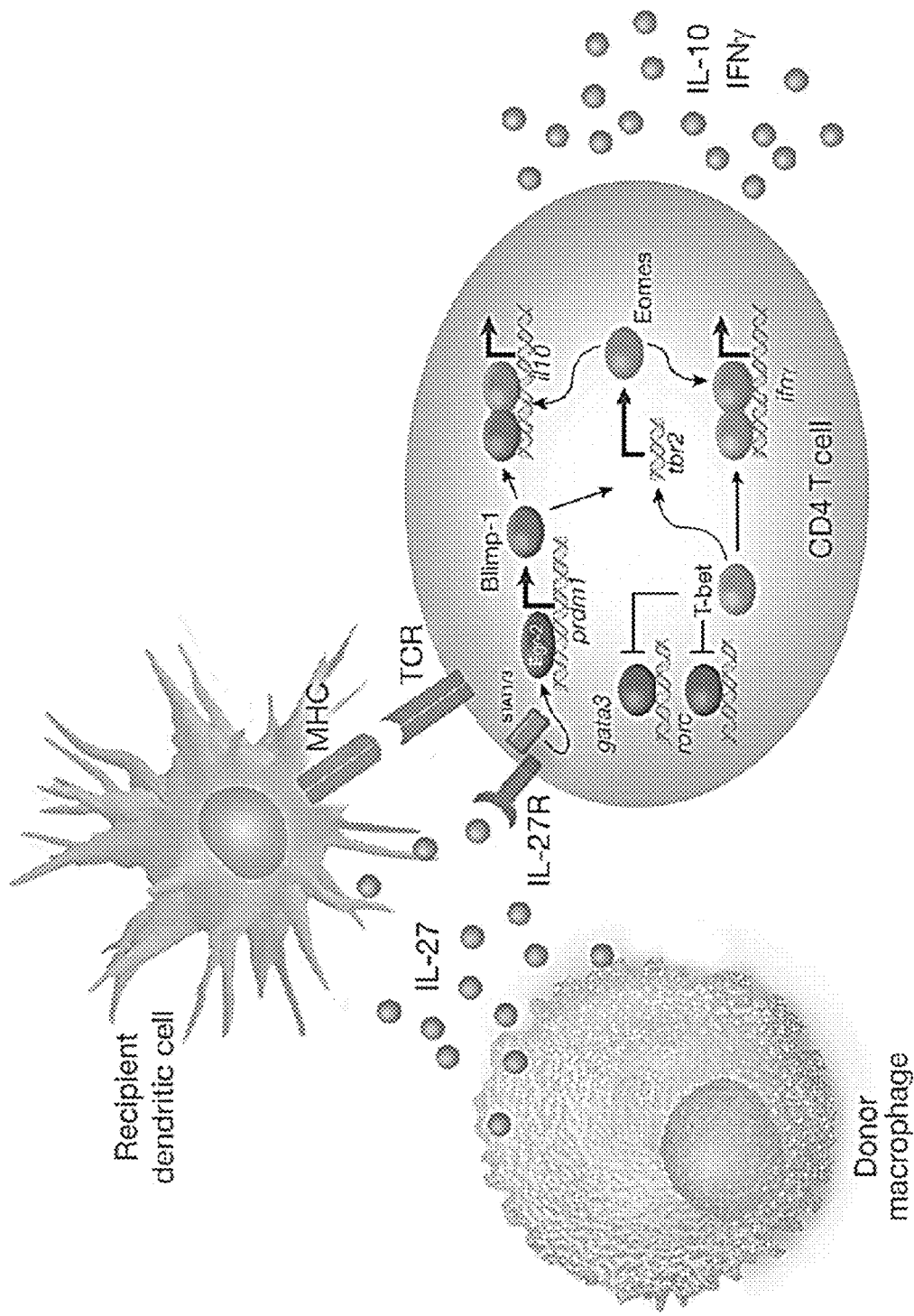

FIG. 19 is a schematic representation illustrating a proposed cellular and transcriptional regulation of $T_R1$ cell development after BMT.

Figure 20:
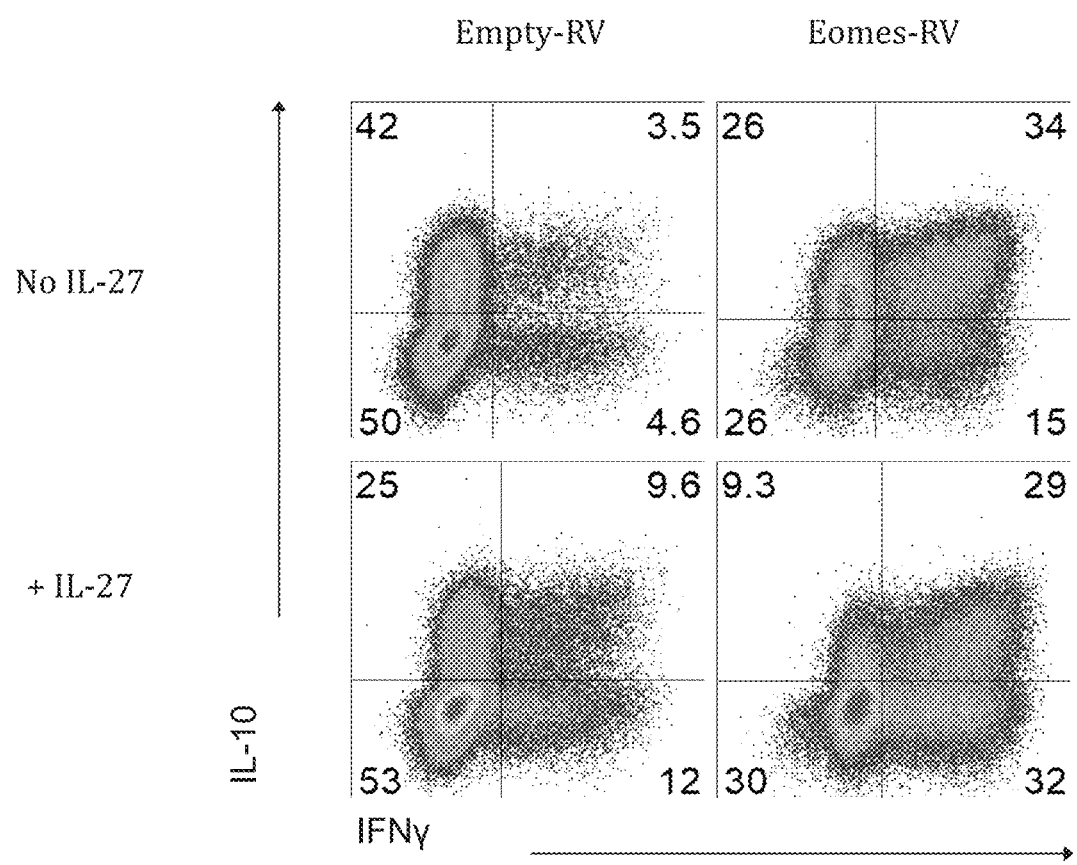

FIG. 20 is a graphical representation showing that Eomes over-expressing $T_R1$ cells are independent of IL-27. B6 splenic CD4+ T cells were retrovirally transduced with Eomes and then polarized to $T_R1$ cells after stimulation with plate bound CD3 and CD28. Representative plots show the frequency of IL-10+IFNγ+ $T_R1$ cells generated in the absence or presence of IL-27.

Figure 21:
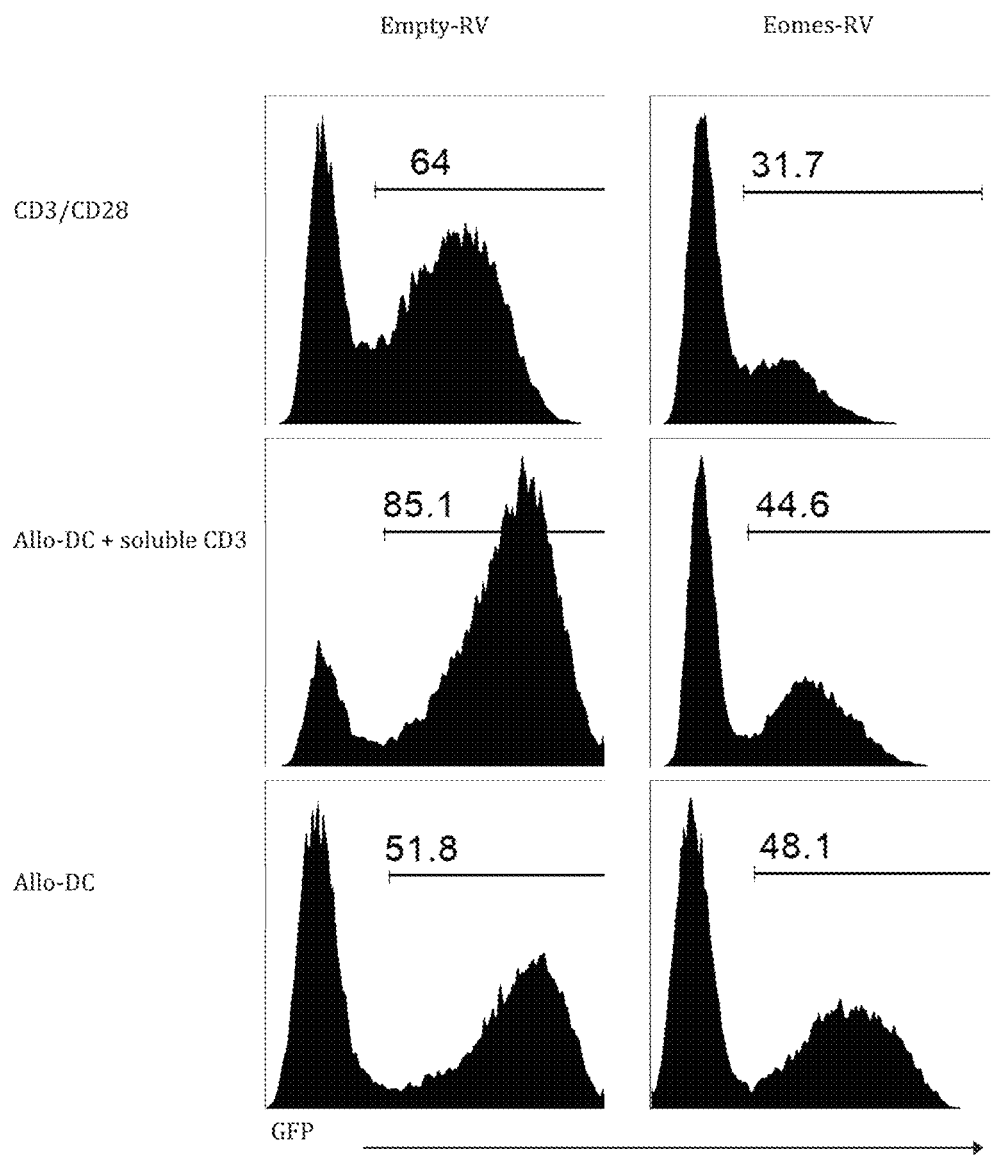

FIG. 21 is a graphical representation showing introduction of Eomes into alloantigen specific CD4+ T cells. B6 splenic CD4+ T cells were transduced in allo-antigen non-specific (stimulated with CD3/CD28) or allo-antigen specific (stimulated with allo-DC) manners respectively. Representative FACS plots showed the expression of GFP (indicating successful retroviral transduction) 2-4 days after retroviral transduction.

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, "and/or" refers to and encompasses any and all possible combinations of one or more of the associated listed items, as well as the lack of combinations when interpreted in the alternative (or).

As used herein, the term "anergy" or "tolerance" refers to insensitivity of T cells to T cell receptor-mediated stimulation. Such insensitivity is generally antigen-specific and persists after exposure to the tolerizing antigen has ceased. For example, anergy in T cells (as opposed to unresponsiveness) is characterized by lack of cytokine production, e.g., IL-2. T-cell anergy occurs when T cells are exposed to antigen and receive a first signal (a T cell receptor or CD-3 mediated signal) in the absence of a second signal (a costimulatory signal). Under these conditions, re-exposure of the cells to the same antigen (even if re-exposure occurs in the presence of a costimulatory molecule) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. 1992 Science. 257:1134).

"Autoimmunity" refers to persistent and progressive immune reactions to non-infectious self-antigens, as distinct from infectious non-self-antigens from bacterial, viral, fungal, or parasitic organisms which invade and persist within mammals and humans. Autoimmune conditions include scleroderma, Grave's disease, Crohn's disease, Sjogren's disease, multiple sclerosis, Hashimoto's disease, psoriasis, myasthenia gravis, Autoimmune Polyendocrinopathy syndromes, Type I diabetes mellitus (TIDM), autoimmune gastritis, autoimmune uveoretinitis, polymyositis, colitis, and thyroiditis, as well as in the generalized autoimmune diseases typified by human Lupus. "Autoantigen" or "self-antigen" as used herein refers to an antigen or epitope which is native to the mammal and which is immunogenic in said mammal disease. A patient with an autoimmune disease may be diagnosed as known to one of ordinary skill in the art. Such patients may be identified symptomatically and/or by obtaining a sample from a patient and isolating autoreactive T cells and comparing the level of autoreactive T cells in a patient to a control (see, U.S. Patent Application Publication No. 20060105336). For instance, type 1 diabetes may be identified by age of on-set and dependence on insulin injections to maintain glucose homeostasis. The response of a patient with an autoimmune disease to treatment may be monitored by determining the severity of their symptoms or by determining the frequency of autoreactive T cells in a sample from a patient with an autoimmune disease. The severity of symptoms of the autoimmune disease may correlate with the number of autoreactive T cells (see, U.S. Patent Application Publication No. 20060105336). In addition, an increase in the number of autoreactive T cells in the sample may be used as an indication to apply treatments intended to minimize the severity of the symptoms and/or treat the disease before the symptoms appear.

By "coding sequence" is meant any nucleic acid sequence that contributes to the code for the polypeptide product of a gene or for the final mRNA product of a gene (e.g. the mRNA product of a gene following splicing). By contrast, the term "non-coding sequence" refers to any nucleic acid sequence that does not contribute to the code for the polypeptide product of a gene or for the final mRNA product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be containing within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3rd edition Volumes 1, 2, and 3. J. F. Sambrook, D. W. Russell, and N. Irwin, Cold Spring Harbor Laboratory Press, 2000.

The terms "eliciting immune tolerance" and "inducing immune tolerance" are used interchangeably herein to refer to any mechanism by which a potentially injurious immune response is prevented, suppressed, or shifted to a non-injurious immune response, including initiating, triggering, causing, enhancing, amplifying, improving, augmenting or prolonging a state of complete or partial unresponsiveness of the immune system to substances or tissues that have the capacity to elicit an immune response. The initiation or enhancement of immune tolerance can be assessed using assays known to those skilled in the art including, but not limited to, antibody assays (for example ELISA assays), antigen specific cytotoxicity assays and the production of cytokines (for example ELISPOT assays).

Reference to "enriching" should be understood as a reference to increasing the ratio of cells expressing the desired phenotype relative to the cells not expressing the desired phenotype in the starting sample. This is achieved by removing or otherwise reducing the number of cells that do not express the desired phenotype. It should be understood that reference to enrichment is not limited to an enrichment step that removes all the cells not expressing the desired phenotype from the sample. Rather, it is a reference to decreasing the concentration of these suitably undesired cells in the test sample. The decrease in concentration may therefore be of varying degrees. The method of the present invention should be understood to encompass conducting one or more repeated sequential enrichment steps in order to improve the purity of the desired population (such as by performing two or more sequential enrichment steps for any one or more of CD4$^+$, CD122$^+$, $\alpha 4\beta 7^+$, LAG-3$^+$, Ly6C$^+$ and TIGIT$^+$, CD25$^{lo/}$, CD69$^{lo/-}$ and FoxP3$^{lo/-}$). The decision as to whether one or more enrichment steps are required to be performed at any given stage can be made by a person skilled in the art on a case by case basis. When T cell numbers are relatively high (such as in a PBMC sample), a single enrichment step may be sufficient to enrich for the desired population. However, where a sample with very low numbers of T cells is used, it may be desirable to perform two or more of each enrichment step in order to maximize the purity of the desired cellular population. For example, in some preferred embodiments, enriching a cell population refers to increasing the percentage by about 10%, by about 20%, by about 30%, by about 40%, by about 50% or greater than 50% of one type of cell in a population of cells as compared to the starting population of cells. In other preferred embodiments, enriched cell populations of the present invention will comprise at least 30%, 40%, 50%, 60% 70%, 80%, 85%, 90%, 95%, 98%, or 99% of the selected cell type. In yet other embodiments, an enriched preparation of immunoregulatory T cells may be described as comprising about 1% or greater or about 0.5% to about 40% of the total cell population contained in a preparation. In some embodiments, the enriched preparations comprise a 100-fold, 200-fold, 500-fold, 1,000-fold, or up to a 2,000-fold or 10,000-fold to 20,000-fold enriched preparation of immunoregulatory T cells. In specific embodiments, enriched T-cell samples refer to those samples or biological samples that have been enriched for T cells by positive selection of the T cells bearing the CD4 marker by determining the levels of expression of the CD4 marker. Other enriched T-cell samples have been enriched for T-cells by negative selection of (i.e., selecting against) non-T-cells which can be distinguished by their levels of expression of other common determinants.

"Eomes" refers to Eomesodermin, a protein that in humans is encoded by the Eomes gene. Eomes is a transcriptional regulator. Representative coding sequences forum human Eomes are set forth in NCBI Accessions NM_001278182, NM_005442 and NM_001278183.

The term "exogenous" refers to any material introduced from or produced outside an organism, cell, tissue or system.

The term "expression" with respect to a gene sequence refers to transcription of the gene to produce a RNA transcript (e.g., mRNA, antisense RNA, siRNA, shRNA, miRNA, etc.) and, as appropriate, translation of a resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, the term "graft" or "transplant" refers to an organ, tissue, or cell that has been transplanted from one subject to a different subject, or transplanted within the same subject (e.g., to a different area within the subject). Organs such as liver, kidney, heart or lung, or other body parts, such as bone or skeletal matrix such as bone marrow, tissue, such as skin, intestines, endocrine glands, or stem cells of various types, or hematopoietic cells including hematopoietic stem and progenitor cells, are all examples of transplants. The graft or transplant can be an allograft, autograft, isograft or xenograft. The term "allograft" refers to a graft between two genetically non-identical members of a species. The term "autograft" refers to a graft from one area to another on a single individual. The term "isograft" or "syngraft" refers to a graft between two genetically identical individuals. The term "xenograft" refers to a graft between members of different species.

Immune conditions, diseases, disorders and reactions or responses to be treated according to the methods and compositions of the invention means a disease in which the immune system contributes to pathogenesis. These reactions include, but are not limited to, inflammatory disorders, cancer, autoimmune conditions, disorders or diseases and persistent and progressive immune reactions to infectious non-self-antigens from bacterial, viral (e.g., HCV), fungal, or parasitic organisms which invade and persist within mammals and humans. Such conditions and disorders include allergies and/or asthma. The allergies and asthma may be due to sensitization with foreign or non-self-antigens as pollen, animal dander and food proteins. The source of the provoking foreign antigen can be plant, fungal, mold, or other environmental contaminants.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly brought about by T cell activation, e.g., antibody production (humoral responses) and activation of cytokine responsive cells, e.g., macrophages. Immune cells involved in the immune response include lymphocytes, such as B cells and T cells (CD4$^+$, CD8$^+$, Th1 and Th2 cells); antigen presenting cells (e.g., professional antigen presenting cells such as B lymphocytes, monocytes, dendritic cells, Langerhans cells, and non-professional antigen presenting cells such as keratinocytes, endothelial cells, astrocytes, fibroblasts, oligodendrocytes); natural killer cells; myeloid cells, such as monocytes, macrophages, eosinophils, mast cells, basophils, and granulocytes.

The term "immunoregulatory" refers to an agent that inhibits or reduces one or more biological activities of the immune system. An immunoregulatory agent is an agent that inhibits or reduces one or more biological activities (e.g., the proliferation, differentiation, priming, effector function, production of cytokines or expression of antigens) of one or more immune cells (e.g., T cells).

The term "isolated cell" as used herein refers to a cell that has been removed from an organism in which it was originally found, or a descendant of such a cell. Optionally, the cell has been cultured in vitro, e.g., in the presence of other cells. Optionally, the cell has been cultured in vitro, e.g., in the presence of other cells.

The term "isolated population" with respect to an isolated population of cells as used herein refers to a population of cells that has been removed and separated from a mixed or heterogenous population of cells. In some embodiments, an isolated population is a substantially homogenous population of cells as compared to the heterogenous population from which the cells were isolated or enriched. In some embodiments, the isolated population is an isolated population of immunoregulatory T cells, e.g., a substantially homogenous population of human immunoregulatory T cells as compared to a heterogenous population of cells comprising immunoregulatory T cells from which the human immunoregulatory T cells were derived. Isolated populations will typically comprise a plurality of cells, preferably at least $10^3$, $10^4$, $10^5$, $10^6$, $10^7$, $10^8$, $10^9$, $10^{10}$, or $10^{11}$ cells. The population in some embodiments has from $10^5$ to $10^7$ cells, $10^6$ to $10^8$ cells, or from $10^8$ to $10^{11}$ cells, or $10^{10}$ to $10^{12}$ cells.

A "marker" and "cell marker" and the like, as used herein in the context of a cell, means any trait or characteristic in the form of a chemical or biological entity (including phenotypic and genotypic traits) that is identifiably associated with, or specifically found in or on a particular cell, cell population or tissue, including those identified in or on a tissue or cell population affected by a disease or disorder. Markers may be morphological, functional or biochemical in nature and may be genotypic or phenotypic. In preferred embodiments that marker is a cell surface antigen or genetic component that is differentially or preferentially expressed (or is not) by specific cell types (e.g., immunoregulatory T cells) or by cells under certain conditions (e.g., during specific points of the cell cycle or cells in a particular niche). In still other preferred embodiments the marker may comprise a gene or genetic entity that is differentially regulated (up or down) in a specific cell or discrete cell population, a gene that is differentially modified with regard to its physical structure and chemical composition or a protein or collection of proteins physically associated with a gene that show differential chemical modifications. Markers contemplated herein are specifically held to be positive or negative and may denote a cell or cell population by its present (positive) or absence (negative).

By "obtained from" is meant that a sample such as, for example, a cell or tissue sample is isolated from, or derived from, a particular source.

The term "operably connected" or "operably linked" as used herein refers to a juxtaposition wherein the components so described are in a relationship permitting them to function in their intended manner. For example, a regulatory sequence (e.g., a promoter) "operably linked" to a nucleotide sequence of interest (e.g., a coding and/or non-coding sequence) refers to positioning and/or orientation of the control sequence relative to the nucleotide sequence of interest to permit expression of that sequence under conditions compatible with the control sequence. The control sequences need not be contiguous with the nucleotide sequence of interest, so long as they function to direct its expression. Thus, for example, intervening non-coding sequences (e.g., untranslated, yet transcribed, sequences) can be present between a promoter and a coding sequence, and the promoter sequence can still be considered "operably linked" to the coding sequence.

The terms "patient", "subject", "host" or "individual" used interchangeably herein, refer to any subject, particularly a vertebrate subject, and even more particularly a mammalian subject, for whom therapy, or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papia ursinus*), as well as marmosets (species from the genus *Callithrix*), squirrel monkeys (species from the genus *Saimiri*) and tamarins (species from the genus *Saguinus*), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. A preferred subject is a human in need of eliciting immune tolerance. However, it will be understood that the aforementioned terms do not imply that symptoms are present.

By "pharmaceutically acceptable carrier" is meant a solid or liquid filler, diluent or encapsulating substance that can be safely used in topical or systemic administration to an animal, preferably a mammal, including humans. Representative pharmaceutically acceptable carriers include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient(s), its use in the pharmaceutical compositions is contemplated.

A "pharmaceutical composition" is intended to include the combination of an active agent with a carrier, inert or active such as biocompatible scaffold or matrix, making the composition suitable for diagnostic or therapeutic use in vitro, in vivo, or ex viva.

Reference to "phenotypic profile" should be understood as a reference to the presence or absence of the transcription of the genes encoding the subject markers and/or the cell surface expression of the expression product translated therefrom. It should be appreciated that although most cells falling within the scope of the claimed immunoregulatory T cell populations will be characterized by the presence or absence of the subject marker as a cell surface anchored expression product, some cells falling within the defined populations may initially exhibit changes only at the transcriptome level, such as when the transcription of a given marker has been upregulated but may not yet have resulted in a cell surface anchored expression product. In general, cells which progress to a new differentiative stage will transiently exhibit gene expression changes which are not yet evident in the context of changes to levels of an expression product. However, these cells nevertheless fall within the scope of the claimed cellular populations, although they will not be isolatable by the method defined herein until such time as cell surface marker expression occurs.

"Positive," "low" and "negative" expression levels as they apply to markers are defined as follows. Cells with negative expression (i.e., "−") are herein defined as those cells expressing less than, or equal to, the $95^{th}$ percentile of expression observed with an isotype control antibody in the channel of fluorescence in the present of the complete antibody staining cocktail labelling for other proteins of interest in additional channels of fluorescence emission. Those skilled in the art will appreciate that this procedure for defining negative events is referred to as "fluorescence minus one," or "FMO," staining. Cells with expression greater than the 95$^{th}$ percentile of expression observed with an isotype control antibody using the FMO staining procedure described above are herein defined as "positive" (i.e., "+"). As defined herein there are various populations of cells broadly defined as "positive." First, cells with low expression (i.e., "1o") age generally defined as those cells with observed expression above the 95$^{th}$ percentile determined using FMO staining with an isotype control antibody and within one standard deviation of the 95$^{th}$ percentile of expression observed with an isotype control antibody using the FMO staining procedure described above. The term "lo" in relation to Tbet$^{lo}$ refers to a distinct cell or population of cells that expresses Tbet at a lower level than one or more other distinct cells or populations of cells.

The term "recombinant expression" and its grammatical equivalents (e.g., "recombinantly expressing"), as used herein, relates to transcription and translation of an exogenous gene in a host cell. Exogenous DNA refers to any deoxyribonucleic acid that originates outside of the host cell. The exogenous DNA may be integrated in the genome of the host cell or may be expressed from a non-integrating element.

"Regulatory sequences", "regulatory elements", control elements", "control sequences" and the like are used interchangeably herein to refer to nucleotide sequences located upstream (5' non-coding sequences), within, or downstream (3' non-coding sequences) of a coding sequence, and which influence the transcription, RNA processing or stability, or translation of the associated coding sequence, either directly or indirectly. Regulatory elements include enhancers, promoters, translation leader sequences, introns, Rep recognition element, intergenic regions and polyadenylation signal sequences. They include natural and synthetic sequences as well as sequences which may be a combination of synthetic and natural sequences.

For the purposes of the present invention, the terms "purifying," "sorting," "selecting" or "isolating" specific cells, cell populations, or cell populations, may be used interchangeably and mean, unless otherwise dictated by context, that a selected cell or defined subset of cells are removed from a tissue sample or cellular preparation, and separated from other cells and contaminants that are not within the parameters defining the cell or cell population. In some embodiments, an isolated immunoregulatory population of T cells is substantially free from contamination by other cell types. However, when the process or treatment results in a cell population it is understood that it is impractical to provide compositions of absolute purity. In such cases that cell population is "enriched" for the selected cells that then exist in the presence of various contaminants (including other cell types) that do not materially interfere with the function or properties of the selected cell population.

The term "separation" or "selection" as used herein refers to isolating different cell types into one or more populations and collecting the isolated population as a target cell population which is enriched in a specific immunoregulatory T cell population. Selection can be performed using positive selection, whereby a target enriched cell population is retained, or negative selection, whereby non-target cell types are discarded (thereby enriching for desired target cell types in the remaining cell population).

The term "positive selection" as used herein refers to selection of a desired cell type by retaining the cells of interest. In some embodiments, positive selection involves the use of an agent to assist in retaining the cells of interest (e.g., use of a positive selection agent such as an antibody which has specific binding affinity for a surface antigen on the desired or target cell. In some embodiments, positive selection can occur in the absence of a positive selection agent (e.g., in a "touch-free" or closed system), for example, where positive selection of a target cell type is based on any of cell size, density, and/or morphology of the target cell type.

The term "negative selection" as used herein refers to selection of undesired or non-target system cells for depletion of discarding, thereby retaining (and thus enriching) the desired target cell type. In some embodiments, negative selection involves the use of an agent to assist in selecting undesirable cells for discarding, e.g., use of a negative selection agent such as an antibody which has specific binding affinity for a surface antigen on unwanted or non-target cells. In some embodiments, negative selection does not involve a negative selection agent. In some embodiments, negative selection can occur in the absence of a negative selection agent, e.g., in a "touch-free" or closed system, for example, where negative selection of an undesired cell (non-target) cell type.

As used herein, the term "sample" or "biological sample" refers to tissues or body fluids removed from a mammal, preferably human, and which contain immunoregulatory T cells, including, but not limited to, Eomes$^+$IL-10$^+$ T cells. In some embodiments, the samples are taken from individuals with an immune response which needs to be suppressed. In some embodiments, the individual has an allergy, Graft vs. Host Disease, an organ transplant, or autoimmune disorder. Samples preferably are blood and blood fractions, including peripheral blood. The biological sample is drawn from the body of a mammal, such as a human, and may be blood, bone marrow cells, or similar tissues or cells from an organ afflicted with the unwanted immune response. Methods for obtaining such samples are well known to workers in the fields of cellular immunology and surgery. They include sampling blood in well-known ways or obtaining biopsies from the bone marrow or other tissue or organ. In preferred embodiments, the sample is a T-cell enriched sample in which the sample cells are substantially T-cells.

"Substantially homogeneous" cell population describes a population of cells in which more than about 75%, or alternatively more than 80%, or alternatively more than 85%, or alternatively more than 90%, or alternatively, more than 95%, of the cells are of the same or similar phenotype. Phenotype is determined by the cell surface markers described in more detail herein.

The terms "treating" "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, bur has not yet been diagnosed as having it; inhibiting a disorder arresting its development); and/or relieving or ameliorating the symptoms of disorder. As it understood by those skilled in the art "treatment" can include systemic amelioration of the symptoms associated with the pathology and/or a delay in onset of symptoms. Clinical and sub-clinical evidence of "treatment" will vary with the pathology, the individual and the treatment.

"Tolerogenic" means silencing or down-modulating an immune response. The term "tolerogenic" also refers to a phenotype of a cell or a substance that induces immune tolerance, typically to an antigen directly or indirectly.

The term "$T_R1$ cells" as used herein refers to cells having the following phenotype at rest CD4$^+$CD25$^-$FoxP3$^-$ and capable of secreting high levels of IL-10 and significant levels TGF-β upon activation. $T_R1$ cells are generally characterized, in part, by their unique cytokine profile: they produce high levels of IL-10, significant levels of TGF-β and intermediate levels of IFN-γ, but little or no IL-4 or IL-2. The cytokine production is typically evaluated in cultures of cells after activation with polyclonal activators of T lymphocytes such as anti-CD3 anti-CD28 antibodies or IL-2, PMA ionomycin. Alternatively, the cytokine production is evaluated in cultures of cells after activation with the specific T-cell antigen presented by antigen presenting cells such as dendritic cells (DC) or monocytes. High levels of IL-10 correspond to at least about 500 pg/mL, typically greater than about 1, 2, 4, 6, 8, 10, 12, 14, 16, 18, or 20 thousand pg/mL or more. Significant levels of TGF-β correspond to at least about 100 pg/mL, typically greater than about 200, 300, 400, 600, 800, or 1000 pg/mL or more. Intermediate levels of IFN-γ correspond to concentrations comprised between 0 pg/mL and at least 400 pg/mL, typically greater than about 600, 800, 1000, 1200, 1400, 1600, 1800, or 2000 pg/mL or more. Little or no IL-4 or IL-2 corresponds to less than about 500 pg/mL, preferably less than about 250, 100, 75, or 50 pg/mL, or less.

As used herein, underscoring or italicizing the name of a gene shall indicate the gene, in contrast to its protein product, which is indicated by the name of the gene in the absence of any underscoring or italicizing. For example, "Eomes" shall mean the Eomes gene or Eomes polynucleotides, whereas "Eomes" shall indicate the protein product or products generated from transcription and translation and alternative splicing of the "Eomes" gene.

Each embodiment described herein is to be applied mutatis mutandis to each and every embodiment unless specifically stated otherwise.

In order that the invention may be readily understood and put into practical effect, particular preferred embodiments will now be described by way of the following non-limiting examples.

Experimental 1

$T_R1$ Cells Represent a Major Regulatory T Cell Population in GVHD

Figure 1B:
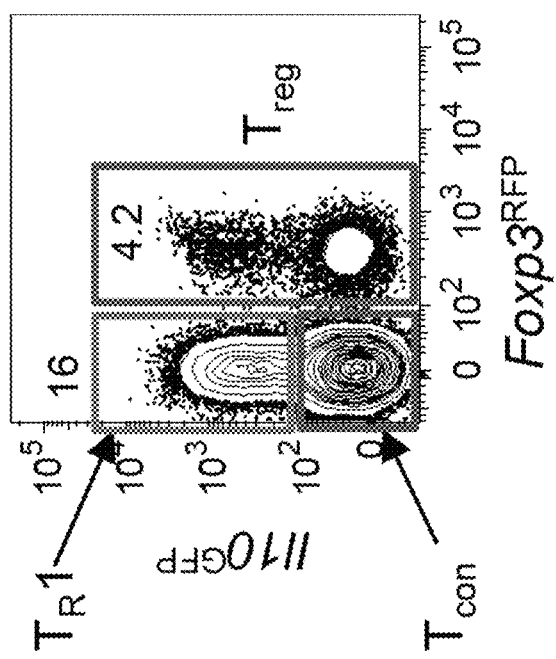
FIG. 1 is a graphical representation showing that $T_R1$ cells constitute the major regulatory T cell after allogeneic BMT. (A-E) B6 (Syn) and B6D2F1 (Allo) mice were transplanted with B6 CD3$^+$ T (Il10$^{GFP}$/Foxp3$^{RFP}$). (A) Gating strategy after BMT for analysis and FACS sorting of $T_R1$ (red), $T_{reg}$ (blue) and $T_{con}$ (green) cells. (8) Schema of BMT. (C) Expression of IL-10 and FoxP3 in the spleen at d14 (representative of >3 experiments). (D) Frequencies of $T_R1$ and $T_{reg}$ cells at d 14 (Il10$^{GFP+}$: solid bar; Il10$^{GFPneg}$: open bar). (E) CD4$^+$ T cell subsets in spleen after BMT (n=8-9 per group each time point). (f) B6D2F1 mice were transplanted with B6 CD4$^+$ T (Il10$^{GFP}$ and Foxp3$^{RFP}$) and frequencies of $T_R1$ and $T_{reg}$ cells in the spleen at d14 (n=14). (6) Suppression of proliferation of CFSE labelled B6 CD4$^+$ and CD8$^+$ responder T cells in vitro by naïve $T_{reg}$ cells versus $T_R1$, $T_{reg}$ and $T_{con}$ "suppressors" sorted from 10 transplant recipients at d14 (data combined from 2 experiments). (H) Experimental BMT schema showing adoptive transfer of sorted $T_R1$ cells to treat established acute GVHD and (1) survival of recipients are shown (n=8 in TCD group, others n=11-12). Data represents mean±SEM.
Figure 1A:
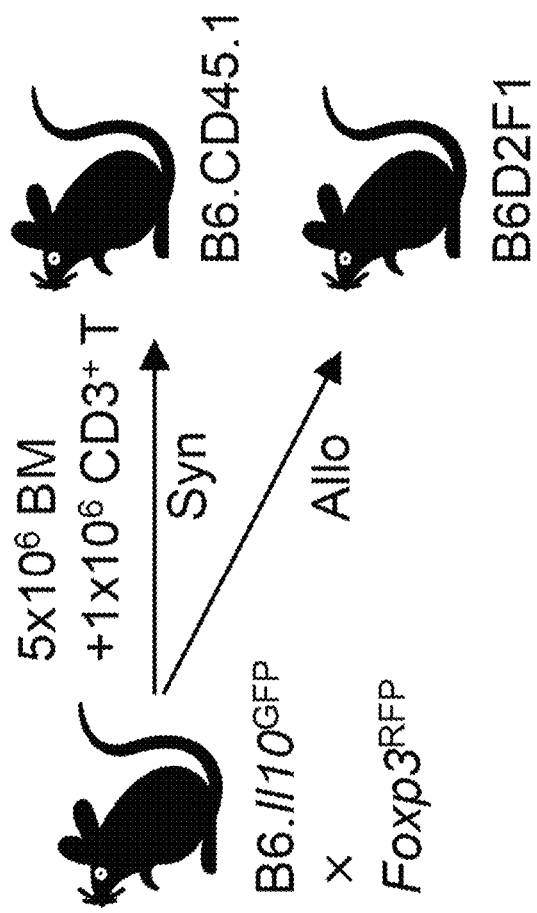
Figure 1C:
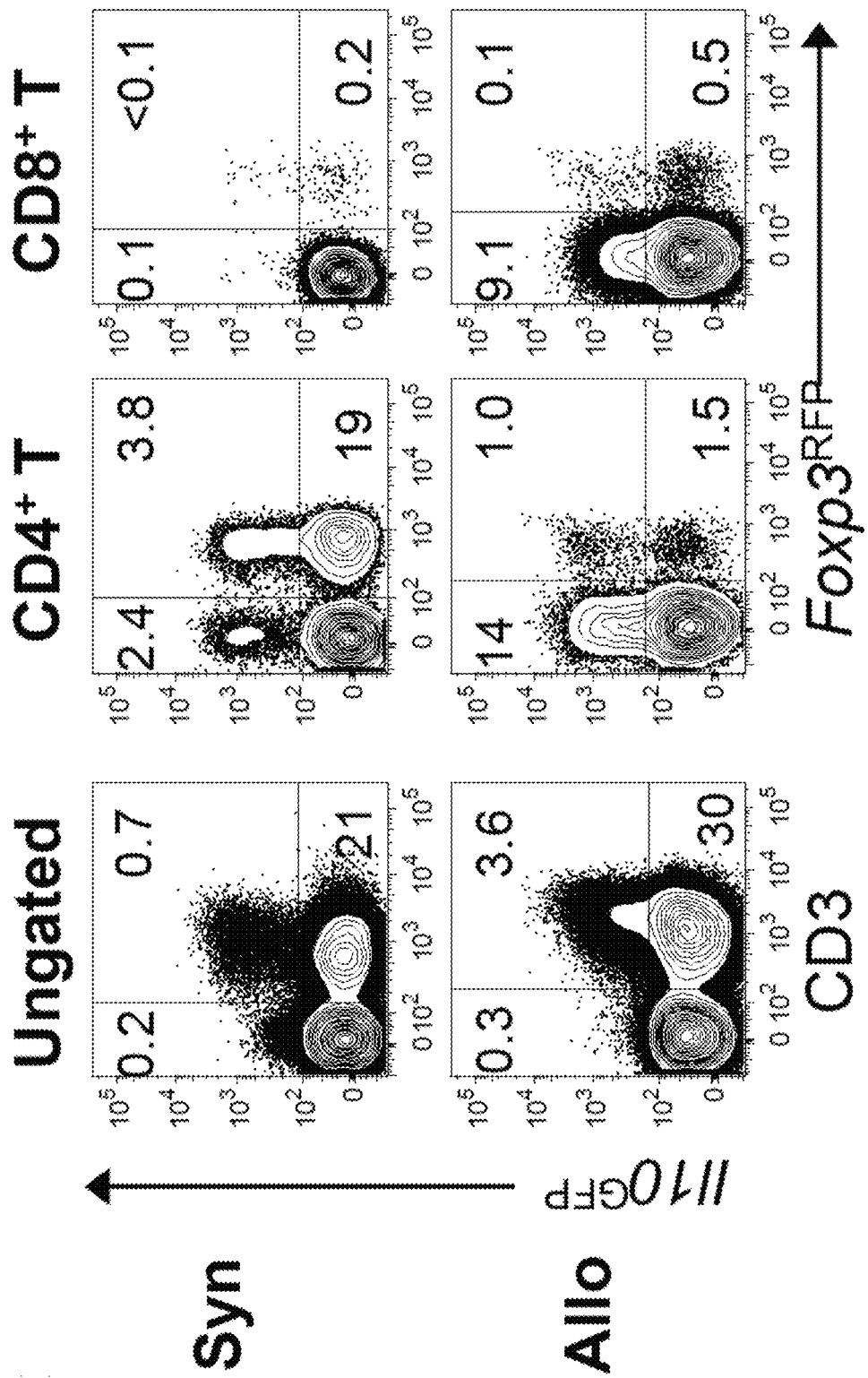
Figure 1D:
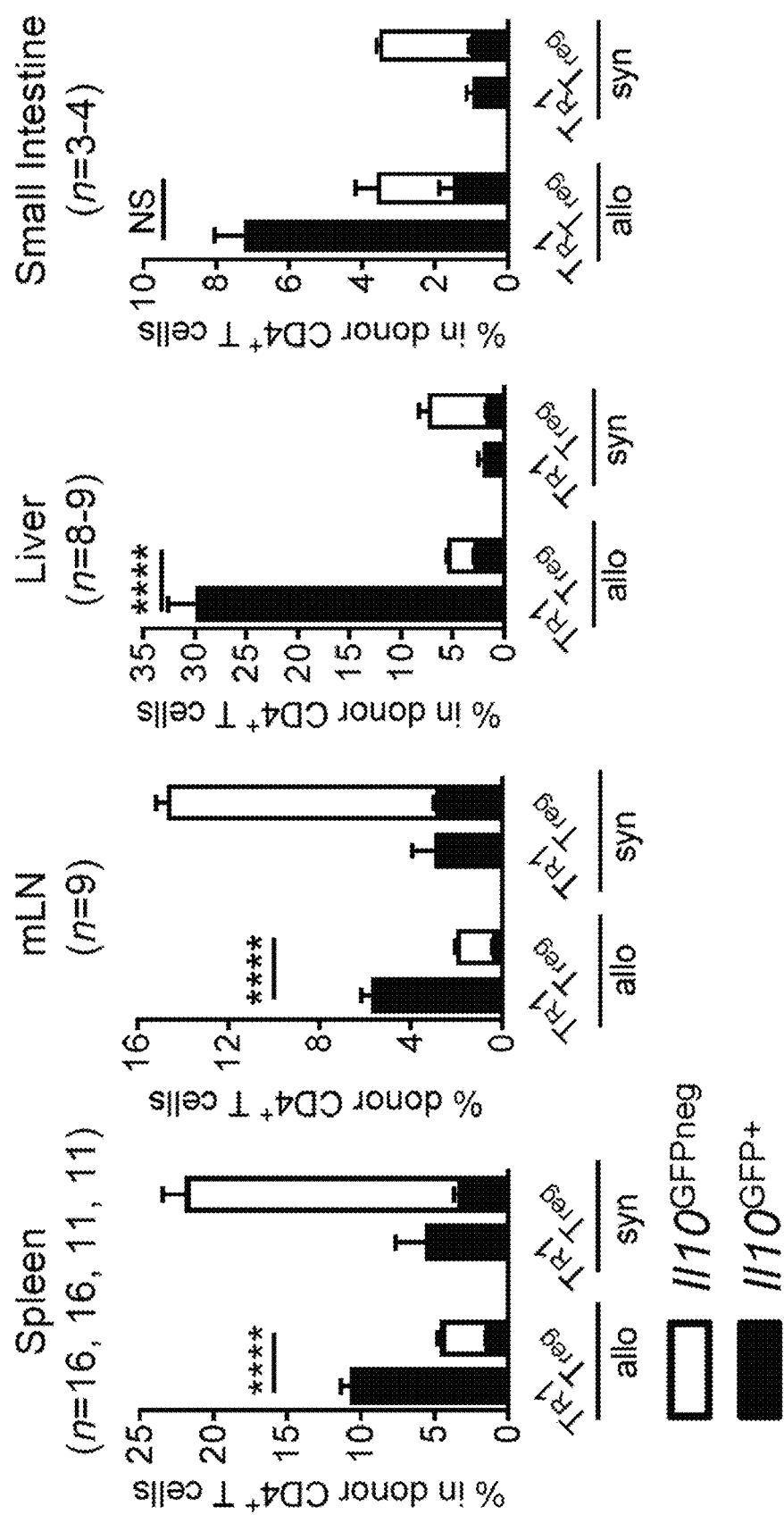
Figures 1G, 1H:
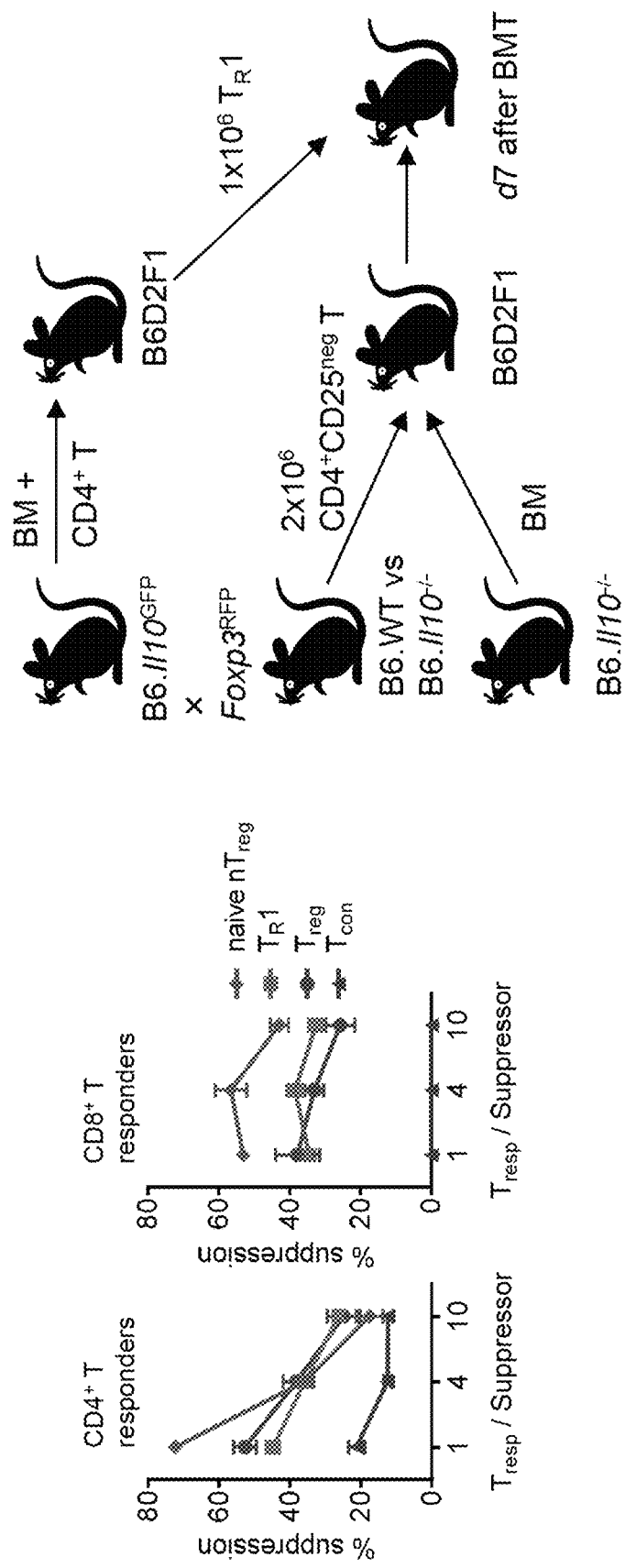
Figure 1I:
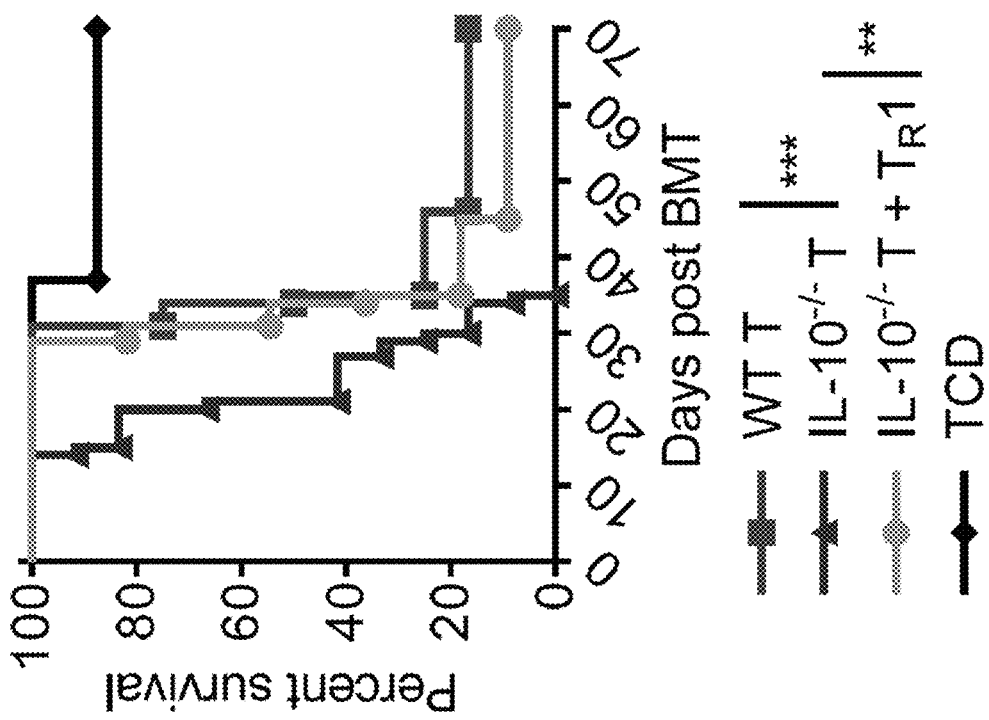
Figure 9:
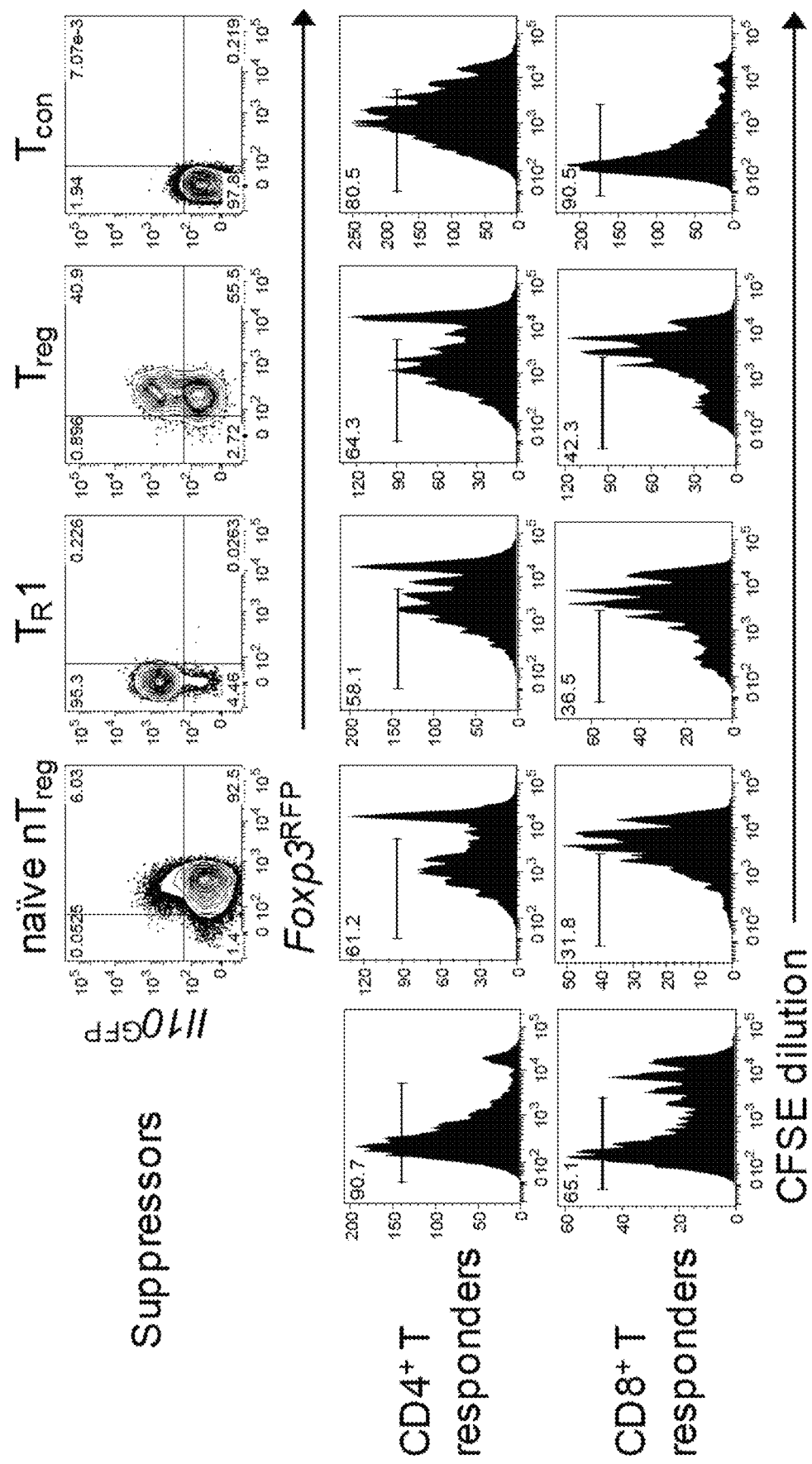
FIG. 9 is a graphical representation showing that $T_R1$ cells are suppressive in vitro. Representative plots (of FIG. 1g) show in vitro suppression of proliferation of CFSE labelled B6 CD4$^+$ and CD8 responder T cells by naïve $T_{reg}$ cells versus $T_R1$, $T_{reg}$ and $T_{con}$ "suppressors" sorted from transplant recipients at d14 (responder to suppressor at 4:1 ratio).

The present inventors used Il10$^{GFP}$ and Foxp3$^{RFP}$ dual reporter mice as BMT donors to define CD4$^+$FoxP3$^{neg}$ IL-10$^+$ type-1 regulatory T ($T_R1$) cells, CD4$^+$FoxP3$^+$ regulatory T ($T_{reg}$) cells and CD4$^+$FoxP3$^{neg}$ IL-10$^{neg}$ conventional T ($T_{con}$) cells (FIG. 1A). T cells were the major IL-10 producers after both allogeneic and syngeneic BMT (FIG. 15), with the highest proportion and intensity of IL-10 produced by $T_R1$ cells (FIG. 1C). Importantly, $T_R1$ cells were present at up to 10-fold higher frequency and number than $T_{reg}$ cells after allogeneic BMT in GVHD target tissues (liver, and to lesser extent small intestine), mesenteric lymph nodes (FIG. 10) and spleen (FIG. 1D-F). $T_R1$ cells induced under these conditions had suppressive properties in vitro equivalent to post-transplant $T_{reg}$ cells on a per cell basis (FIGS. 1G, 9). To confirm their suppressive function in viva, GVHD was induced with WT or Il10$^{-/-}$ CD4$^+$CD25$^{neg}$ T cells that cannot develop into functional $T_R1$ cells. As expected, enhanced GVHD was observed in the absence of IL-10; however, adoptive transfer of limited numbers of $T_R1$ cells at d7 after BMT (FIG. 1H) when acute GVHD was established, prolonged survival significantly (FIG. 1I), consistent with potent regulatory function. Thus, $T_R1$ cells represent the major regulatory T cell population in GVHD induced by allogeneic BMT and contribute significantly to transplant survival.

$T_R1$ Cells Express Eomes and Display a Distinct Phenotypic Profile

Figure 2A:
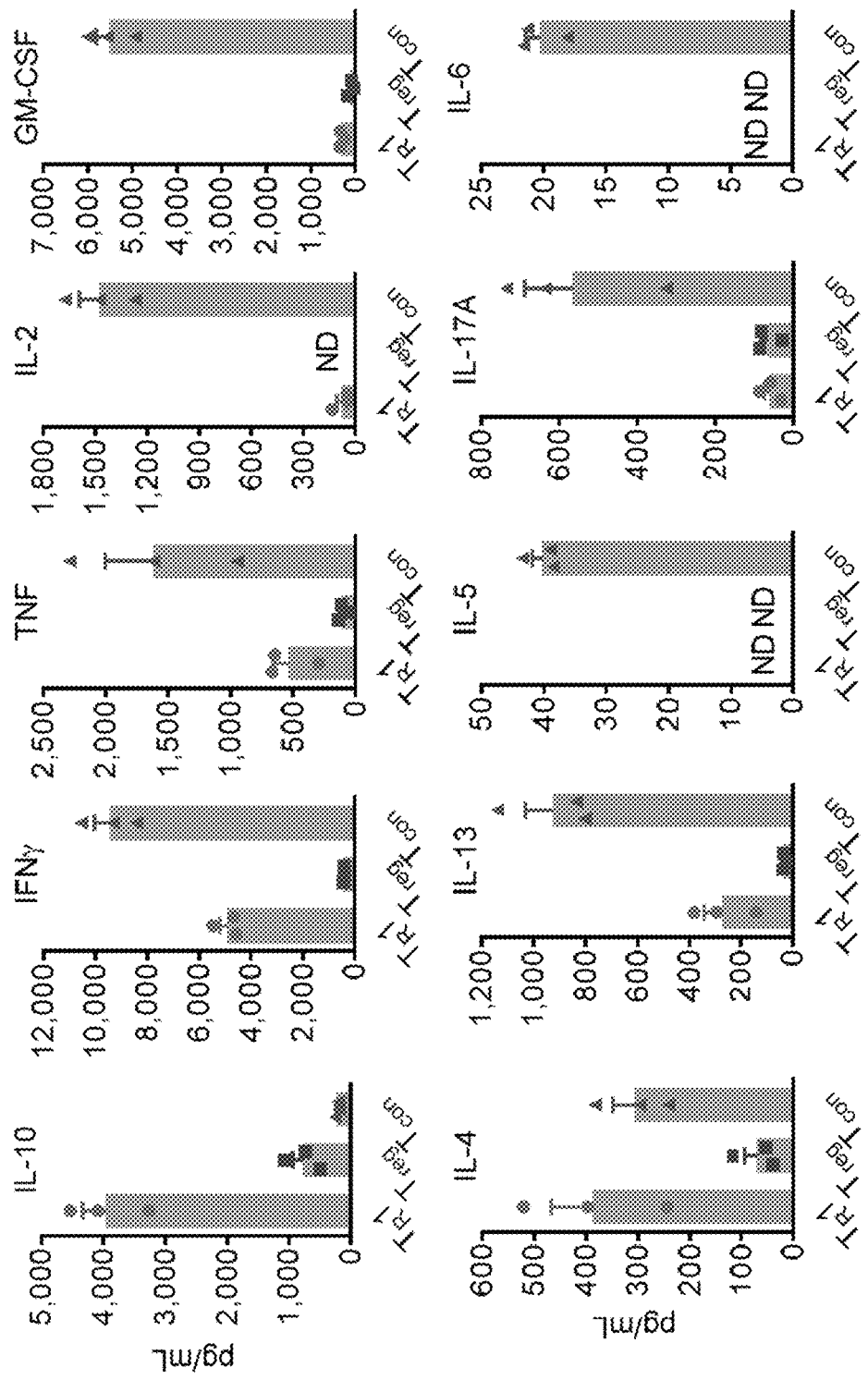
FIG. 2 is a graphical representation showing that $T_R1$ cells express Eomes and display a distinct phenotypic profile. (A-C) B6D2F1 mice were transplanted with Il10$^{GFP}$Foxp3$^{RFP}$ B6 CD3$^+$ T cells. CD4$^+$ T cells from spleen were FACS sorted into $T_R1$, $T_{reg}$ and $T_{con}$ cells at d14 as in FIG. 1A. (Data from 3 experiments, ND=not detectable) (A) Cytokine production in culture supernatant of T cell subsets. (B) Expression of transcription factors in T cell subsets ($T_R1$: red, $T_{reg}$: blue, $T_{con}$: green, isotype: gray). (C) Expression of cytokines and Eomes in T cell subsets. Data represents mean±SEM.
Figure 2B:
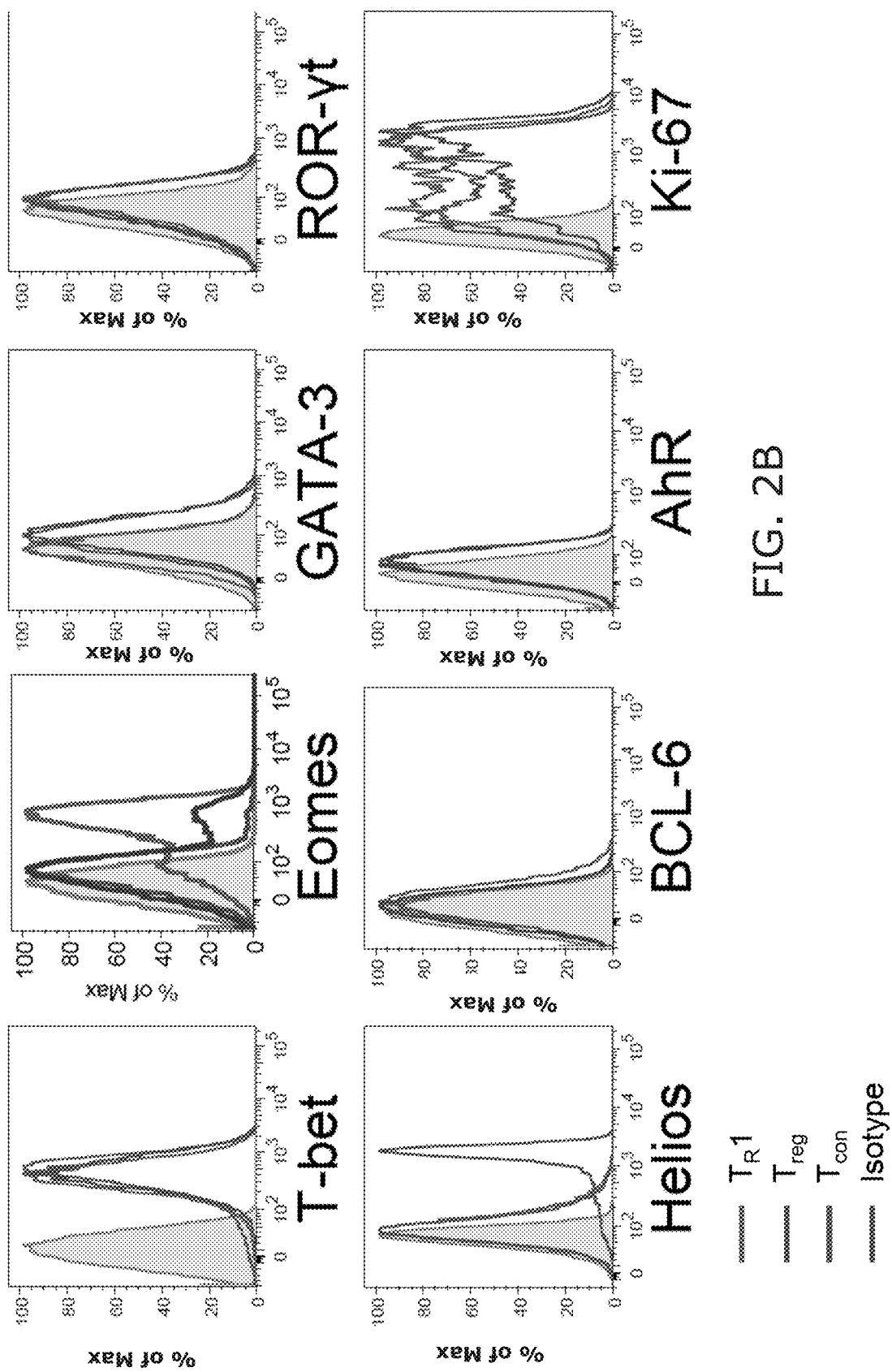
Figure 10A:
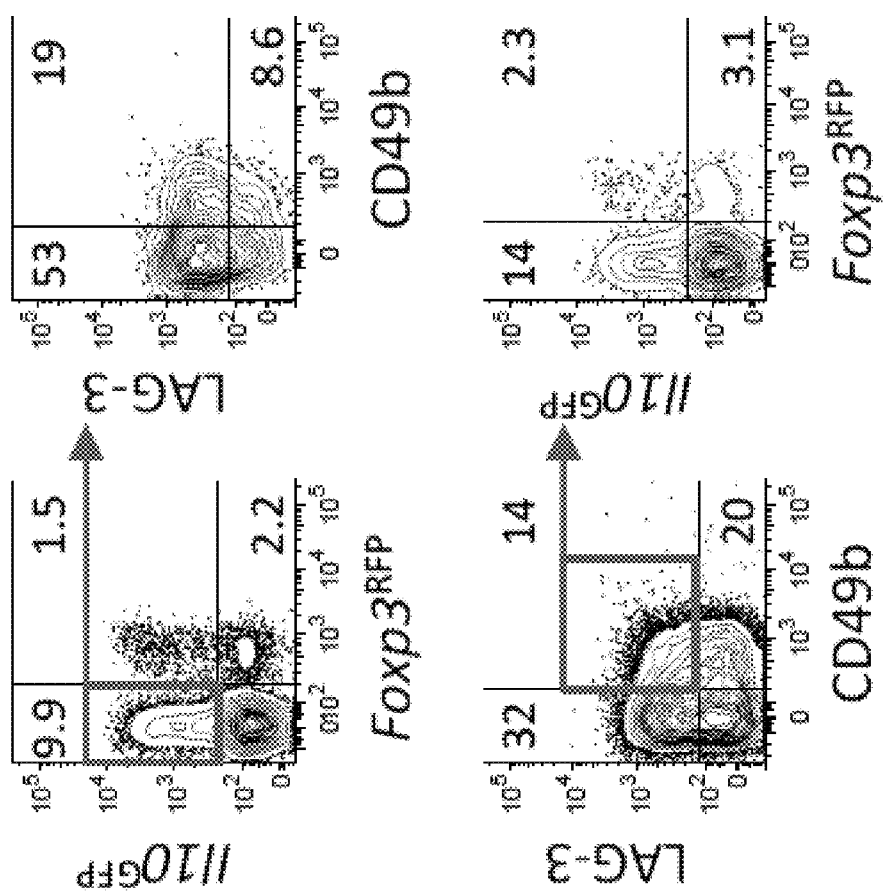
FIG. 10 is a graphical representation showing that $T_R1$ cells display a distinct profile of markers. (A and B) B6D2F1 mice were transplanted with B6 Il10$^{GFP}$ Foxp3$^{RFP}$ CD3$^+$ or CD4$^+$ T cells and splenic phenotypes examined at d14. (A) Expression of LAG-3/CD49b and FoxP3/IL-10 in CD4$^+$ T cell subsets at d14. (8) Representative plots demonstrate the expression of surface molecules in $T_R1$ (FoxP3$^{neg}$IL-10$^+$, red), $T_{reg}$ (FoxP3$^+$, blue) and $T_{con}$ (FoxP3$^{neg}$IL-10$^{neg}$, green) cells as compared to isotype controls (solid shade). (Data are representative of >2 experiments). (C and D) $T_R1$, $T_{reg}$ and $T_{con}$ cells are processed as described in FIG. 2A. Expression of IL-10 and IFNγ by intracellular cytokine staining (ICS) and expression of Eomes in T cell subsets. Data represents mean±S.E.M.
Figure 10B:
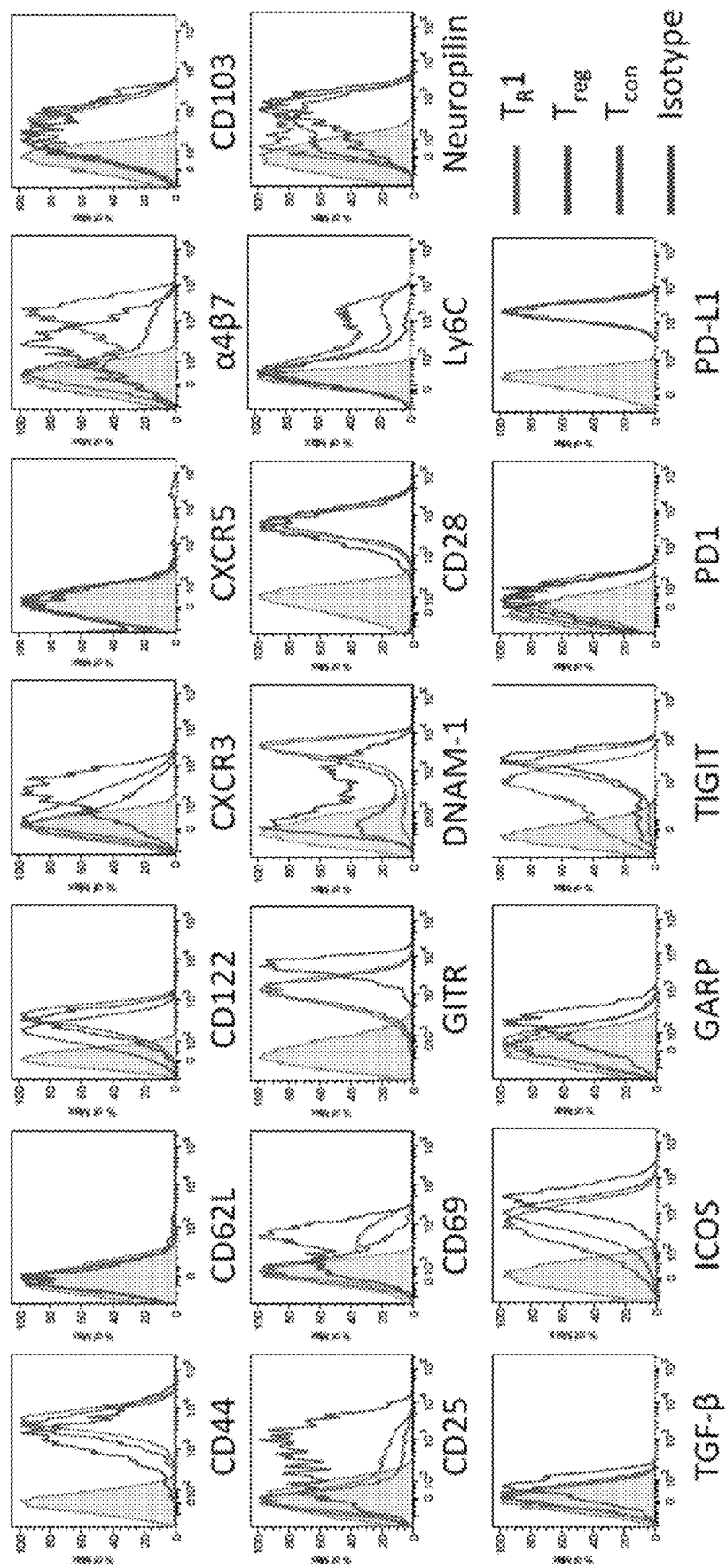
Figure 10D:
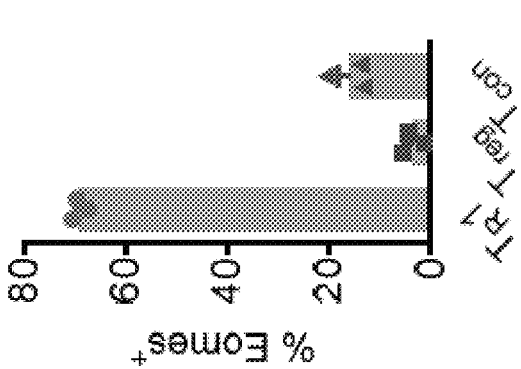
Figure 10C:
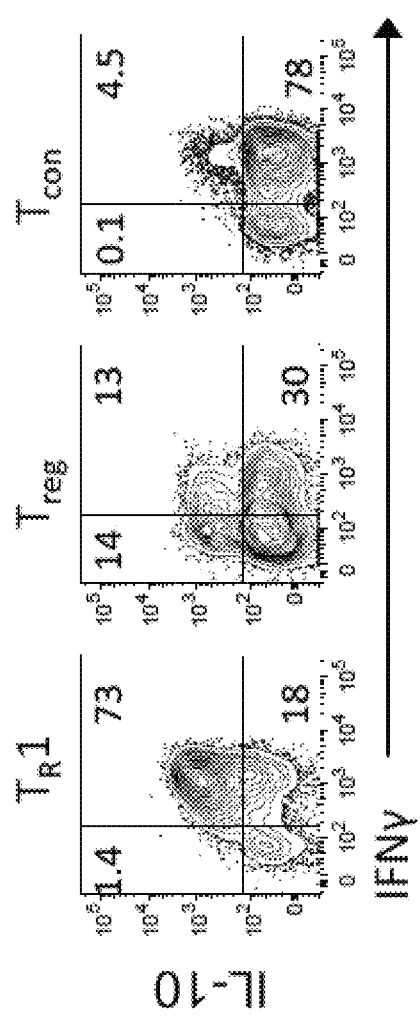

CD49b and LAG-3 co-expression can be used to identify $T_R1$ cells in models of colitis (9), however, their expression is insufficient to identify $T_R1$ cells after BMT (FIG. 10A). The present inventors therefore used Foxp3$^{RFPneg}$ and Il10$^{GFP+}$ as $T_R1$ cell markers. Thus defined $T_R1$ cells demonstrated high expression of CD122, α4β7, LAG-3, Ly6C and TIGIT, and low expression of CD25 and CD69 relative to other CD4$^+$ T cell subsets (FIG. 10B). Consistent with the $T_R1$ cell phenotype (3, 5, 9), Foxp3$^{RFPneg}$Il10$^{GFP+}$ $T_R1$ cells expressed high amounts of IL-10 and IFNγ but little $T_H2$ cytokines such as IL-4, IL-13 and IL-5, or $T_H17$ cytokines such as IL-17, IL-6 or GM-CSF (FIGS. 2A, 10C).

Figure 2C:
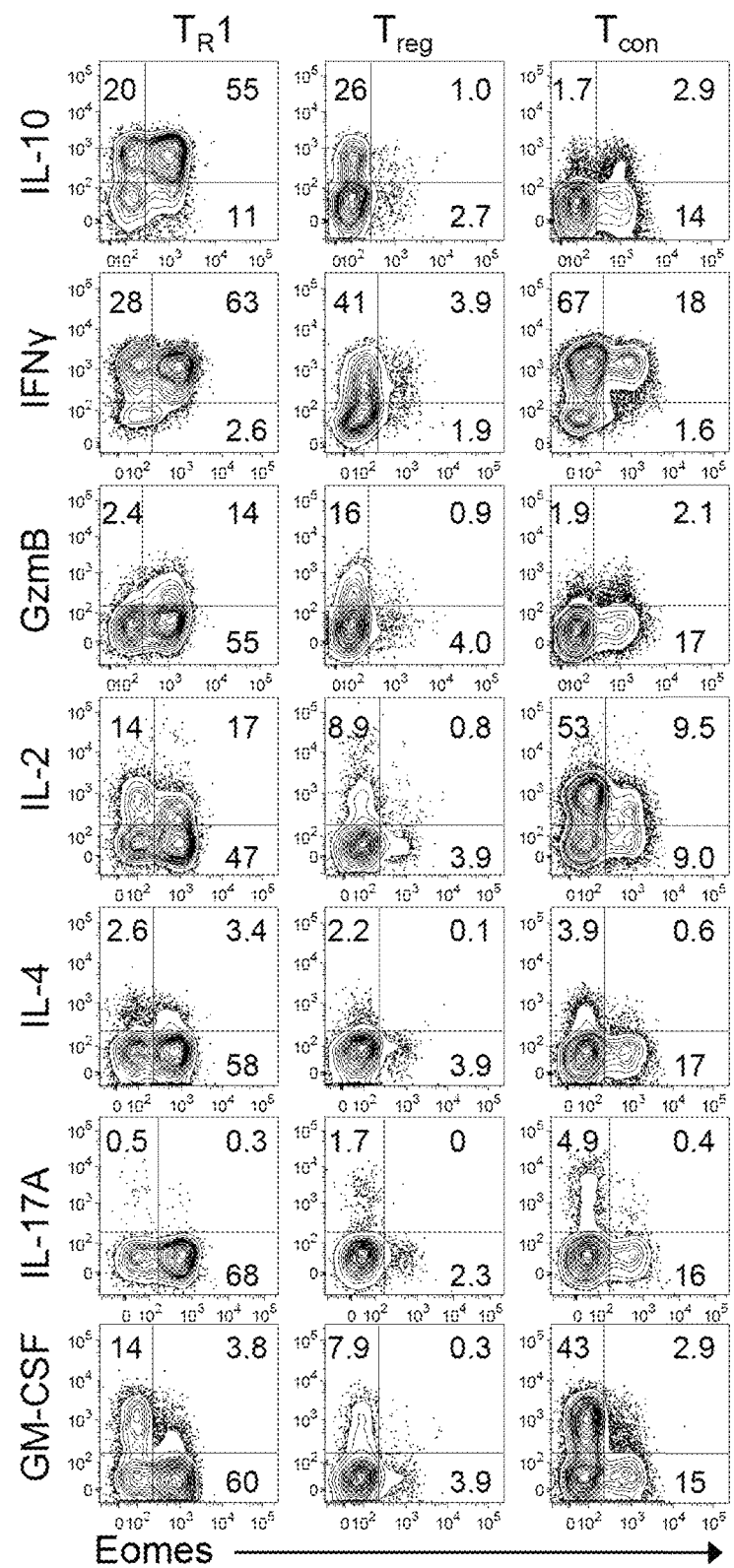

$T_R1$ cells have often been considered a terminally differentiated $T_H1$ cell subset programmed to limit aberrant inflammation (5, 13, 22). Indeed, $T_R1$ cells expressed high amounts of T-bet, the $T_H1$ determining transcription factor, but low amounts of GATA-3, BCL-6 and ROR-γt. Strikingly, when the present inventors analysed the expression of other transcription factors related to T cell differentiation, high Eomes expression was observed, which was largely restricted to $T_R1$ cells (FIGS. 28, 10D). Eomes expression tightly correlated with high expression of IL-10, IFNγ and granzyme B (GzmB) (FIG. 2C). In contrast, Eomes$^+$ $T_R1$ cells expressed low levels of IL-2, IL-17A and GM-CSF (FIG. 2C). Thus, $T_R1$ cells that develop during allogeneic BMT specifically express Eomes.

Eomes is Required for $T_R1$ Cell Differentiation

Figure 3A:
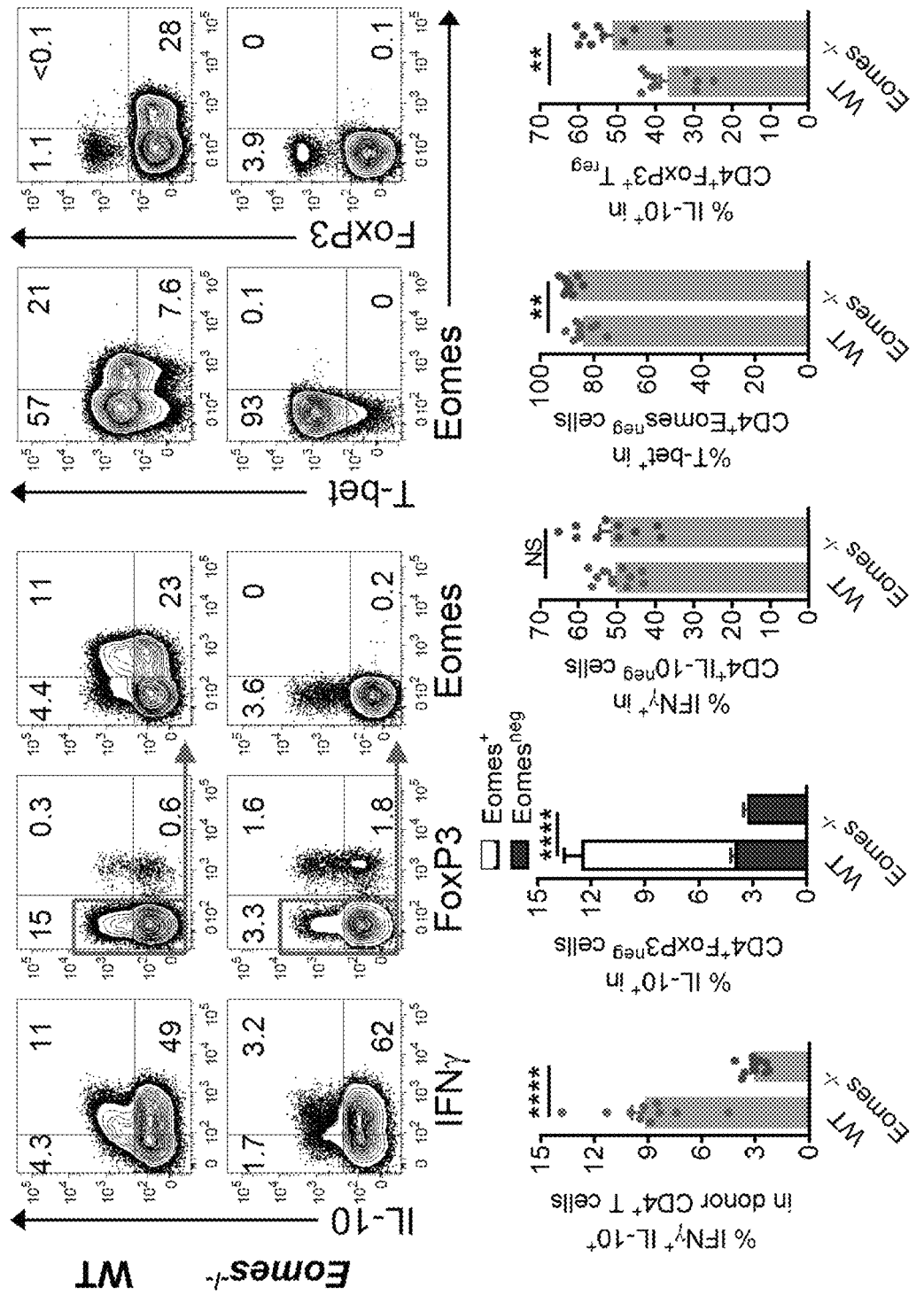
FIG. 3 is a graphical representation showing that Eomes is required for $T_R1$ cell differentiation. (A-D) B6D2F1 mice were transplanted with primary or retrovirally transduced (Mock-GFP or Eomes-GFP) CD4$^+$ T cells. (A) Expression of IL-10, IFNγ, FoxP3, Eomes and T-bet (Eomes$^+$IL-10$^+$: open bar; Eomes$^{neg}$IL-10$^+$: solid bar, n=10 per group) in recipients of WT or Eomes$^{-/-}$ CD4$^+$ T cells at d14 (n=10 per group). (B) Expression of IL-10, IFNγ, and Eomes in transduced WT or Eomes$^{-/-}$ CD4$^+$ T cells at 07 (n=8 per group) and (C) transcription of Il10 and related genes (data are from 4-5 pooled animals in triplicate reactions, representative of 2 independent experiments). (D) CD4$^+$ T cells or Foxp3$^{RFPneg}$Il10$^{GFP+}$ $T_R1$ cells were FACS sorted from spleen and liver at d14 (representative of 3 experiments). A schematic diagram of the mouse IL-10 promoter indicates Eomes binding sites upstream of the TSS with each sequence shown. Recruitment of Eomes to the Il10 promoter and control regions in CD4$^+$ T cells from $T_R1$ cells (data are from 30 pooled animals in triplicate reactions) and recruitment of RNA Pol II to the Il10 promoter in WT or Eomes$^{-/-}$ CD4$^+$ T cells (data are from 10 pooled animals in triplicate reactions). Data represents mean±SEM.
Figure 3B:
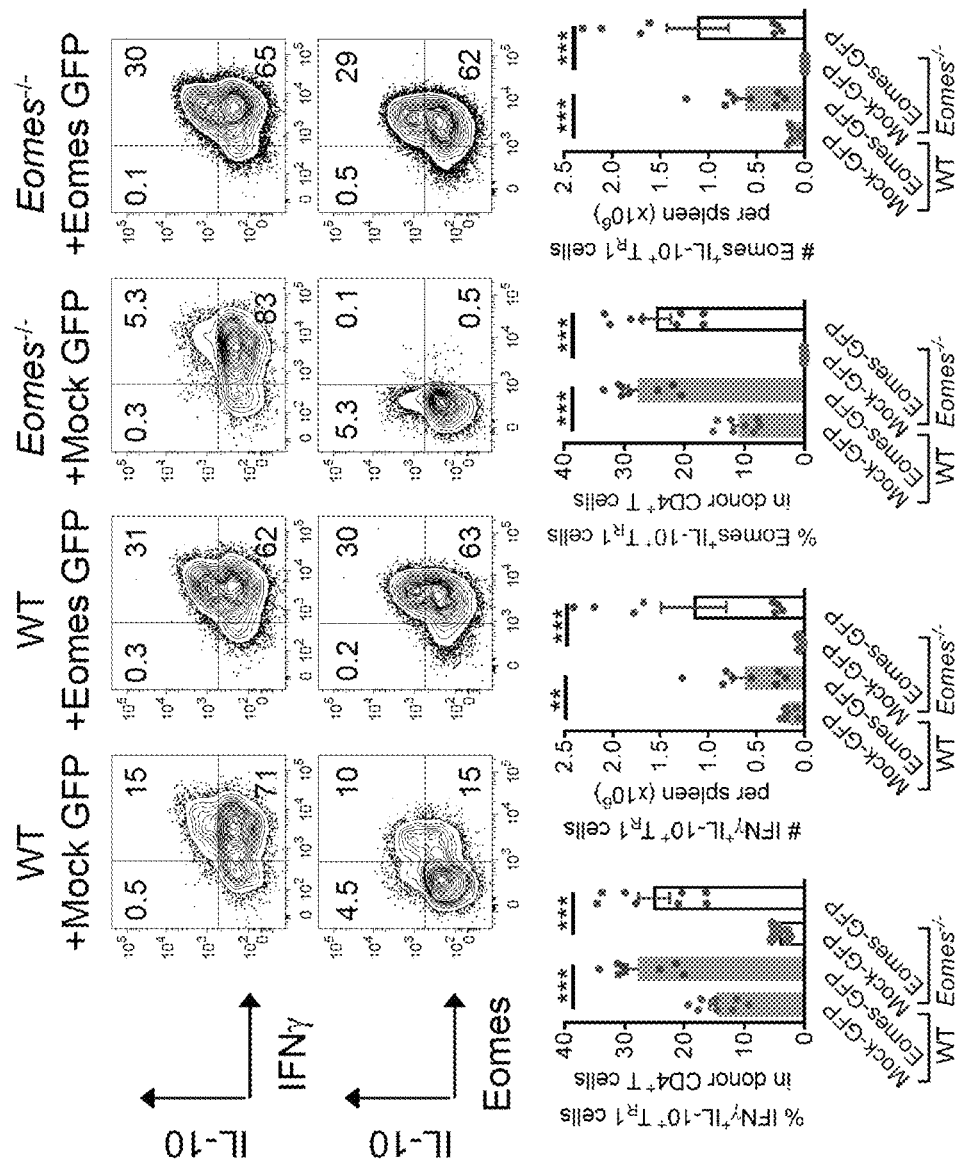
Figure 3C:
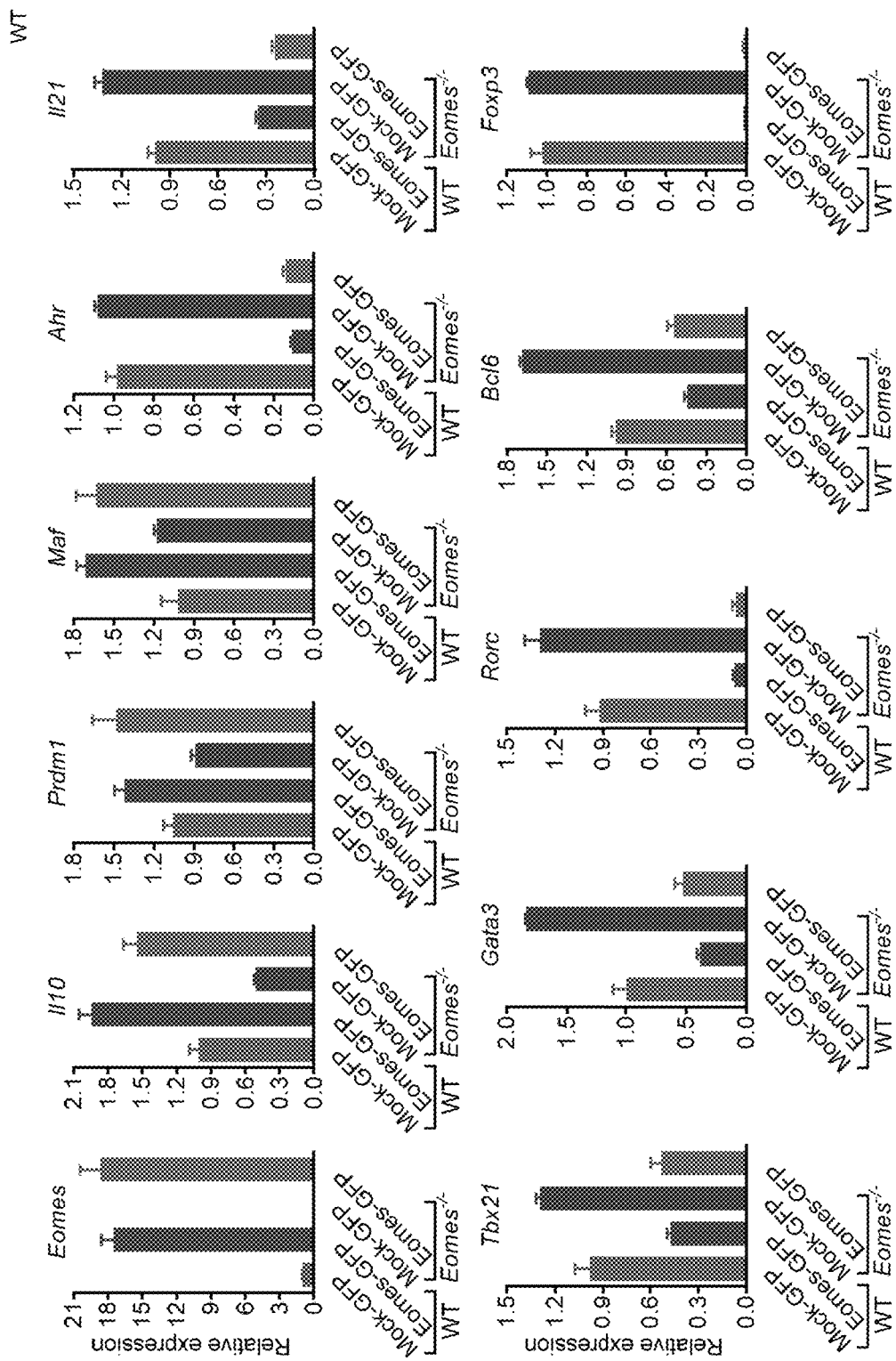
Figures 11A, 11B, 11C:
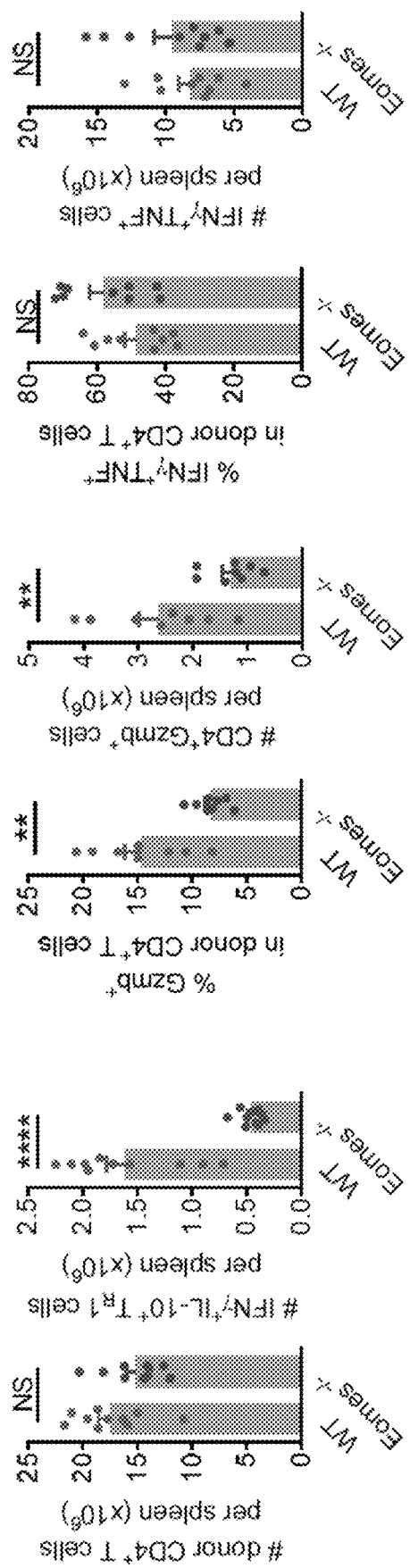
FIG. 11 is a graphical representation showing that Eomes is required for the development of $T_R1$ cells after BMT. (A-F) B6D2F1 recipients were transplanted with B6.WT or Eomes$^{-/-}$ CD4$^+$ T cells and spleens examined at d14 as described in FIG. 3A. (A) Absolute numbers of donor CD4$^+$ T cells and IFNγ$^+$IL-10$^+$ $T_R1$ cells (n=10 per group), (B-F) Frequencies and numbers of CD4$^+$Gzmb$^+$ cells (n=8 per group), IFNγ$^+$ TNF$^+$ cells (n=9 per group), IL-17A$^+$ cells (n=10 per group), IL-4$^+$ cells (n=9 per group) and CD4$^+$ FoxP3$^+$ $T_{reg}$ (n=10 per group). (G) B6.WT or Eomes$^{-/-}$ CD4$^+$ T cells were retrovirally transduced with Eomes and transplanted into B6D2F1 recipients. Expression of Gzmb, FoxP3, IL-4 and IL-17A in splenic CD4$^+$ T cells were examined at d7 as described in FIG. 3B. Data represents mean±S.E.M.
Figure 11F:
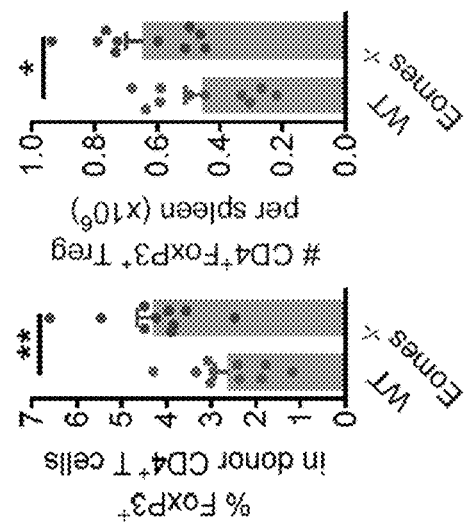
Figure 11E:
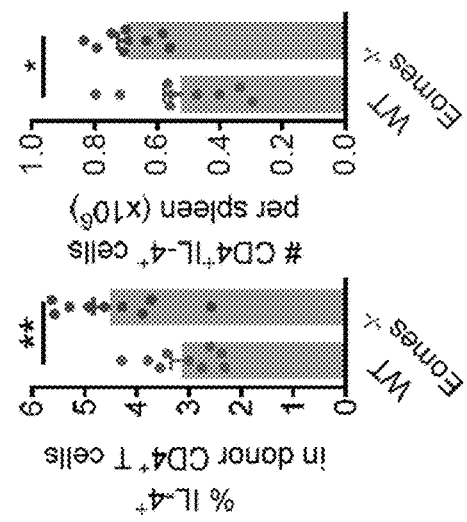
Figure 11D:
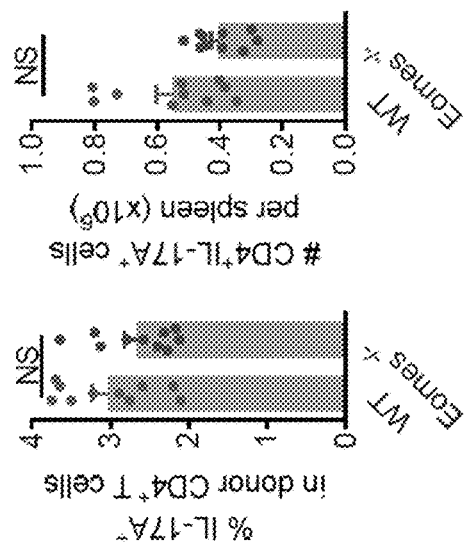
Figure 11G:
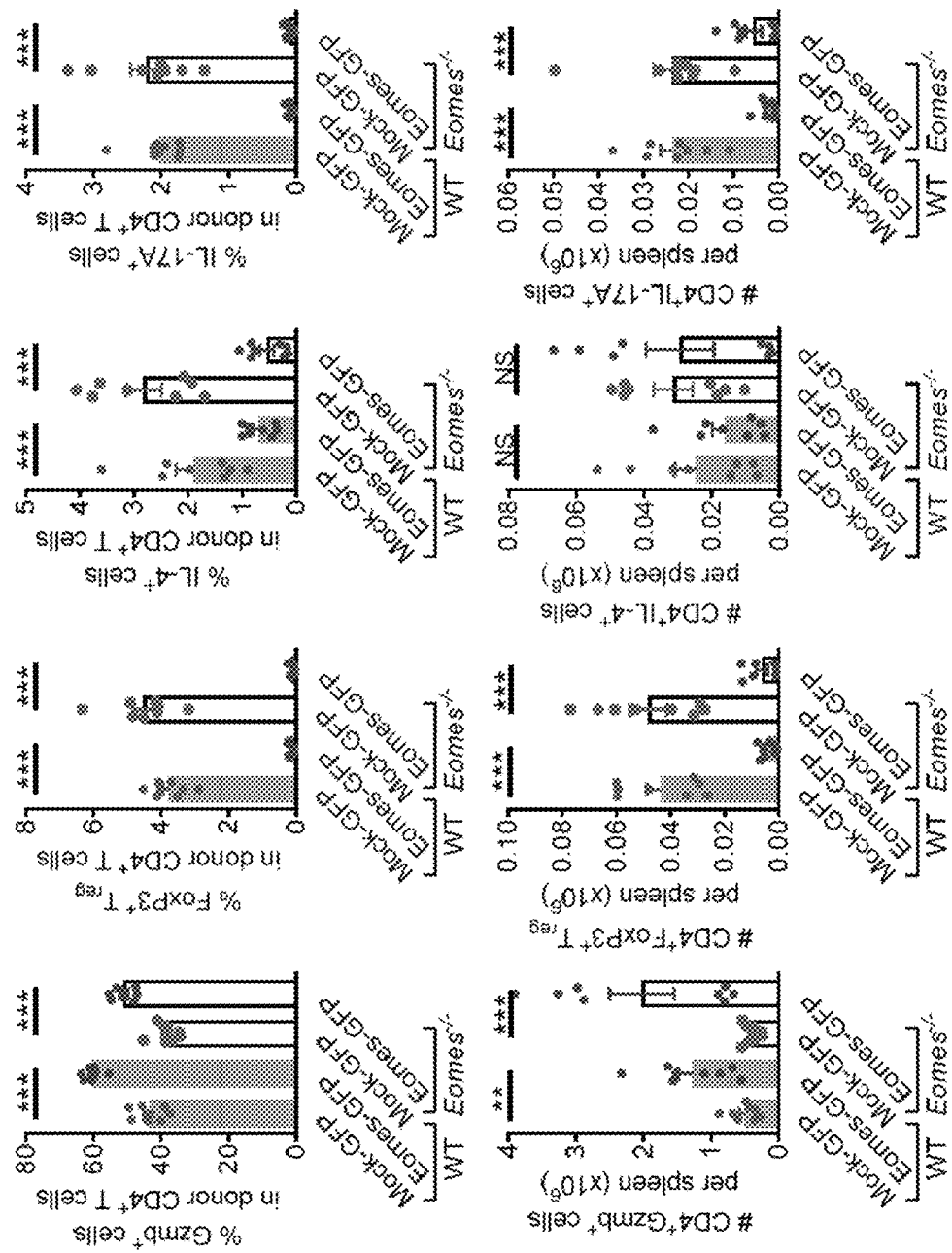

To test the role of Eomes in $T_R1$ cell development in vivo, the present inventors used CD4$^+$ T cells isolated from Eomes$^{fl/fl}$×Cd4-cre donor mice in allogeneic BMT. Strikingly, $T_R1$ cell generation was significantly reduced (by >70%) with decreased Gzmb expression in recipients of Eomes-deficient CD4$^+$ T cells (FIGS. 3A, 11A,B). Critically, the loss of Eomes did not impair the development of IL-10$^{neg}$IFNγ$^+$ or T-bet$^+$ $T_{con}$, IFNγ$^+$ TNF$^+$ $T_H1$, IL-17A$^+$ $T_H17$ cells or IL-10 expression by $T_{reg}$ cells but instead favoured the expression of IL-4 and FoxP3 (FIGS. 3A, 11B-F). To further elucidate the role of Eomes in the differentiation of $T_R1$ cells and transactivation of Il10, the present inventors transplanted donor WT or Eomes$^{-/-}$CD4$^+$ T cells which constitutively expressed Eomes after retroviral transduction. Strikingly, enforced expression of Eomes rescued the development of $T_R1$ cells from Eomes$^{-/-}$CD4$^+$ T cells after BMT and also promoted their development in WT cells (FIG. 3B). In addition, recombinant expression of Eomes promoted the expression of Gzmb whilst suppressing FoxP3, IL-4 and IL-17A expression (FIG. 11G). Furthermore, recombinant expression of Eomes upregulated the transcription of Il10 but suppressed that of other lineage defining transcription factors including Tbx21, Gata3, Rorc, Bcl6 and Foxp3 in addition to the $T_R1/T_H17$ related factors Ahr and Il21 (10, 23, 24)(FIG. 30.

Figure 12A:
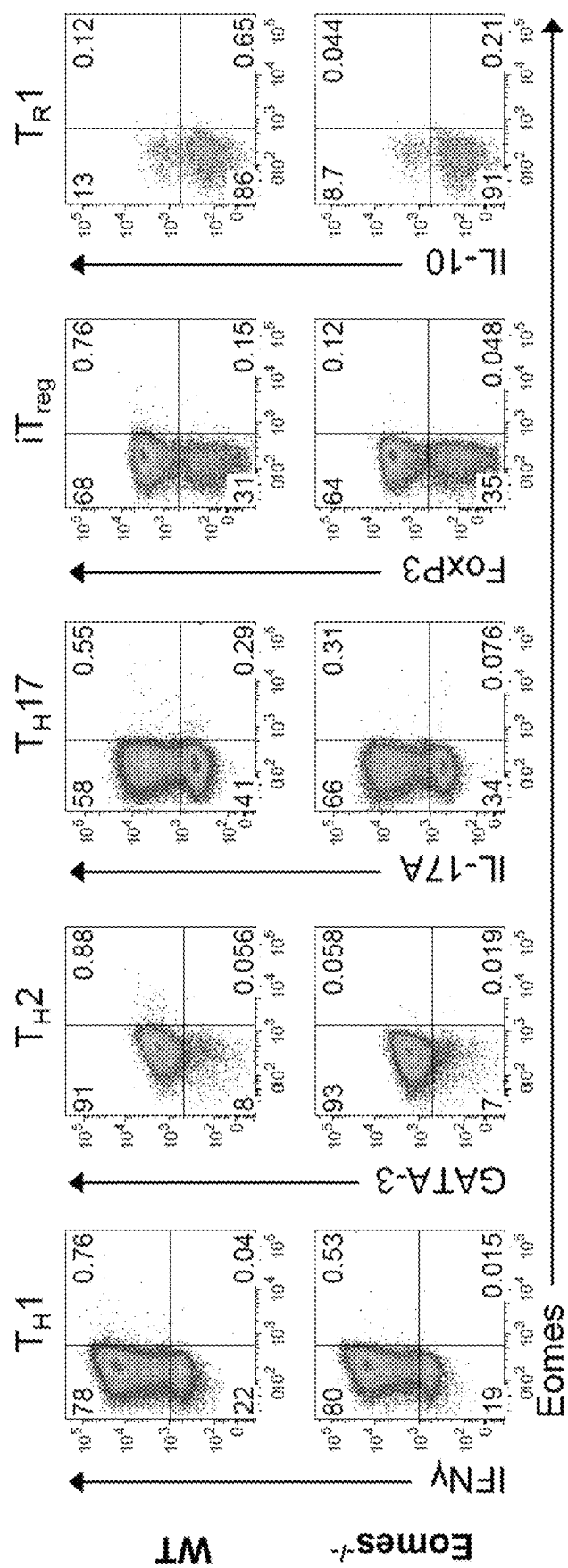
FIG. 12 is a graphical representation showing expression of Eomes during in vitro culture. CD4$^+$ T cells were cultured in vitro in polarizing conditions as described in Methods. (A) Expression of Eomes and lineage defining cytokines or transcription factors were determined by FACS on day 4 or day 7 and (8) expression of Eomes in $T_H1$, $T_H2$, $T_H17$ cells relative to $T_R1$ cells quantified with RT-PCR on day 4 (data are from triplicate reactions). Data represents mean t S.E.M.
Figure 12B:
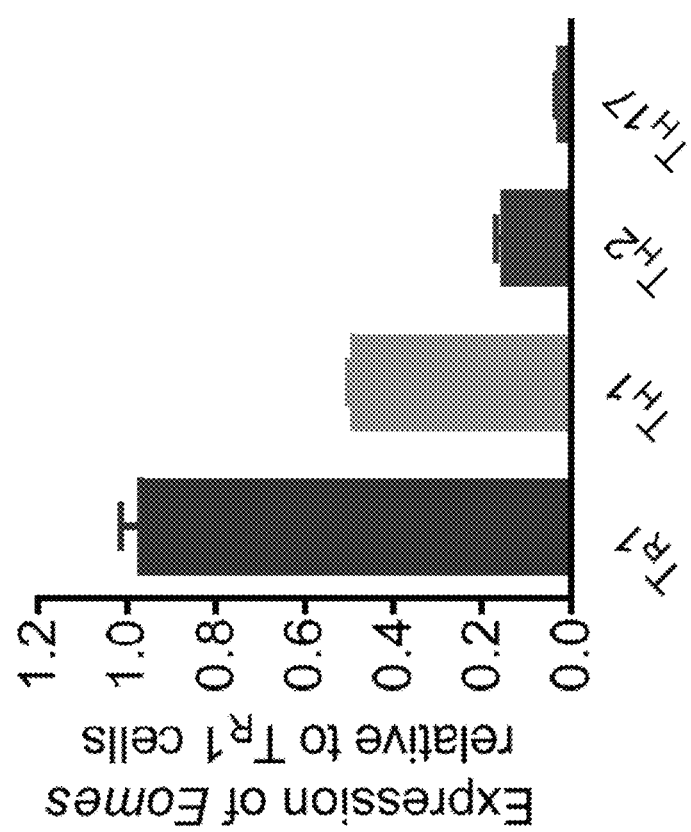
Figure 13A:
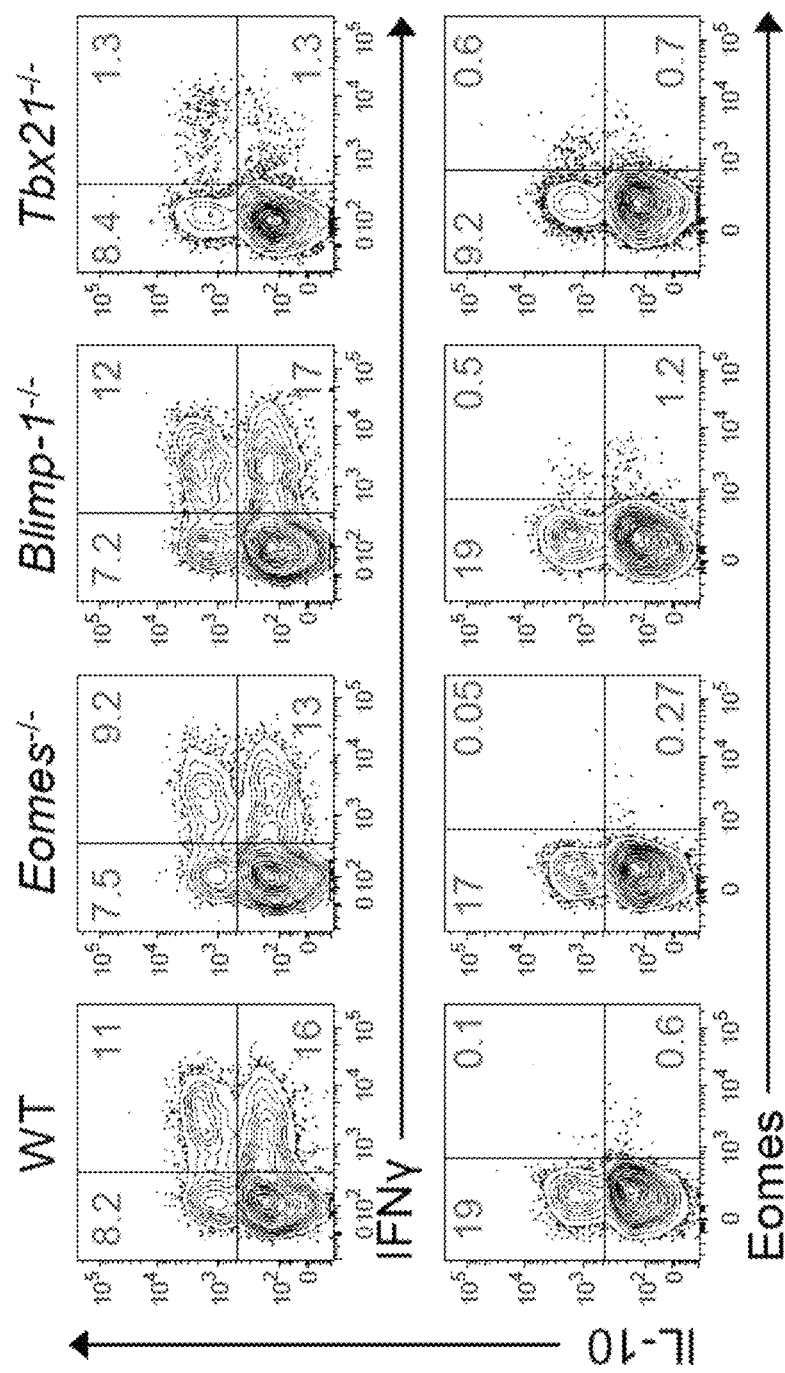
FIG. 13 is a graphical representation showing role of Eomes in the generation of $T_R1$ cells in vitro. (A) Generation of $T_R1$ cells at d6 after culture in WT or gene deficient CD4$^+$ T cells. (Band C) Retrovirally transduced (Mock-GFP or Eomes-GFP) CD4$^+$ T cells were cultured in the presence of IL-27 as described in the methods. (8) Expression of Eomes and cytokines at d5 after culture (from 3 experiments). (C) Gene expression profiles at d4 of culture quantified by RT-PCR (data are from quadruplicate reactions, representative of 2 experiments). Data represents mean±S.E.M.
Figure 13B:
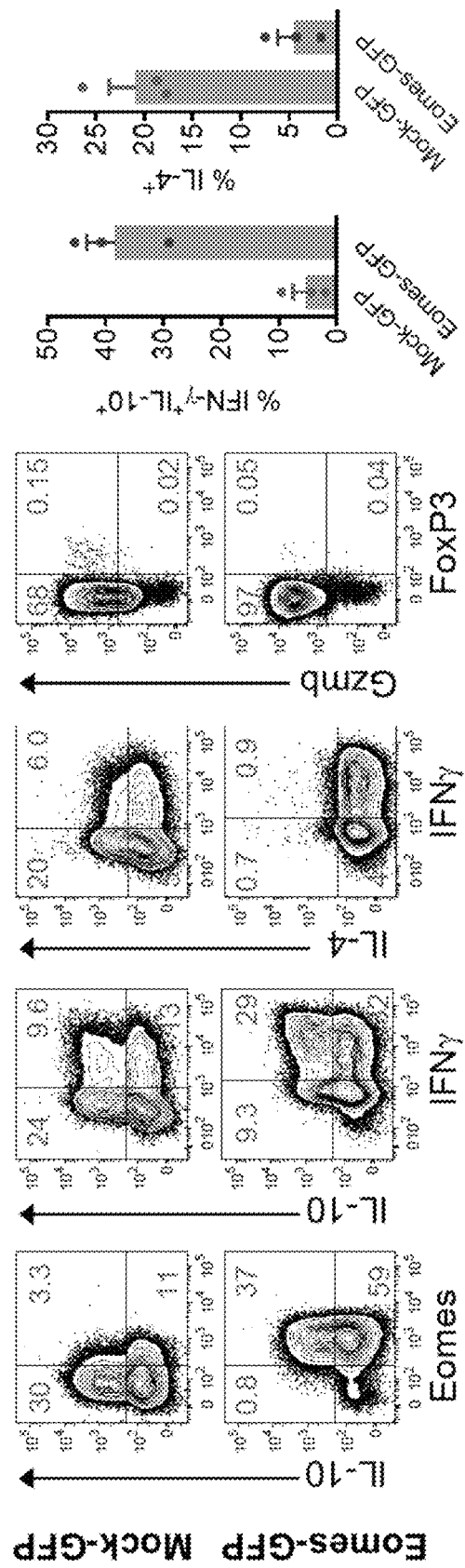
Figure 13C:
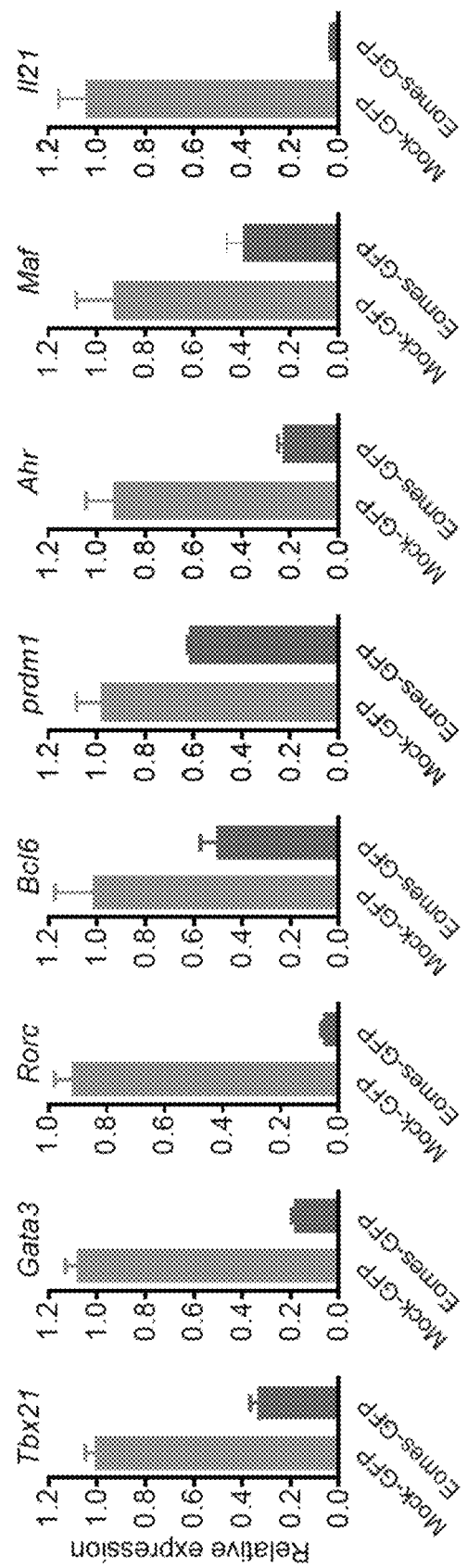

Notably, $T_R1$ cells generated in vitro in the presence of IL-27, a cytokine promoting $T_R1$ cell development (8, 11, 12), did not express Eomes protein, nor did $T_H1$, $T_H2$, $T_H17$, iT$_{reg}$ cells (FIG. 12A), indicating that short-term in vitro cultures do not replicate the conditions inducing $T_R1$ cells after BMT. Nevertheless, Eomes mRNA was higher in $T_R1$ than other T cell lineages in these cultures (FIG. 12B). Consistent with this observation, a defect in $T_R1$ differentiation was not observed in the absence of Eomes in these conditions (FIG. 13A). However, transduction of Eomes into CD4$^+$ T cells and subsequent re-stimulation in culture dramatically promoted the differentiation of IL-10$^+$IFNγ$^+$ $T_R1$ cells and the expression of granzyme B, while suppressing the expression of IL-4 and FoxP3 (FIG. 13B). Recombinant expression of Eomes also suppressed mRNA expression of transcription factors defining other $T_H$ lineages, including Tbx21, Gata3, Rorc and Bcl6 and other $T_R1/T_H17$ related factors, like Ahr, Maf and Il21 (FIG. 13C). Collectively, the present inventors show that Eomes is required for $T_R1$ differentiation and IL-10 secretion and repression of alternative fate differentiation Eomes Directly Regulates IL-10 Expression in $T_R1$ Cells To understand the mechanism by which Eomes regulates $T_R1$ cell differentiation, chromatin immunoprecipitation (ChIP) assays was performed on sort purified $T_R1$ cells or CD4$^+$ T cells 14 days after BMT. This demonstrated that Eomes is bound to multiple sites within 2 kb upstream of the transcription start site (TSS) of the Il10 gene (FIG. 30). The binding of Eomes to the Il10 promoter was similar to that observed in the Ifnγ promoter, suggesting that Eomes regulates expression of both Il10 and Ifnγ directly. Consistent with this concept, the recruitment of RNA polymerase II to the Il10 promoter, an indicator of transcriptional activity, was reduced in Eomes-deficient CD4$^+$ T cells (FIG. 30).

Eomes$^+$ $T_R1$ Cells are Dependent on BLIMP-1, IL-27 AND IL-10

Figure 4A:
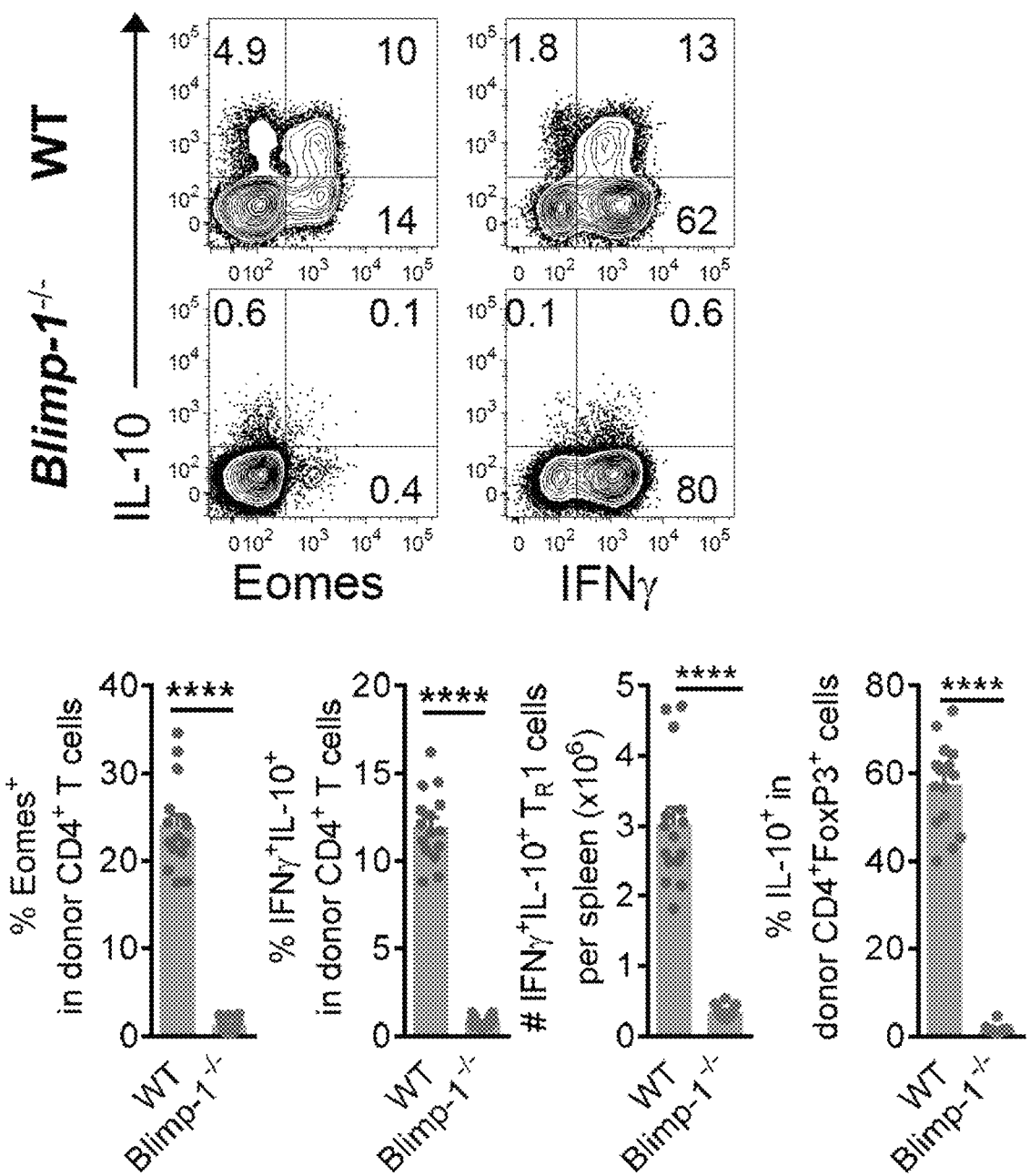
FIG. 4 is a graphical representation showing that Eomes$^+$ $T_R1$ cells are dependent on Blimp-1, IL-27 and IL-10. (A-F) B6D2F1 mice were transplanted with primary or retrovirally transduced (Mock-GFP or Eomes-GFP) CD4$^+$ T cells and spleen examined after BMT. (A) Expression of Eomes, IL-10 and IFNγ in WT or Blimp-1$^{-/-}$ CD4$^+$ T cells at d14 (n=14-15 per group). (B) Expression of Eomes, IL-10 and IFNγ (n=18, 17 for WT; n=13, 14 for Blimp-1$^{-/-}$) in transduced CD4$^+$ T cells at d7-10. (C) Recruitment of Eomes to I/10 promoter in transduced CD4$^+$ T cells (WT or Blimp-1$^{-/-}$) at d10 (data are from 4 animals in duplicate or triplicate reactions). (D) Expression of T-bet, Eomes and IL-10 in WT or Il27r$^{-/-}$CD4$^+$ T cells at d14 (n=10 per group). (E) Expression of Eomes and IFNγ$^+$IL-10$^+$ $T_R1$ cells in WT or Il10r$^{-/-}$ CD4$^+$ T cells at d14 (n=10 per group). (F) Expression of Eomes and IL-10 (Eomes$^+$IL-10$^+$: open bar; Eomes$^+$IL-10$^{neg}$: solid bar) in CD4$^+$ T cells in recipients of WT or Il10$^{-/-}$CD4$^+$CD25$^{neg}$ T cells at d14 (n=10-11 per group). Data represents mean±SEM.
Figure 4B:
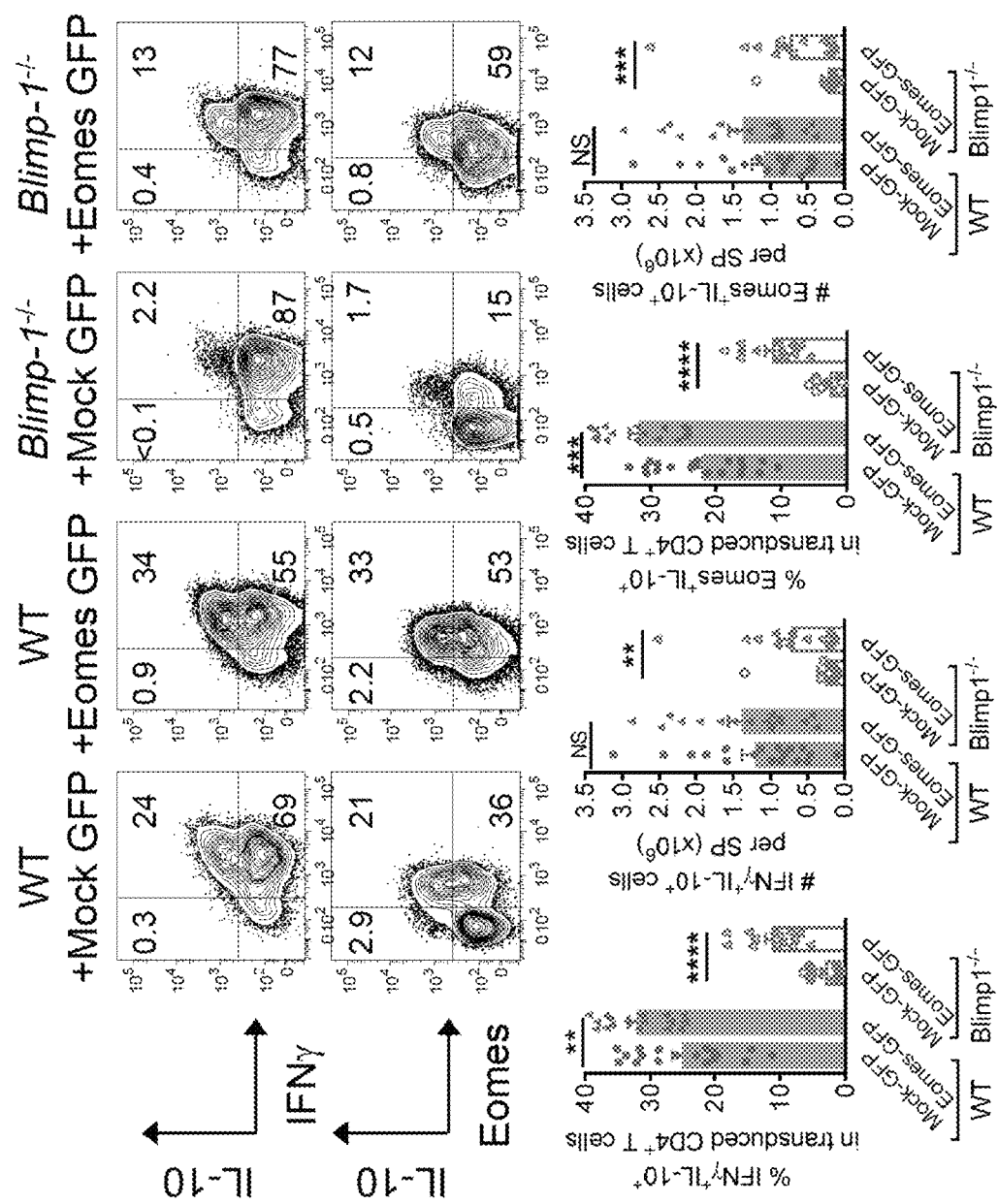
Figure 4C:
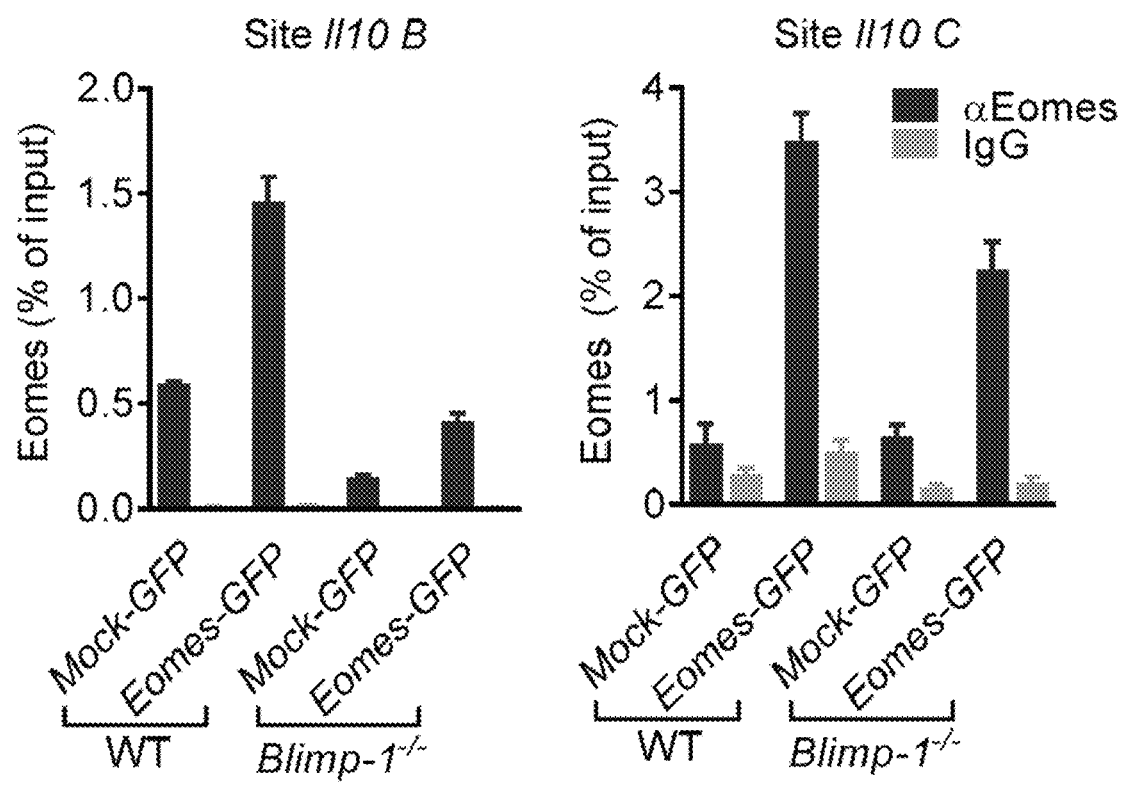
Figure 14D:
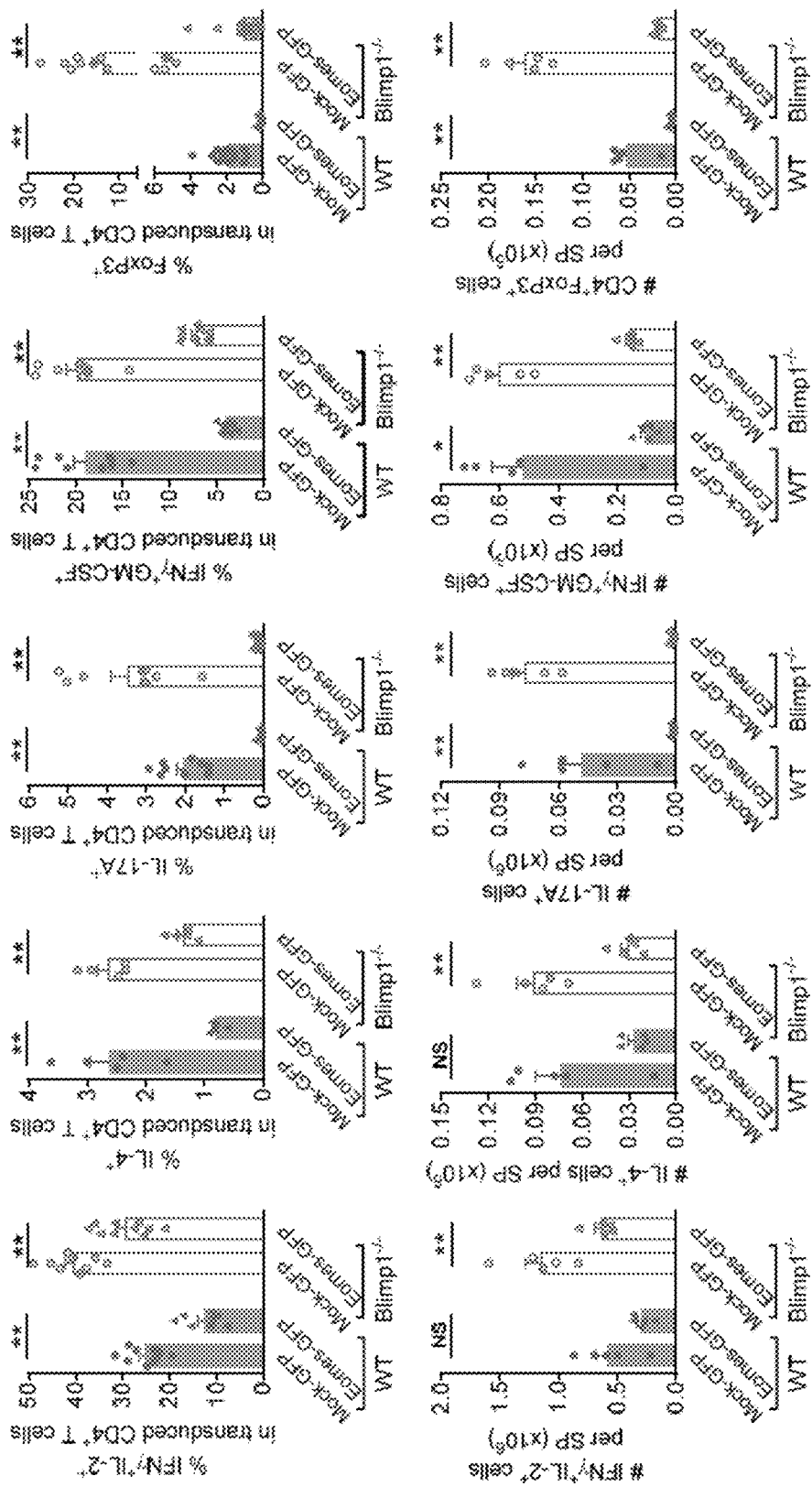
FIG. 14 is a graphical representation showing that Eomes$^+$ $T_R1$ cells are dependent on Blimp-1, IL-27 and IL-10. (A and B) B6D2F1 mice were transplanted with WT or gene deficient CD4$^+$ T cells with analysis of spleen at d14. (A) Expression of IL-10 versus Blimp-1 (GFP is driven off the promoter of Prdm1) in CD4$^+$ T cells (representative of 2 experiments). (8) Expression of T-bet and Eomes in donor CD4+ T cells in recipients of WT or Blimp-1−/− T cells. (C and D) B6D2F1 recipients were transplanted with WT or Blimp-1−/− CD4+ T cells that were transduced with empty (Mock-GFP) or Eomes (Eomes-GFP) retrovirus and spleens examined at d7-10 after BMT. (C) Frequencies and number of Granzyme B (n=5 per group) at d7. (D) Frequencies of IL-2 (n=9-10 per group), IL-4 (n=5 per group), IL-17A (n=9-10 per group), GM-CSF (n=9 per group) and FoxP3 (n=18, 17 for WT; n=13, 14 for Blimp-1−/−) with numbers from one representative experiment (n=5 per group). (E and F) B6D2F1 mice were transplanted with WT or gene deficient CD4+ T cells with analysis of spleen at d14. (E) Expression of $T_R1$ cells, IFNγ and IL-10 in recipients of WT or Il27r−/− CD4+ T cells (n=10 per group). (i) Number of donor CD4+ T cells and frequencies of T-bet in recipients of WT or Il10r−/− CD4+ T cells (n=10 per group). Data represents mean±S.E.M.

Blimp-1 is a well-defined transcriptional promoter of IL-10 in CD4$^+$ conventional T and T$_{reg}$ cells (6, 11, 21). Consistent with this notion, after BMT IL-10 production in all CD4$^+$ T cells was confined to Blimp-1 expressing cells (FIG. 14A). Critically, conditional ablation of Blimp-1 (Prdm1$^{fl/fl}$×Lck-cre) in donor T cells resulted in a near complete loss of both IL-10 and Eomes expression in CD4$^+$ T cells, demonstrating a near complete lack of $T_R1$ cells (FIG. 4A) while the expression of T-bet was not impaired (FIG. 14B). To elucidate the relative contribution of Eomes and Blimp-1 to the expression of IL-10, Eomes-transduced WT or Blimp-1$^{-/-}$ CD4$^+$ T cells were transferred into allogenic BMT recipients. Consistent with a critical role of Eomes in the differentiation of $T_R1$ cells, recombinant expression of Eomes in Blimp-1-deficient CD4$^+$ T cells partially rescued their defective expression of IL-10 and GzmB and suppressed the expression of IL-2, IL-4, IL-17A, GM-CSF and FoxP3 after BMT (FIGS. 4B, 14C,D). Furthermore, Eomes transduction enhanced the recruitment of Eomes to the Il10 promoter regions both in WT and Blimp1$^{-/-}$ CD4 T cells (FIG. 4C).

Figure 4D:
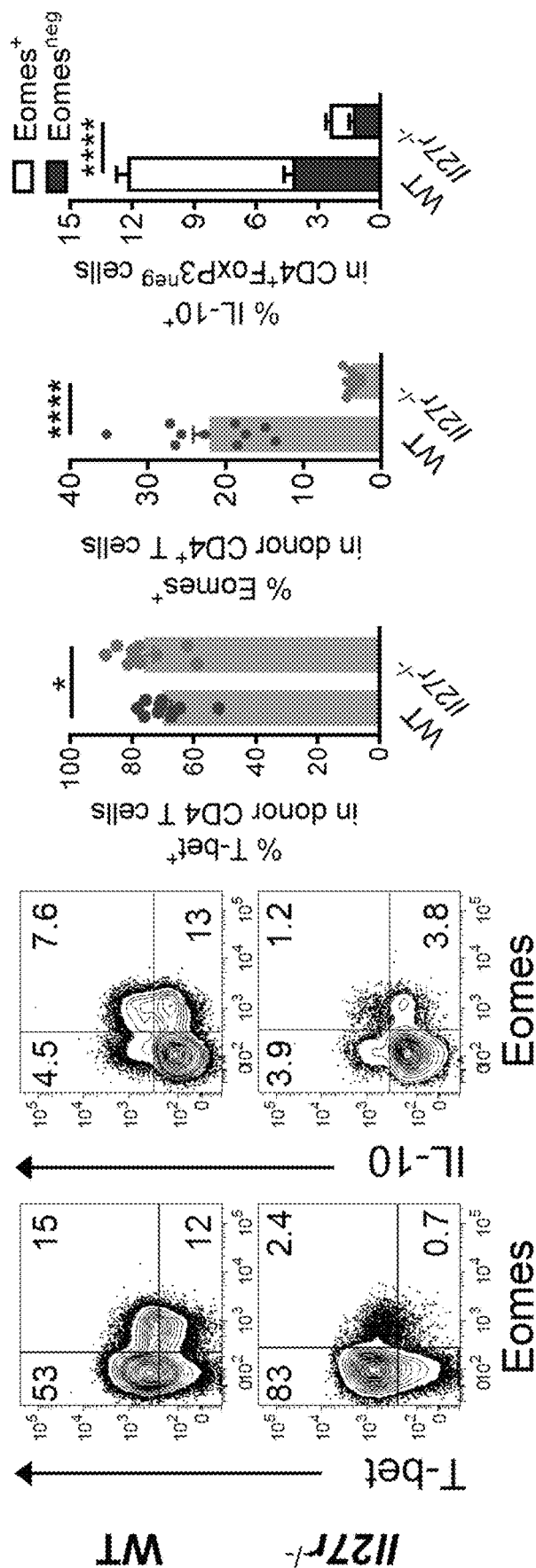
Figures 14E, 14F:
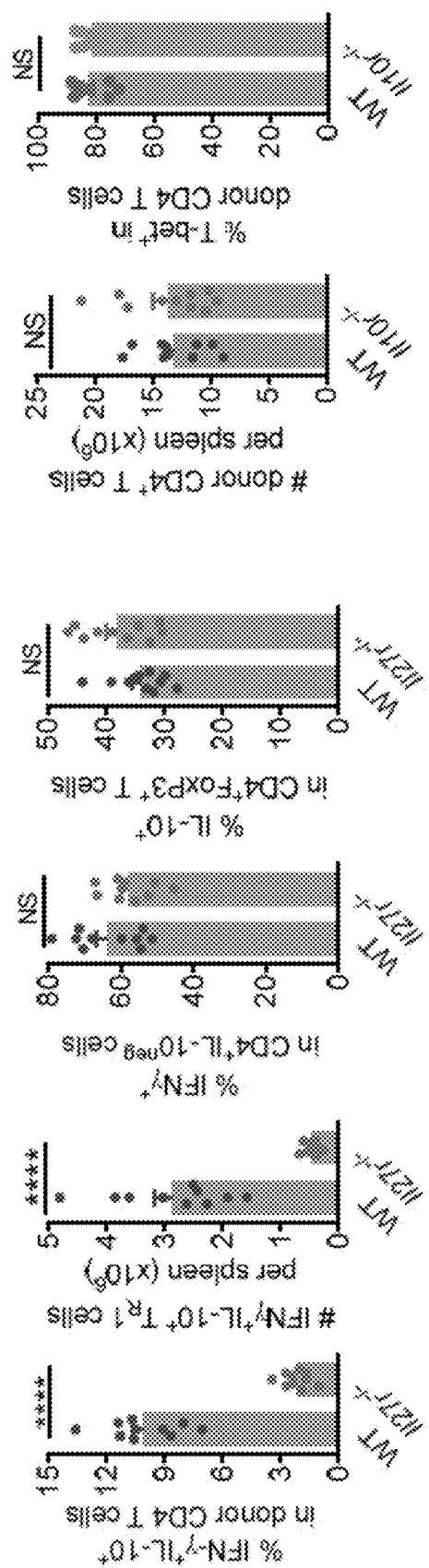

To test the role of IL-27 in the induction of Eomes$^+$ $T_R1$ cells after BMT, the present inventors transplanted Il27r$^{-/-}$ CD4$^+$ T cells. Consistent with an important role for IL-27 in $T_R1$ induction, substantially decreased expression of Eomes was found in Il27r$^{-/-}$ CD4$^+$ T cells, and $T_R1$ cells were reduced by >80% (FIGS. 4D, 14). In contrast, T-bet expression was increased in the absence of IL-27 signalling (FIG. 40), and the development of CD4$^+$IL-10$^{neg}$IFNγ$^+$ conventional $T_H1$ cells or IL-10 production capabilities of T$_{reg}$ cells were not impaired (FIG. 14).

Figure 4F:
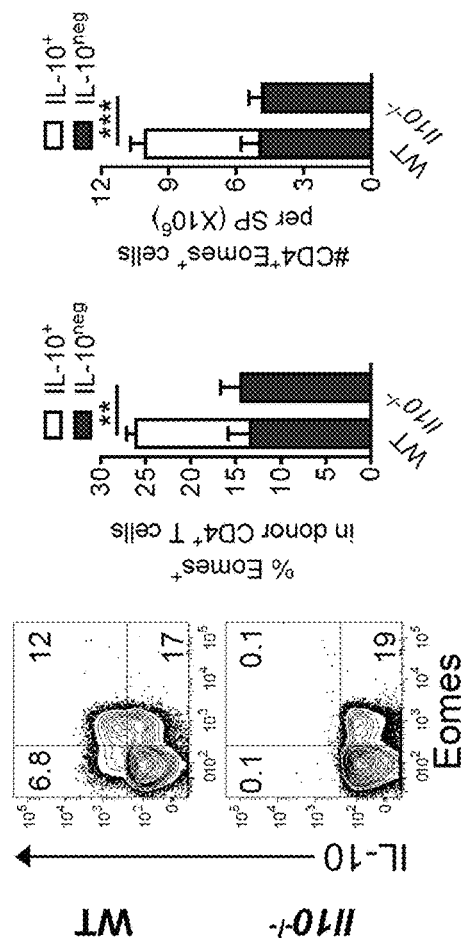
Figure 4E:
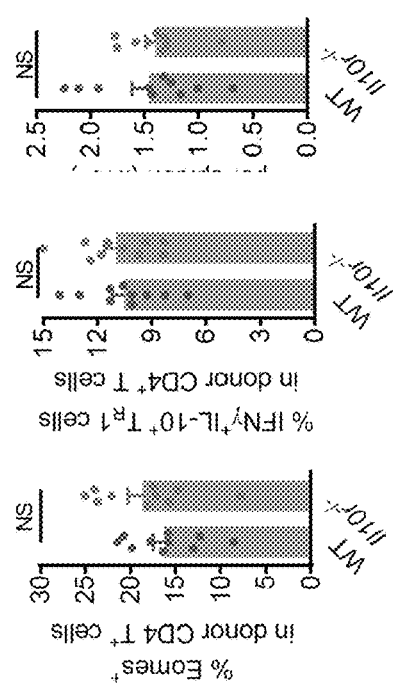

The present inventors next tested whether the differentiation of Eomes$^+$ $T_R1$ cells was dependent on IL-10 itself. The expression of Eomes, $T_R1$ cells as well as T-bet was not reduced in Il10r-deficient CD4$^+$ T cells (Il10r$^{fl/fl}$×Lck-cre) after BMT (FIGS. 4E, 14F), indicating that IL-10 signalling in T cells was not required for $T_R1$ cell differentiation. However, when Il10$^{-/-}$ CD4$^+$CD25$^{neg}$ T cells were transplanted, Eomes$^+$ cells were reduced (FIG. 4F), in line with the notion that IL-10 promotes $T_R1$ cell differentiation indirectly (22, 25). In summary, Eomes expression in $T_R1$ cells is downstream of IL-27 and Blimp-1 bit does not depend on T cell intrinsic IL-10 signalling.

Eomes$^+$ $T_R1$ Cells are Critical for Prevention of GVHD

Figure 5B:
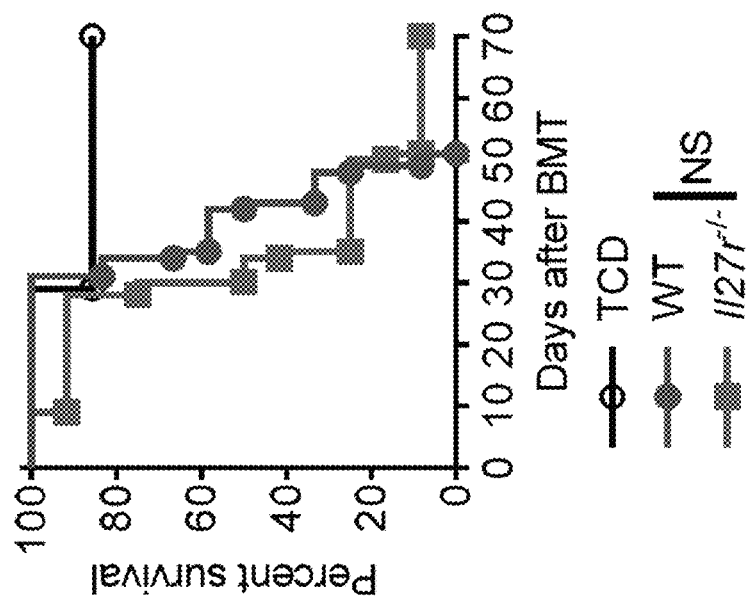
FIG. 5 is a graphical representation showing attenuation of GVHD by Eomes$^+$ $T_R1$ cells. (A-E) B6D2F1 recipients were transplanted with CD4$^+$ T cells and survival or histopathology examined. (A) Survival of recipients of WT or Blimp-1$^{-/-}$ CD4$^+$ T cells (2×10$^6$ per mouse) (n=11 per T cell group, n=7 in TCD, 2 experiments). (B) Survival of recipients of WT or Il27r$^{-/-}$ CD4$^+$CD25$^{neg}$ T cells (2×10$^6$ per mouse) (n=12 per T cell group, n=7 in TCD; 2 experiments). (C and D) Histology in recipients of (C) WT versus Il10$^{-/-}$ or (D) WT versus Il10$^{fl/fl}$×Lck-cre CD4$^+$CD25$^{neg}$ T cells (1×10⁶ per mouse) at d28 (n=6 per T cell group, n=3 in TCD group). (L) Survival of recipients of WT or Eomes$^{-/-}$ CD4$^+$CD25$^{neg}$ T cells (1×10⁶ per mouse) (n=12 per T cell group, n=7 in TCD; 2 experiments). Histology represents mean±SEM.
Figure 5A:
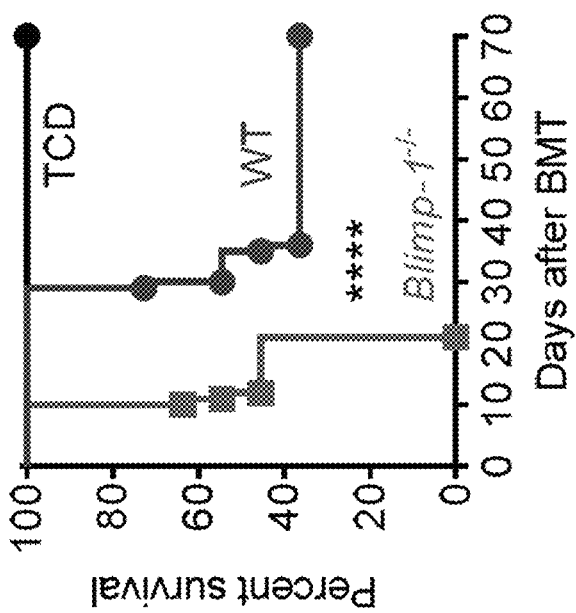
Figure 5C:
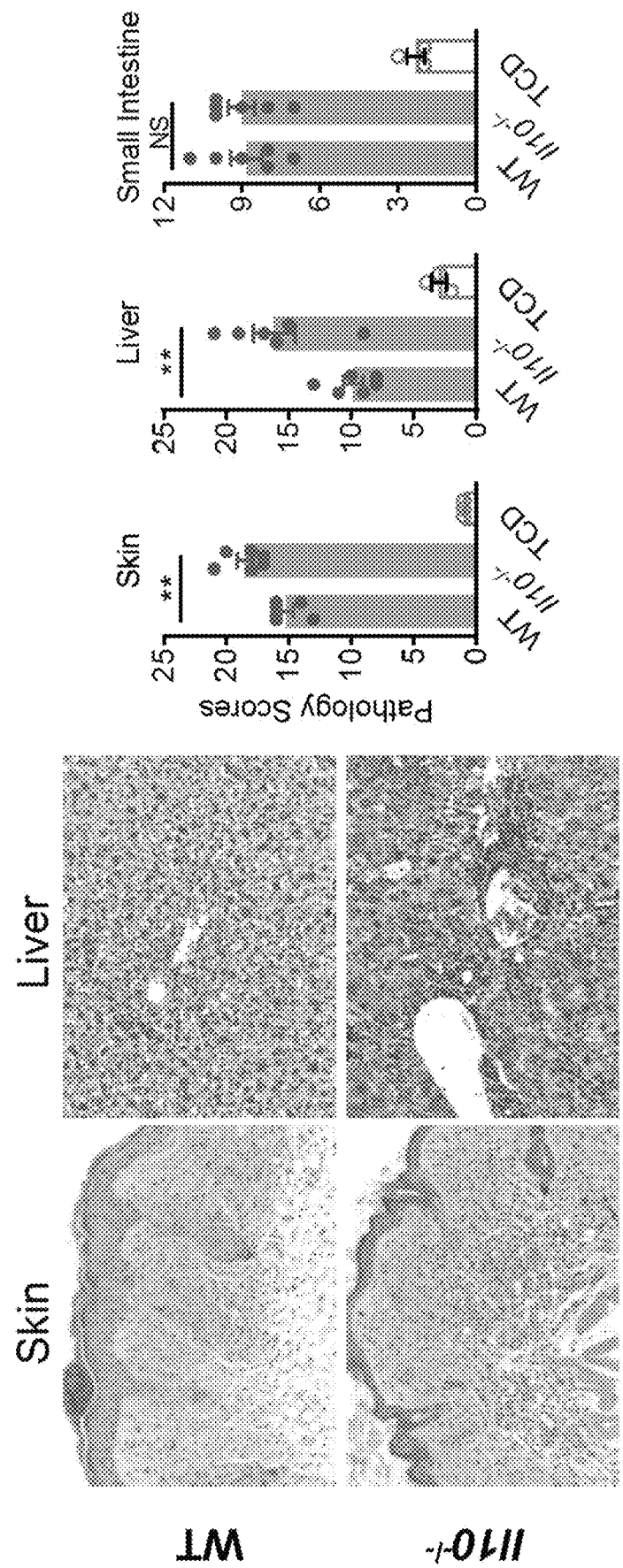
Figure 5E:
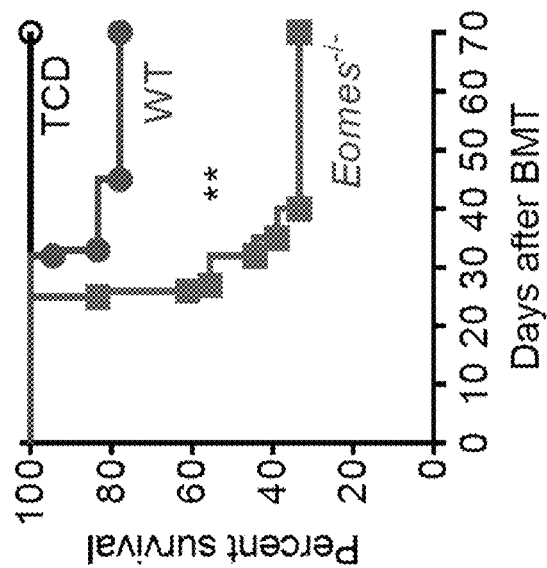
Figure 5D:
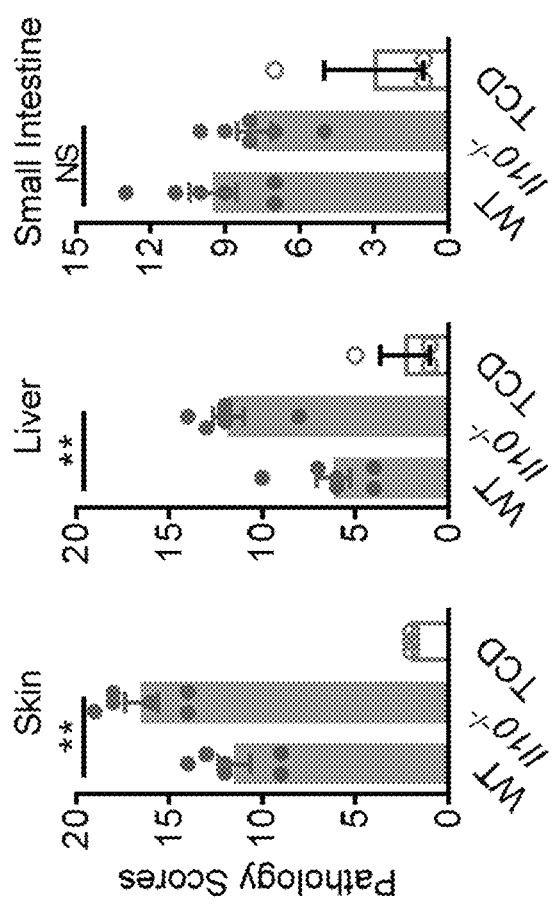

The present inventors next examined whether Blimp-1-deficient and Il27r-deficient CD4$^+$ T cells would exacerbate GVHD due to impaired expression of Eomes and $T_R1$ cells. Whilst Blimp1 deletion exacerbated GVHD (FIG. 5A), IL-27R deletion did not (FIG. 5B). Of note, T$_{reg}$ cells were increased and their IL-10 production was intact in recipients of Il27r$^{-/-}$ CD4$^+$ T cells (FIGS. 14E, 15A), consistent with compensatory regulatory pathways in the absence of $T_R1$. In contrast, Il10$^{-/-}$CD4$^+$ T cells sustain comparable expression of Eomes in conventional T cells and T$_{reg}$ cells (FIGS. 4F, 15A) after BMT and thus reflect a more relevant model to define the regulatory function of $T_R1$ cells in vivo. Consistent with the reduced frequency of $T_R1$ cells, enhanced GVHD was observed in the skin and liver in recipients of Il10$^{-/-}$ CD4$^+$CD25$^{neg}$ T cells (FIG. 5C). These findings were confirmed by transplanting Il10$^{fl/fl}$×Lck-cre CD4$^+$CD25$^{neg}$ T cells, which also led to exacerbated GVHD in the absence of IL-10 producing $T_R1$ cells (FIG. 5D). Lastly, Eomes$^{-/-}$CD4$^+$CD25$^{neg}$ T cells also resulted in increased GVHD, further confirming the important regulatory role of Eomes$^+$ $T_R1$ cells after BMT (FIG. 5E).

Eomes and T-Bet Cooperates to Generate $T_R1$ Cells

Figure 6B:
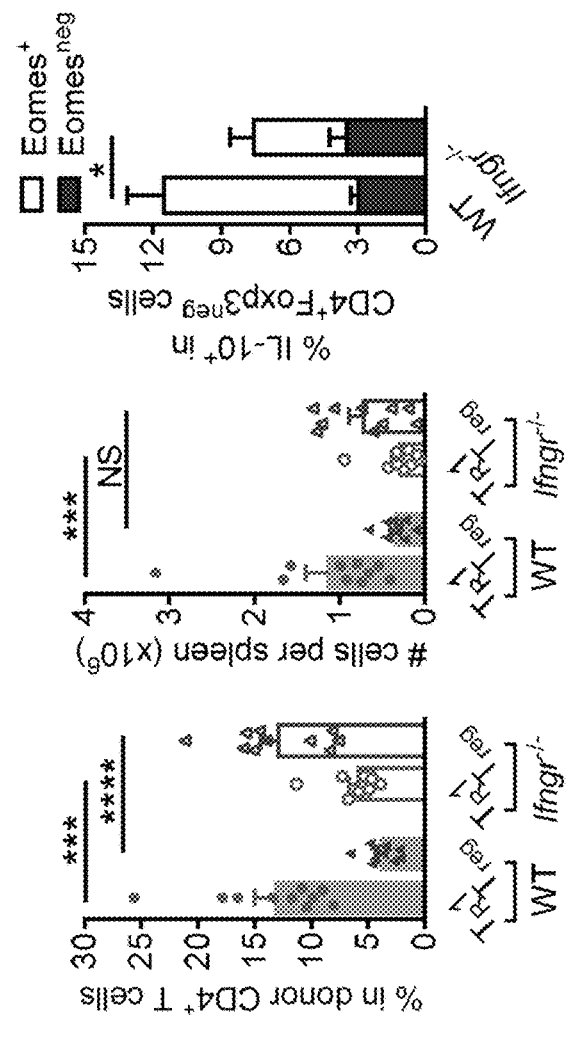
FIG. 6 is a graphical representation showing that Eomes and T-bet jointly regulate $T_R1$ cell development. (A and B) B6.WT or B6.Ifngr$^{-/-}$CD3$^+$ T cells were transplanted into B6D2F1 mice and splenic CD4$^+$ T cells examined at d14. (A) Representative plots show expression of T-bet and Eomes and (8) frequencies of $T_R1$ and $T_{reg}$ cells and expression of IL-10 and Eomes (n=10 per group). (C) B6.Il10$^{GFP}$ (Foxp3$^{RFP}$ CD3$^+$ T cells were transplanted into B6D2F1 mice receiving αIFNγ or control mAb and splenic CD4$^+$ T cells examined at d12 (n=5 per group). Frequencies of $T_R1$ and $T_{reg}$ cells and expression of Eomes and IL-10 are shown. (D) B6D2F1 mice were transplanted with WT or Tbx21$^{-/-}$ CD4$^+$ T cells and expression of transcription factors and cytokines in splenic CD4$^+$ T cells at d12 shown (n=10 per group). (E) B6D2F1 mice were transplanted with retrovirally (Mock-GFP or Eomes-GFP) transduced WT or Tbx21$^{-/-}$ CD4$^+$ T cells and expression of IL-10, IFNγ, IL-4 and GATA-3 in splenic CD4$^+$ T cells at d7 shown (n=8 per group). (f) Co-expression of T-bet and Eomes in CD4$^+$ T cells over time (representative of at least 2 experiments). (G) Splenic CD4$^+$ T cells from naïve mice FACS sorted to 4 subsets based on Il10$^{GFP}$ and Foxp3$^{RFP}$ expression and T-bet and Eomes evaluated (representative of 2 experiments). Data represents mean±SEM.
Figure 6A:
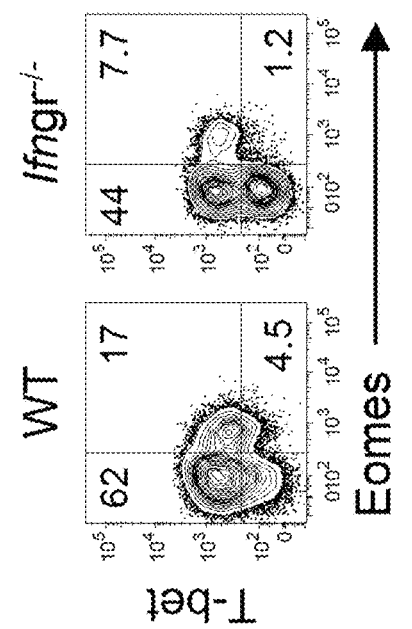
Figure 6C:
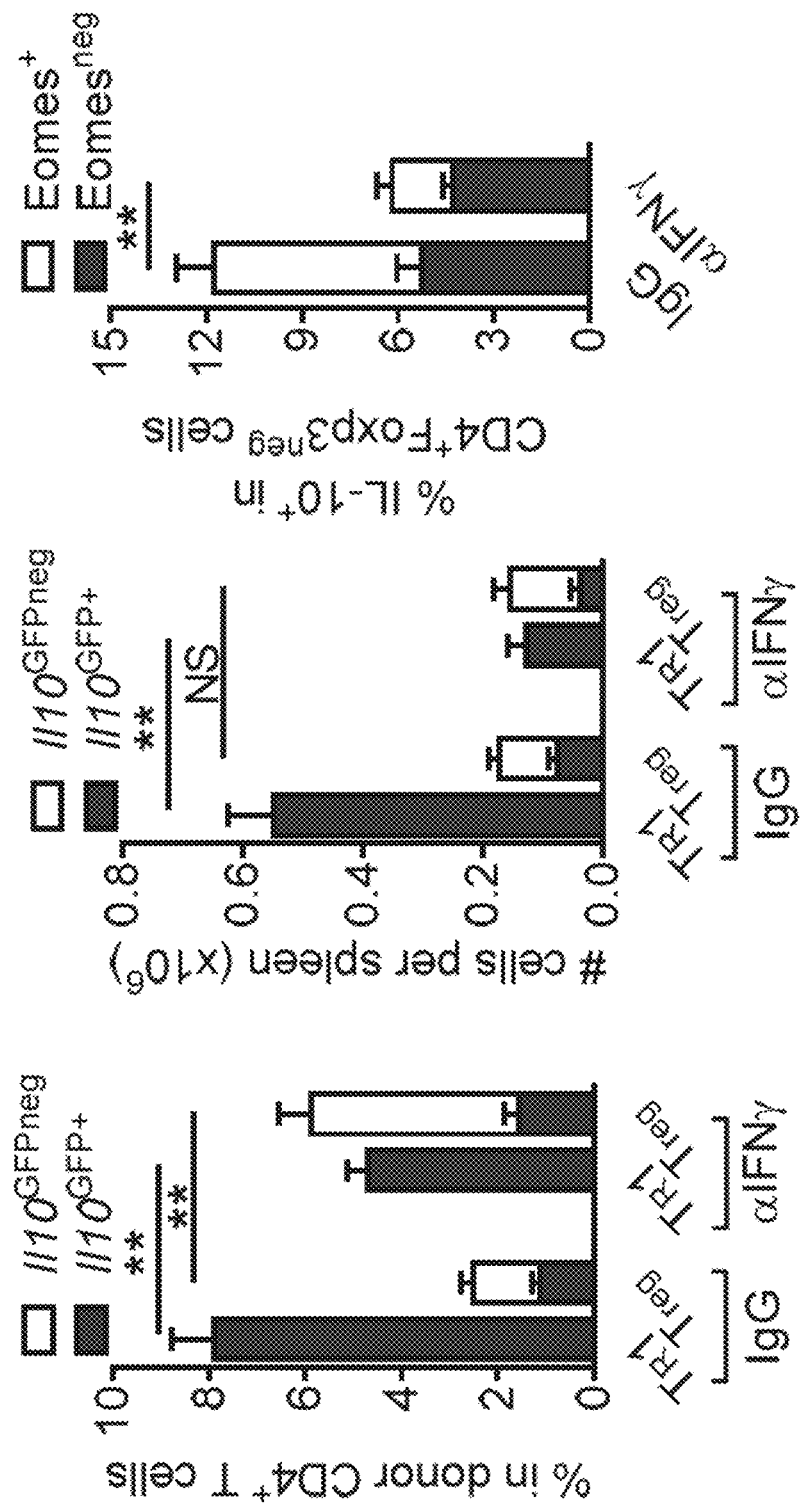
Figure 6D:
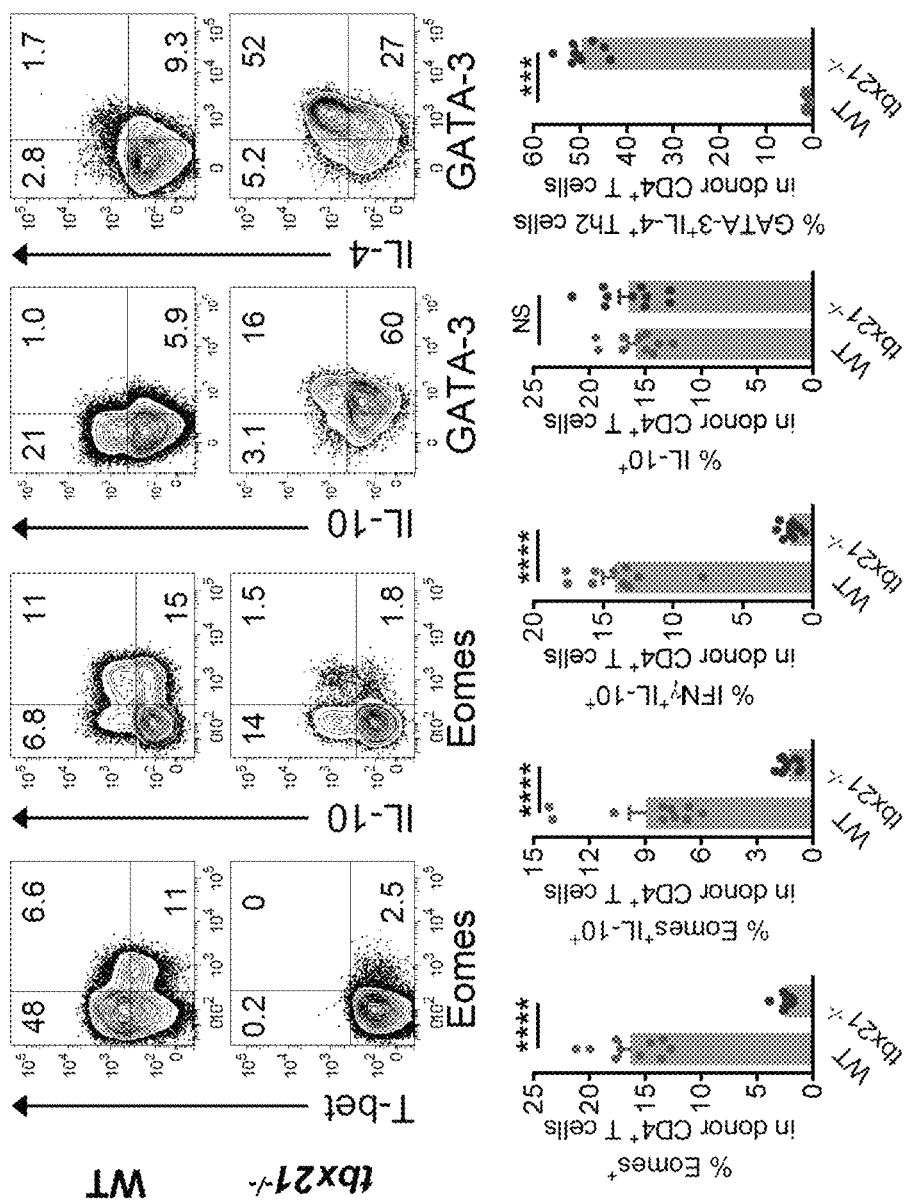
Figure 6E:
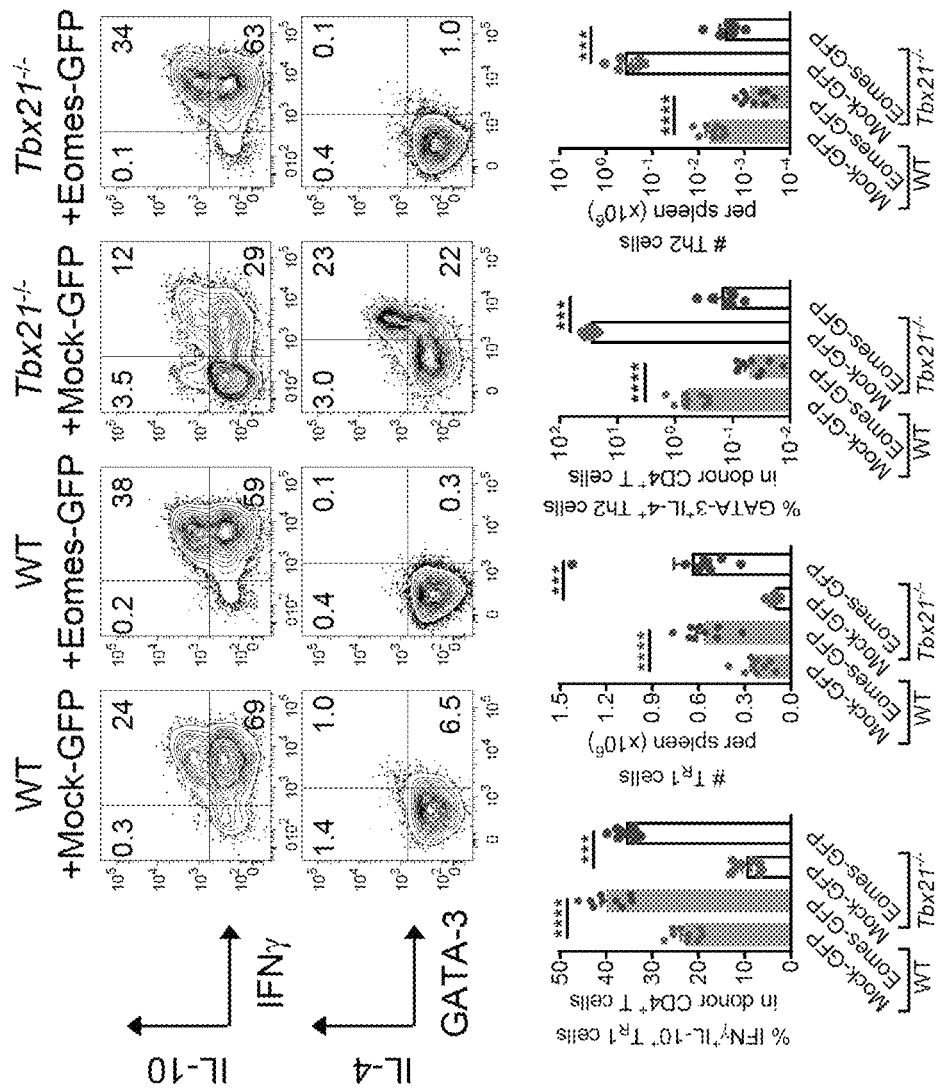
Figure 6F:
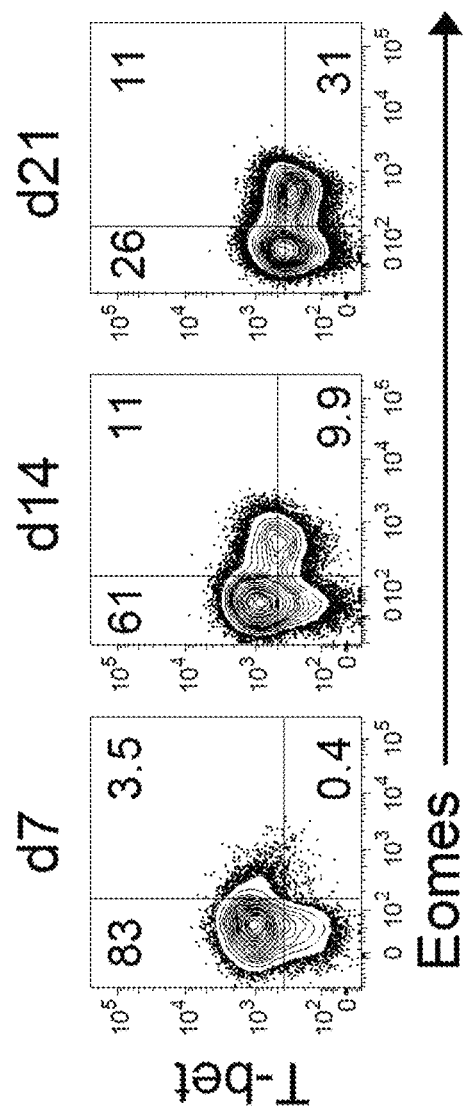
Figure 6G:
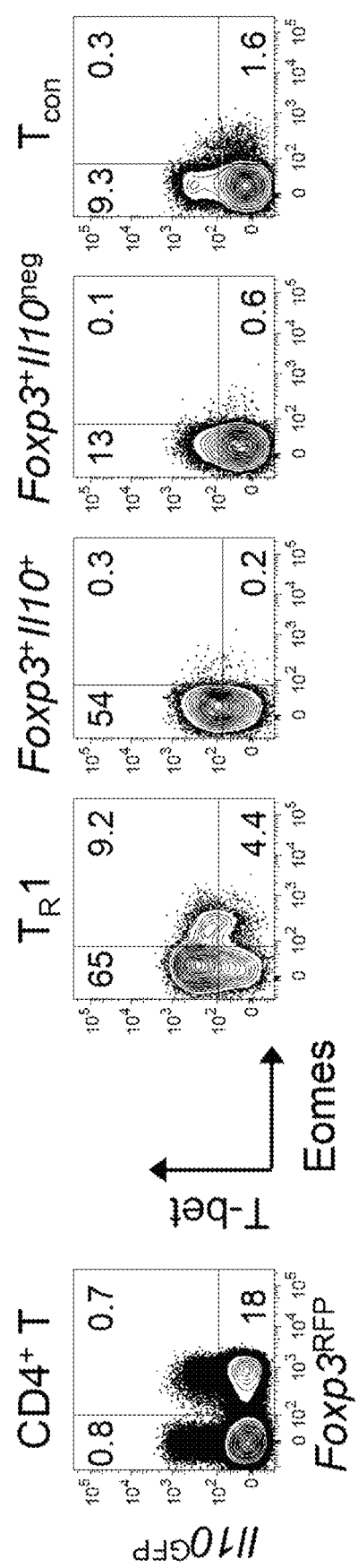
Figure 16A:
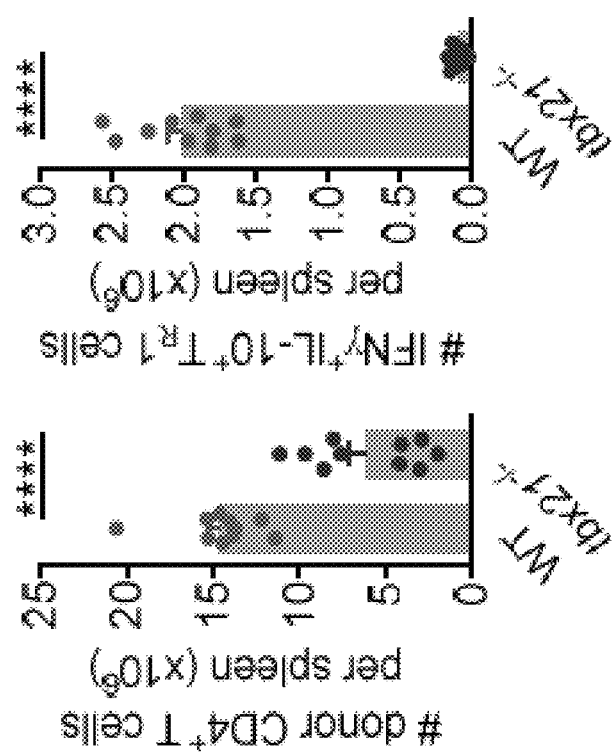
Figure 16B:
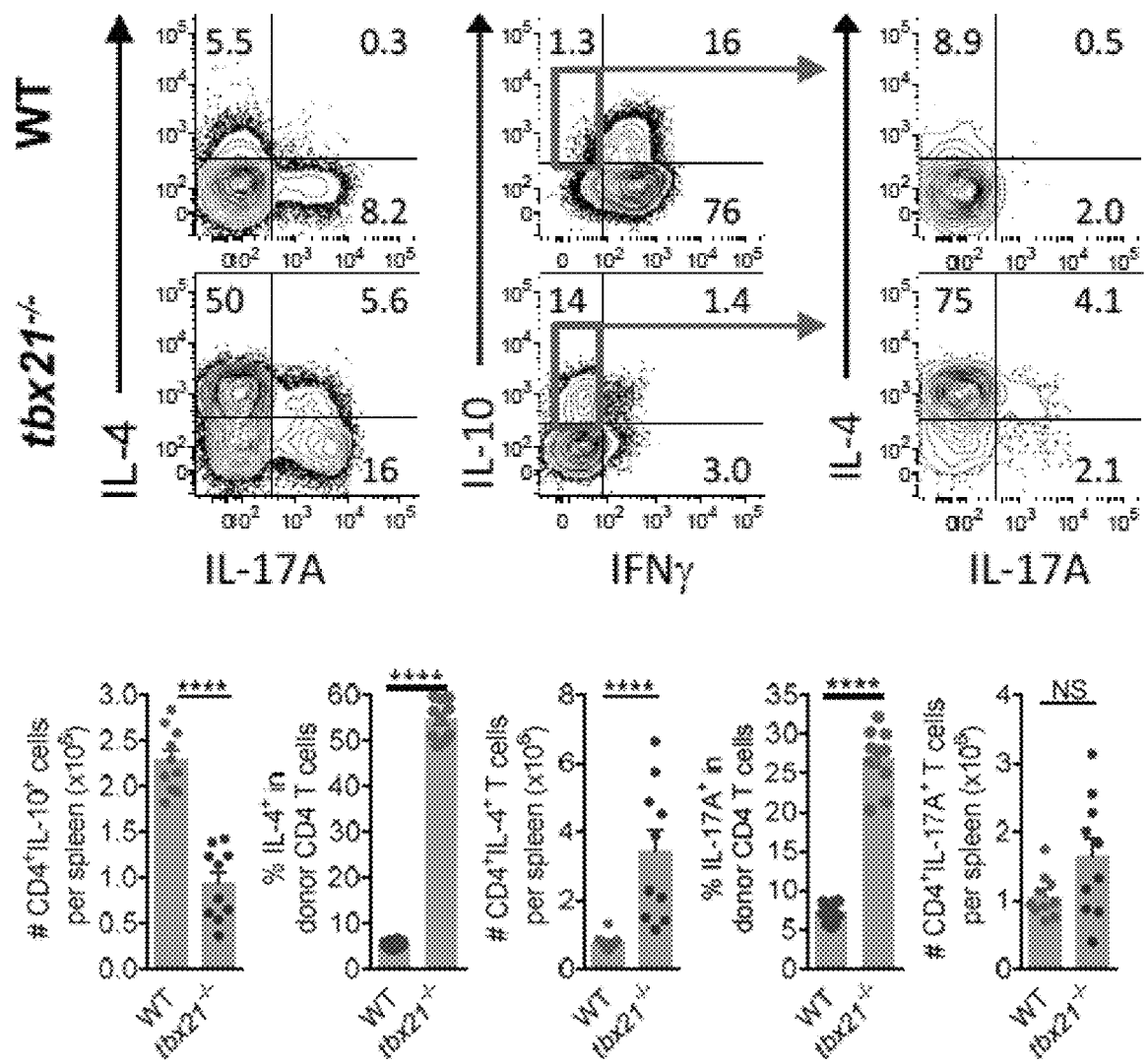
Figure 16C:
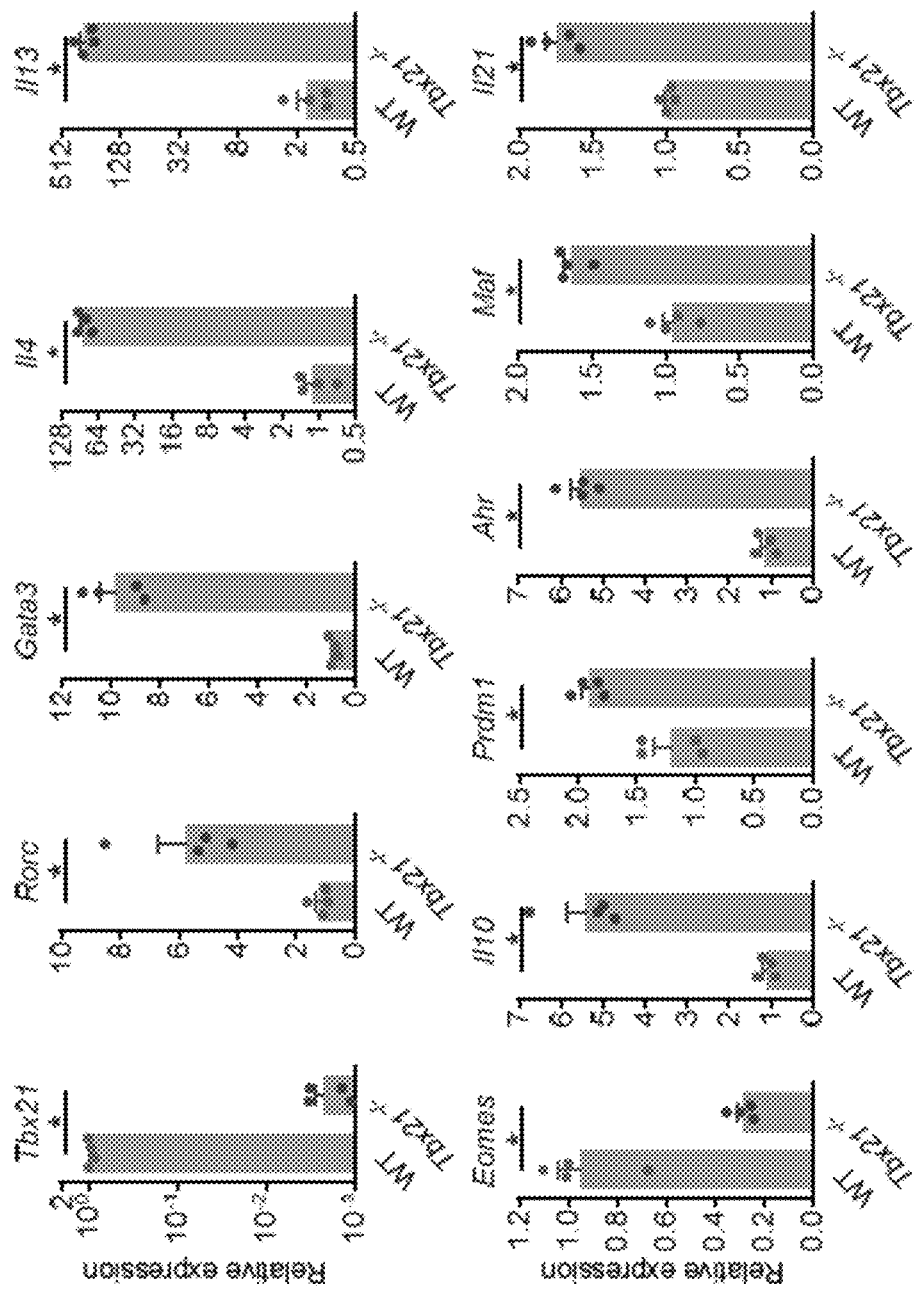
Figures 16D, 16E:
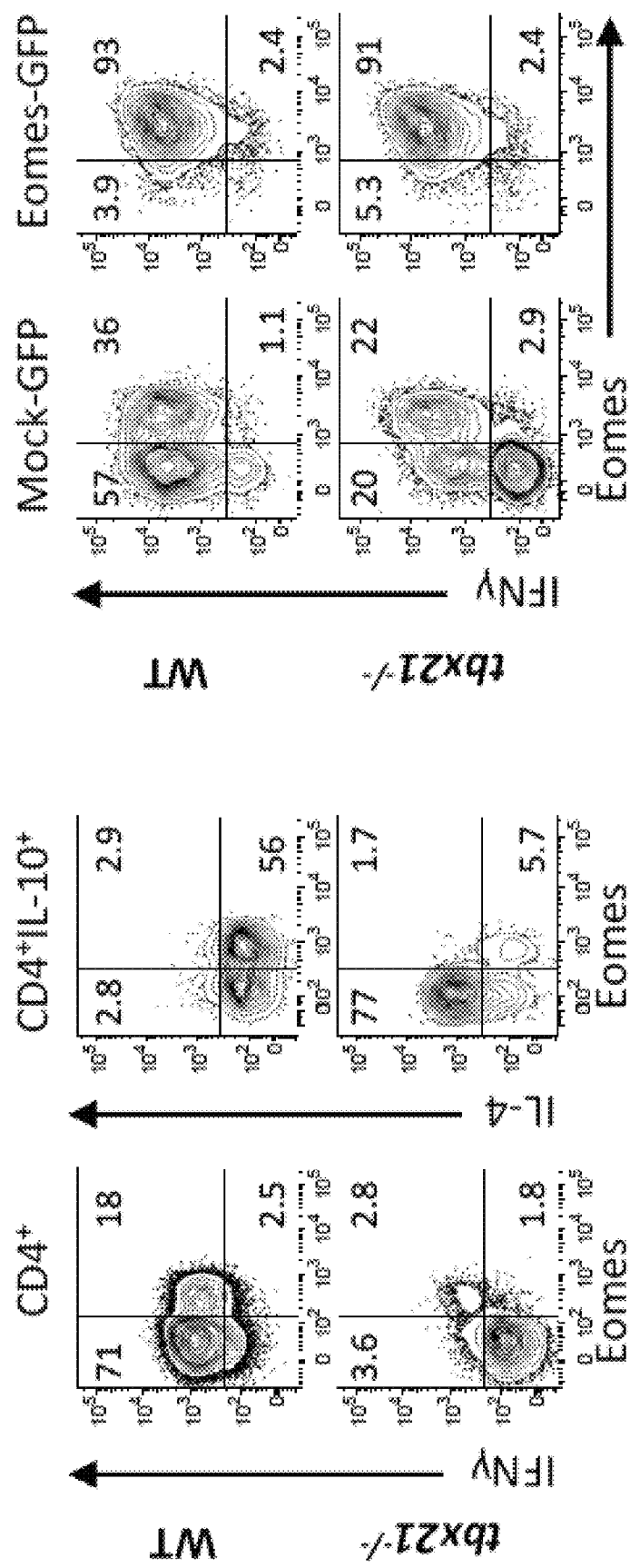
Figure 16G:
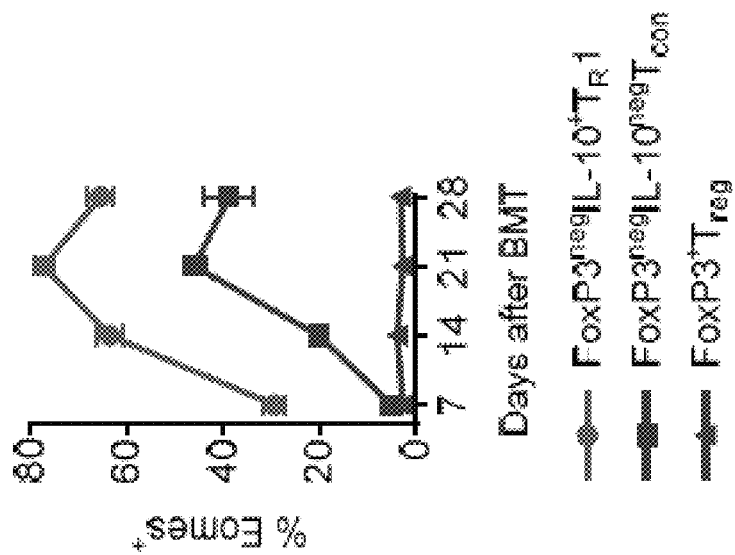
Figure 16F:
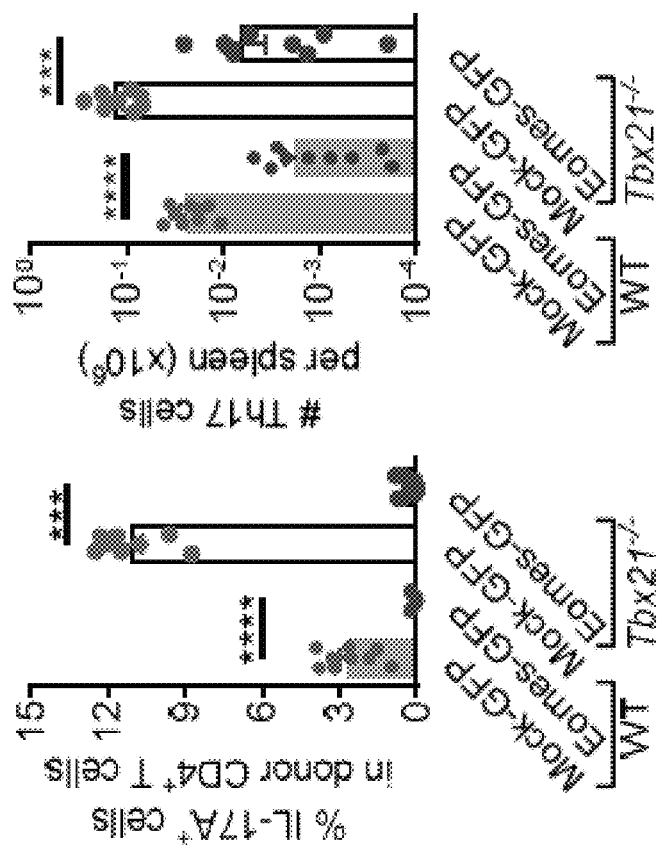

As co-expression of T-bet (encoded by Tbx21) and Eomes had been observed in $T_R1$ cells after BMT, the present inventors wished to test the role of IFNγ signalling and T-bet in $T_R1$ cell development. Transplanting Ifngr$^{-/-}$ donor T cells or neutralizing IFNγ resulted in reduced expression of T-bet and Eomes (FIG. 6A) with reduced expression of Eomes$^+$ $T_R1$ cells and expanded T$_{reg}$ cell populations (FIG. 6B, C). When Tbx21$^{-/-}$ CD4$^+$ T cells were transplanted during BMT, it was found that Eomes$^+$ $T_R1$ cells were dramatically reduced (FIGS. 6D, 16A). Although overall frequencies of IL-10$^+$CD4$^+$ T cells were unaffected, the absolute numbers were reduced (FIG. 6D). Importantly, however, the majority of the Tbx21$^{-/-}$ IL-10$^+$ CD4$^+$ T cells did not express IFNγ but rather IL-4 and GATA3 or IL-17A, indicating that these cells had been diverted to $T_H2$ or $T_H17$ cells, respectively (FIGS. 6D, 16B). Gene expression analysis confirmed polarization of donor CD4$^+$ T cells to $T_H2$ (Gata3, Il4, Il13) and $T_H17$ (Rorc, Ahr, Il21) lineages in the absence of T-bet. The transcription of Il10 (from Th2 cells)

was also increased (FIG. 16C). Notably, the residual Eomes$^+$ population in Tbx21$^{-/-}$ CD4$^+$IL-10$^+$ cells expressed IFNγ but did not express IL-4 (FIG. 16D). Thus, T-bet and IFNγ promote Eomes expression within the T$_R$1 lineage after BMT and, in concert with Eomes, repress alternate cell fates. To further understand the relative function of Eomes and T-bet in the differentiation of T$_R$1 cells, Tbx21$^{-/-}$CD4$^+$ T cells were retrovirally transduced with Eomes. Recombinant expression of Eomes fully rescued the expression of IL-10, IFNγ, and IL-10$^+$IFNγ$^+$ T$_R$1 cells and correspondingly suppressed the expression of GATA-3$^+$IL-4$^+$ T$_H$2 and IL-17A$^+$ T$_H$17 cells (FIGS. 6E, 16E,F).

Figures 16H, 16I:
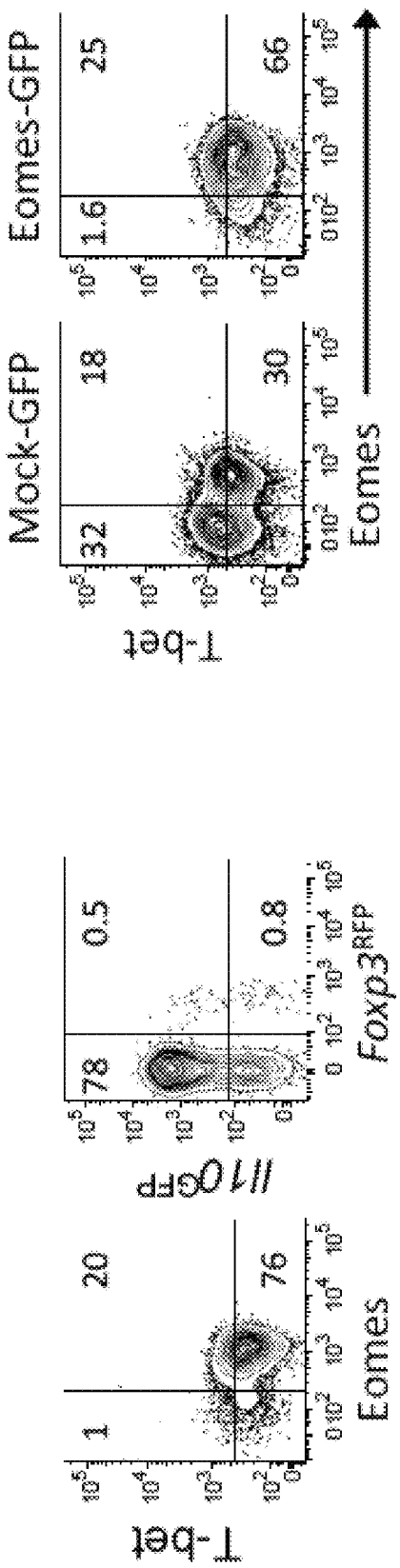

Next, the present inventors investigated whether there is a temporal and/or spatial collaboration between T-bet and Eomes during T$_R$1 cell development. First, Eomes expression in T$_R$1 cells was profoundly time-dependent after BMT (FIG. 16G), and CD4$^+$ T cells transited from a T-bet$^{hi}$Eomes$^{lo}$ to a T-bet$^{lo}$Eomes$^{hi}$ state over time (FIG. 6), correlating with the increasing frequency of T$_R$1 cells (FIG. 1). Furthermore, after repeated exposure to high levels of alloantigen in vivo, the majority of donor CD4$^+$ T cells had acquired Eomes (>95%) and converted to T$_R$1 cells (>70%) within four weeks of transfer into secondary BMT recipients (FIG. 16H). Consistently, recombinant expression of Eomes suppressed the expression of T-bet while promoting T$_R$1 cell differentiation (FIGS. 3B, 16I). T$_R$1 cells (Foxp3$^{RFRneg}$Il10$^{GFP+}$), found in low frequencies in naïve mice, also exhibited higher Eomes expression. This was specific to T$_R$1 cells as IL-10 producing T$_{reg}$ cells (Foxp3$^{RFRneg+}$ Il10$^{GFP+}$) expressed some T-bet but not Eomes (FIG. 6). Collectively, these data show that both T-bet and Eomes are required for T$_R$1 cell differentiation, which is characterized by the initial up-regulation of T-bet, the acquisition of Eomes expression and the subsequent down-regulation of T-bet, resulting in a T-bet$^{lo}$Eomes$^{hi}$ phenotype.

Recipient DC and Donor-Derived IL-27 Promote T$_R$1 Development

Figures 7A, 7B:
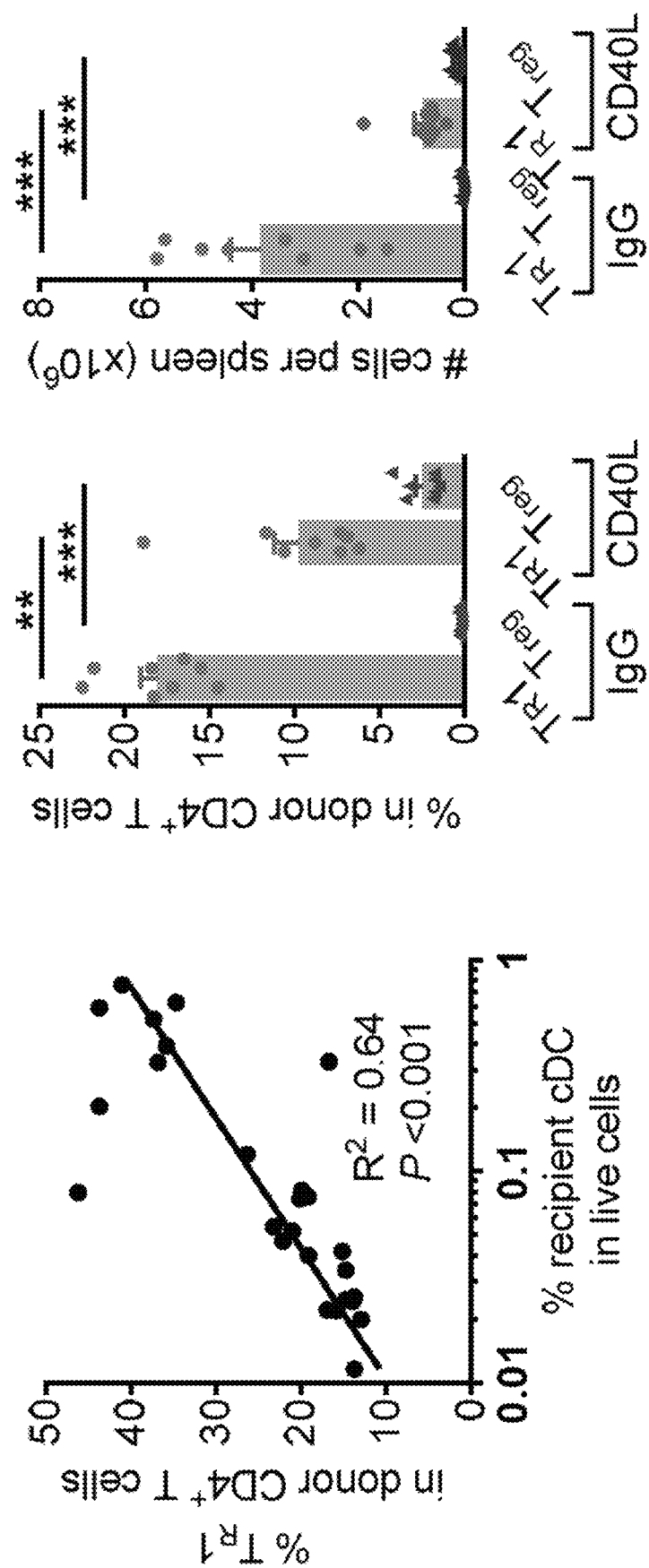
FIG. 7 is a graphical representation showing that Recipient DC and macrophage-derived IL-27 promote the development of $T_R1$ cells. (A-K) B6D2F1 mice were transplanted with TCD BM and CD4$^+$ T cells and spleen examined. (A) Correlation of $T_R1$ cells (Il10$^{GFP+}$Foxp3$^{RFPneg}$) with proportions of recipient DC at d14 (n=26). (8) Frequencies of $T_{reg}$ (Foxp3$^{GFP+}$) and $T_R1$ (IFNγ$^+$IL-10$^+$) cells at d14 in the presence or absence of CD40L inhibition (n=8 per group, grafts were CD4$^+$ Foxp3$^{GFPneg}$). (C) WT.B6D2F1 or CD11c-DOG×DBA/2 F1 recipients were treated with DT to deplete recipient cDC and received B6.WT or MHC-II$^{-/-}$ BM respectively. Expression of $T_R1$, $T_{reg}$ cells, Eomes and IL-10 at d14 are shown (n=10 and 7 respectively). (D) Recipients of WT or CD11c-DOG BM were treated with DT to deplete donor cDC with expression of $T_R1$ and $T_{reg}$ cells at 10 shown (n=10 per group). (E) Data from (A) and (8) demonstrate correlation between numbers of $T_R1$ cells and IL-27$^+$ cells per spleen at d014 (n=20). (8) Recipients were treated with IL-6R and spleens analyzed at d5. Phosphorylation of STAT1 and STAT3 in response to IL-6 or IL-27 (n=10 per group). (G and H) Recipients were treated with IL-6R and spleens analyzed at 10. (G) Expression of Foxp3$^{RFPneg}$ Il10$^{GFP+}$ $T_R1$, Foxp3$^{RFP+}$ $T_{reg}$, Eomes and IL-10 in donor CD4$^+$ T cells and (H) numbers of IL-27$^+$ cells with intensity (MFI) of IL-27 (n=9-10 per group). (I and J) Phenotypes of CD3$^{neg}$ IL-27 secreting cells at d014 are shown. (K) Expression of IL-27 from recipient DC at d+1 after BMT. (L and M) B6.WT or B6.Foxp3$^{GFP-DTR}$ mice were treated with DT for up to 2 weeks and spleens analyzed. (L) Phenotype of IL-27 secreting macrophage in CD3$^{neg}$ splenocytes and (M) expression of Eomes$^+$IL-10$^+$ cells over time with representative plots at 14. Data represents mean±SEM.
Figures 7C, 7D:
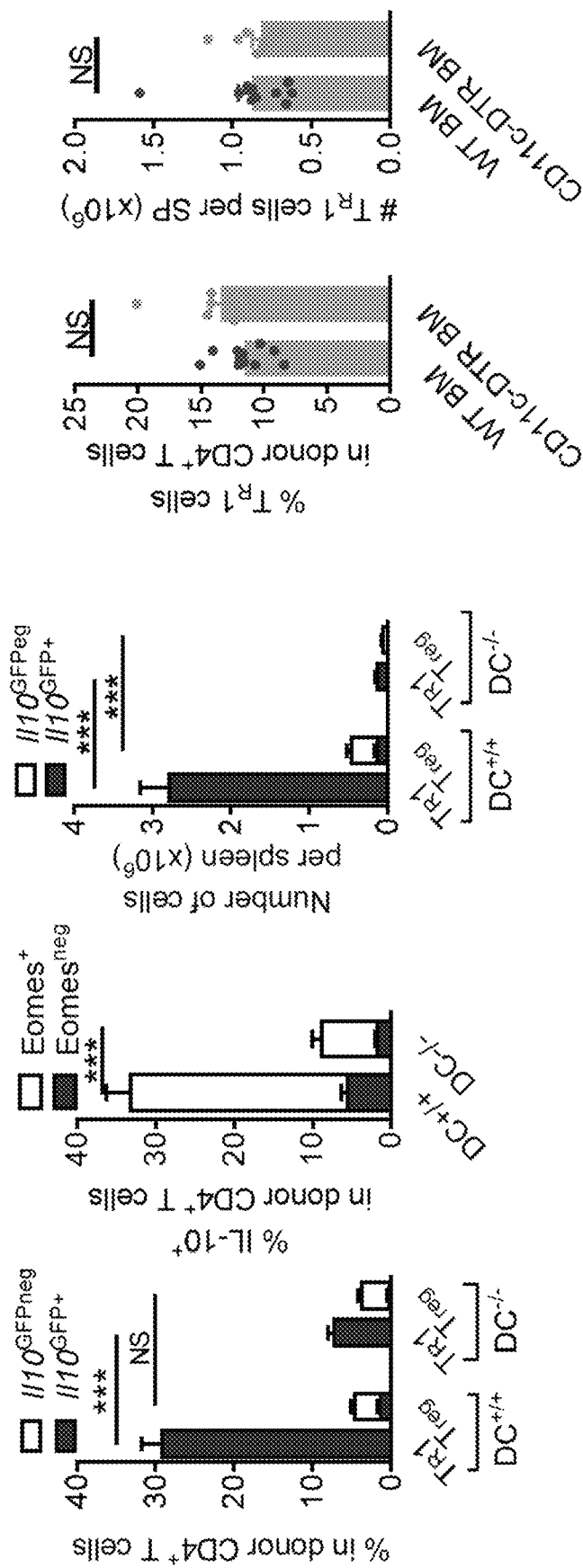
Figure 7F:
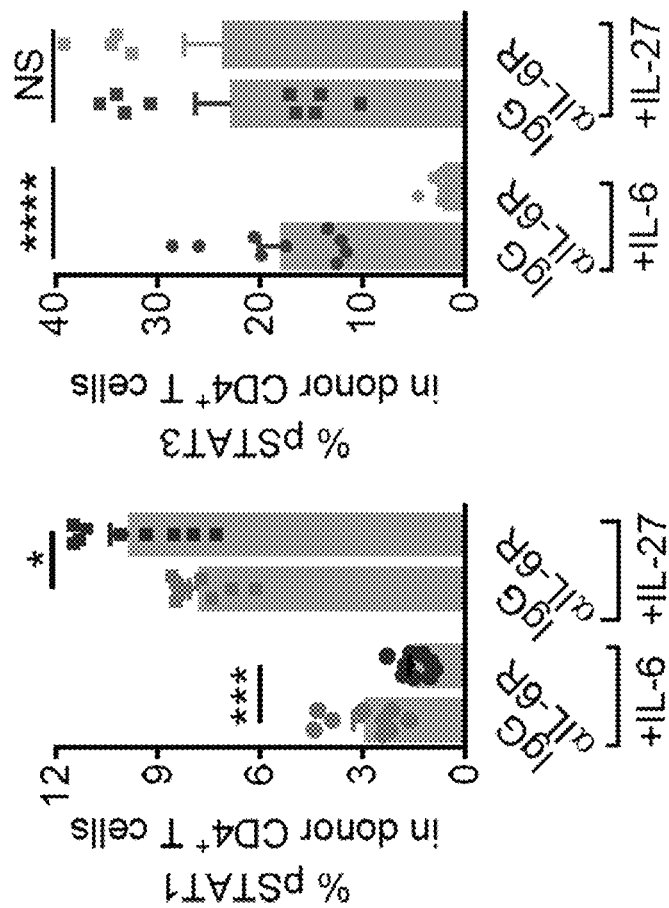

GVHD is initiated by recipient antigen presenting cells (APC) and is influenced by the intensity of conditioning, i.e. total body radiation (TBI) and chemotherapy dose-intensity, in part through inflammatory cytokine dysregulation (26, 27). The present inventors thus hypothesized that T$_R$1 cells may also be generated in an APC and conditioning-dependent fashion. The frequency of T$_R$1 cells in donor CD4$^+$ T cells indeed correlated with the frequency of residual recipient conventional dendritic cells (DC) (FIG. 7A) and reduced intensity of TBI that favour the persistence of recipient DC (FIG. 17A). Blocking DC function by CD40L inhibition reduced T$_R$1 cells whilst favouring T$_{reg}$ cell development (FIG. 7B). In line with this observation, depletion of both donor and recipient DC dramatically reduced the development of T$_R$1 cells early after BMT (FIG. 7C). While the proportions of T$_{reg}$ cells were unaffected, absolute numbers were reduced, albeit much less dramatically than T$_R$1 cells (FIG. 7C). In contrast, the depletion of donor DC or inactivation of donor APC function in isolation did not impair T$_R$1 cell development (FIGS. 7D, 17B,C), indicating that recipient DC are required for the development of T$_R$1 cells early after BMT.

Figure 7E:
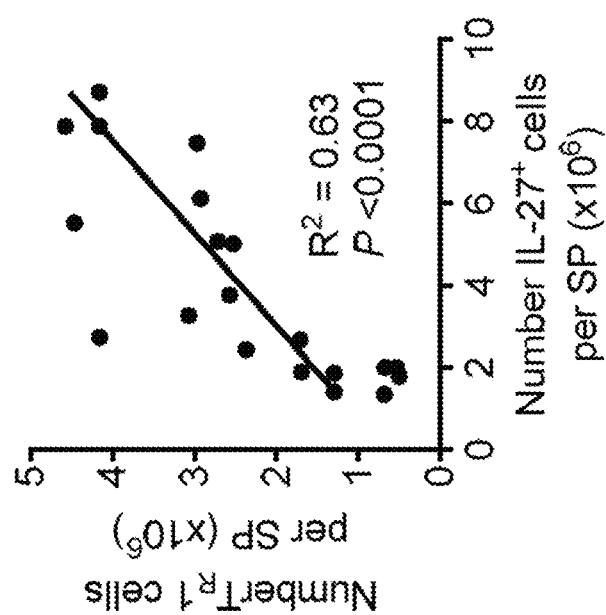
Figure 7I:
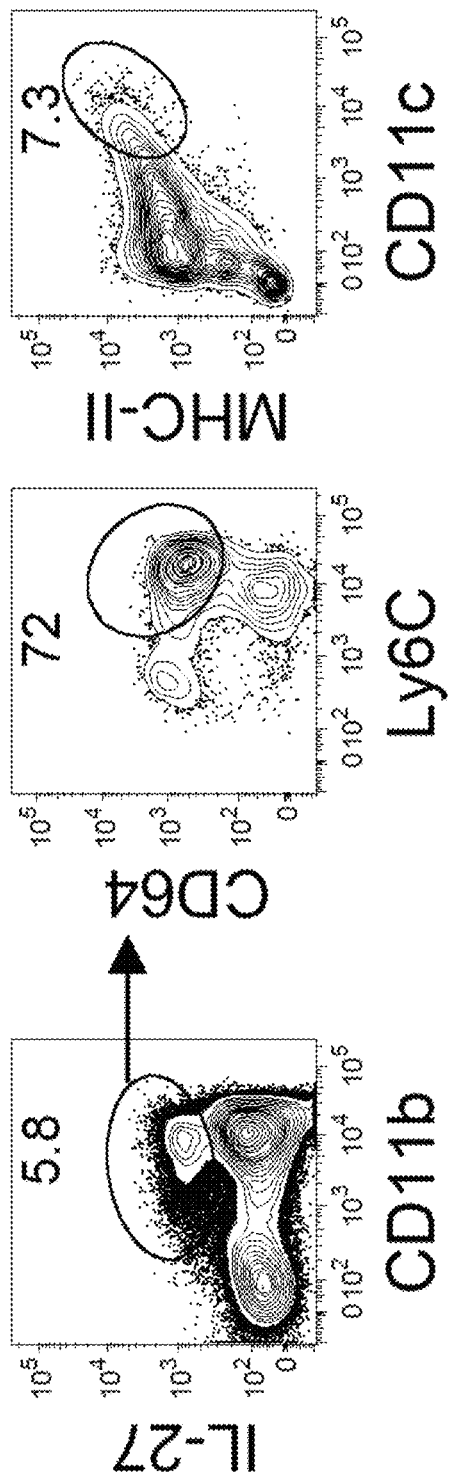
Figure 7J:
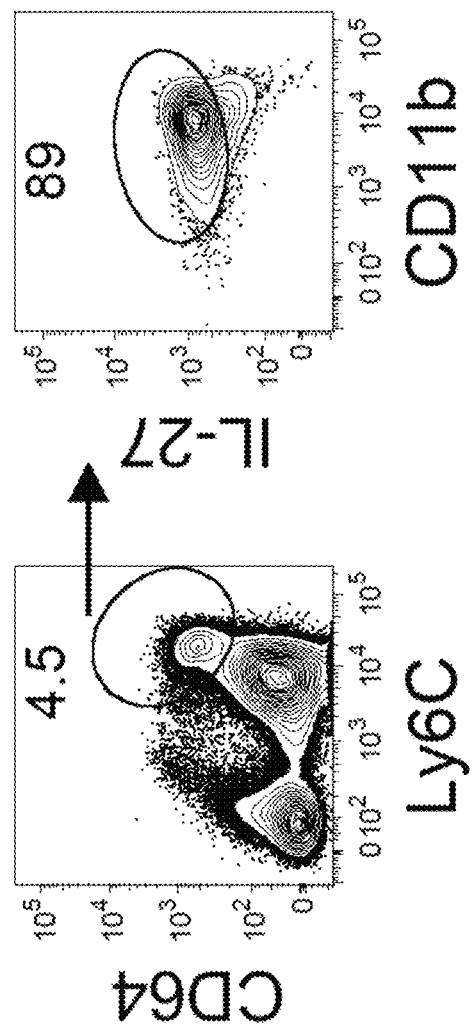
Figure 7K:
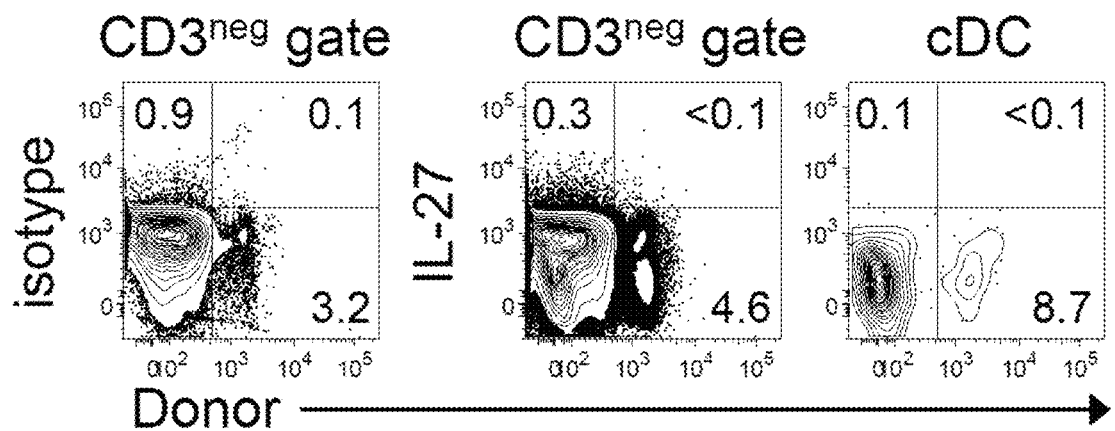

Consistent with the notion that Eomes$^+$ T$_R$1 cells are dependent on IL-27 signalling and further confirming critical role of IL-27 in promoting T$_R$1 cell development, the present inventors found that the number of T$_R$1 cells significantly correlated with the number of IL-27$^+$ cells in the spleen (FIG. 7E). As IL-27R and IL-6R share and compete for the same signalling component, gp130 (28), it was hypothesized that blocking IL-6R may favour IL-27R function. As expected IL-6R inhibition blocked STAT3 phosphorylation in response to IL-6 but not IL-27 (FIG. 7B). In contrast, IL-6R inhibition enhanced STAT1 phosphorylation in response to IL-27 early after BMT (FIG. 7B) and resulted in increased expression of T$_R$1 cells and a small increase in the frequencies of T$_{reg}$ cells (FIGS. 7G, 17D). The enhanced STAT1 phosphorylation in response to IL-27 following IL-6R inhibition was not a result of an increase in the number of cells producing IL-27 itself or IL-27 production on a per cell basis (FIG. 7H). The present inventors next sought to identify the cellular sources of IL-27 after BMT. The majority of IL-27 (70-80%) was produced by Ly6C$^{hi}$ donor macrophages (CD11b$^+$, MHC II$^+$, Ly6C$^{hi}$, F4/80, CD64$^+$ and CCR2$^+$) with a more limited contribution from donor DC (CD11c$^+$, MCH-II$^+$) (FIG. 7I). More than 80% of all Ly6C$^{hi}$ donor macrophages were secreting IL-27 after BMT (FIG. 7J). Depletion of donor DC did not impair the overall frequencies or numbers of IL-27$^+$ cells (FIG. 17B), consistent with the lack of contribution by donor DC to T$_R$1 cell development. Lastly the present inventors demonstrated that recipient DC did not produce IL-27 early after BMT (FIG. 7K), suggesting that the requirement of recipient DC to T$_R$1 cell development relates to their capacity for alloantigen presentation and not IL-27 production. Thus donor macrophages appear the main producers of IL-27 and, in concert with the initial stimulation by recipient DC, drive Eomes-dependent T$_R$1 development after BMT.

Figure 7L:
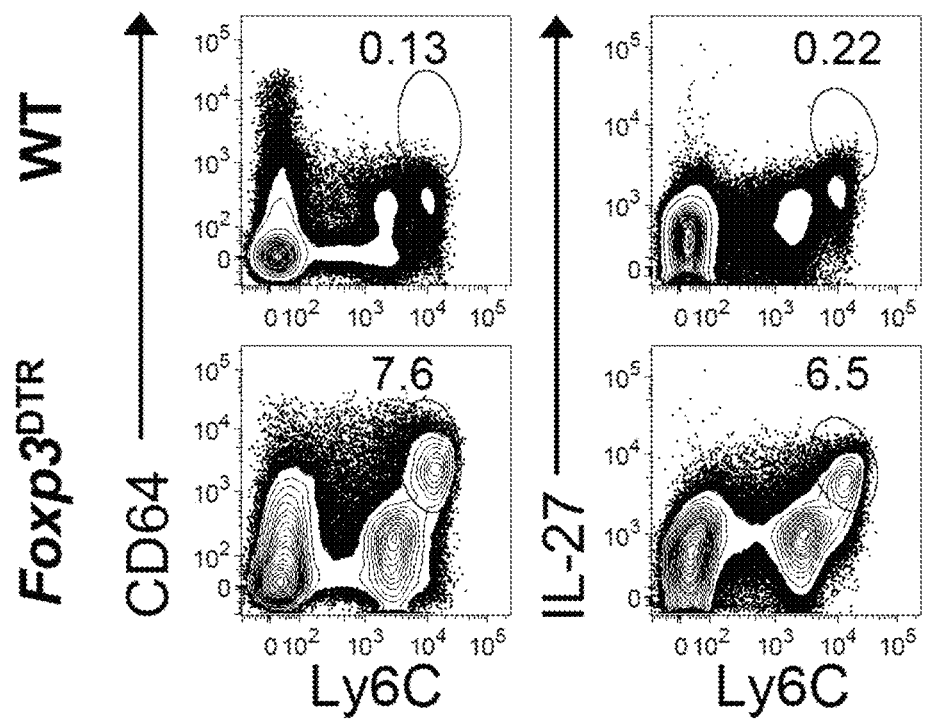
Figure 7M:
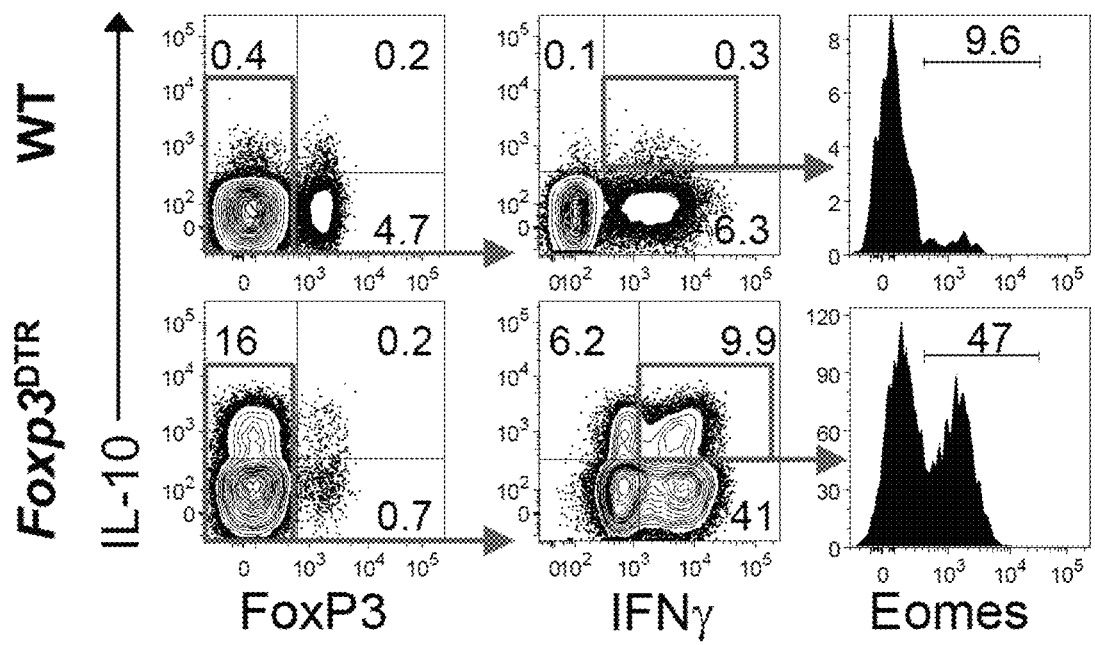
Figure 7M:
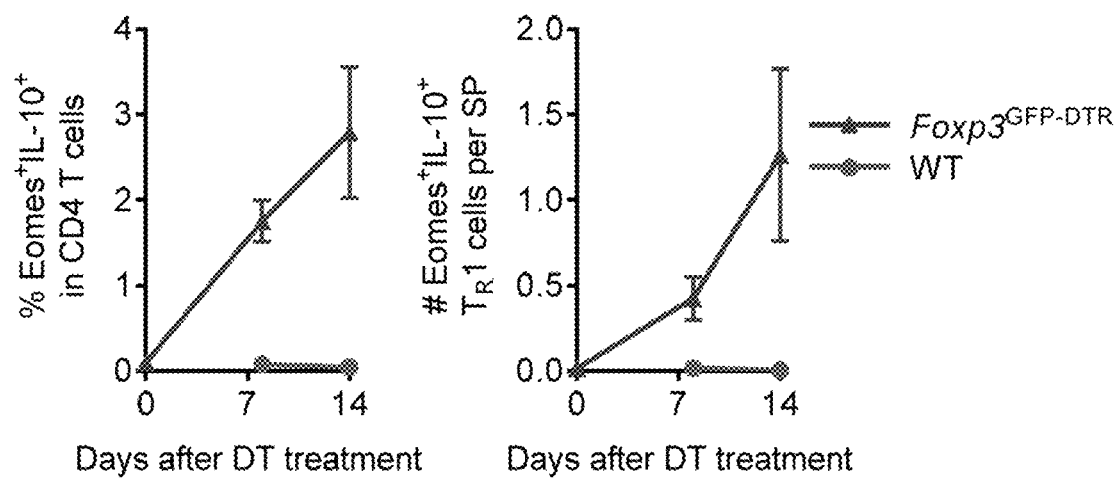

To further understand the requirement of Eomes in T$_R$1 cell development, the expression of Eomes$^+$ T$_R$1 cells was investigated in other models of immune pathology. To this end Foxp3$^{GFP-DTR}$ mice were used to temporarily deplete T$_{reg}$ cells, thereby causing autoimmunity (29-31). Indeed, depletion of T$_{reg}$ cells from adult mice resulted in a dramatic increase in IL-27 producing Ly6C$^{hi}$ macrophages (FIG. 7L) and critically, induced large numbers of Eomes$^+$ T$_R$1 cells (FIG. 7B). Thus, the data presented herein demonstrate that different inflammatory conditions result in the development of Eomes$^+$ T$_R$1 cells. Furthermore, the results presented herein demonstrate that defects in T$_{reg}$ cells are associated with compensatory increases in Eomes$^+$ T$_R$1 cells.

Identification of T$_R$1 Cells in Humans

Figure 8A:
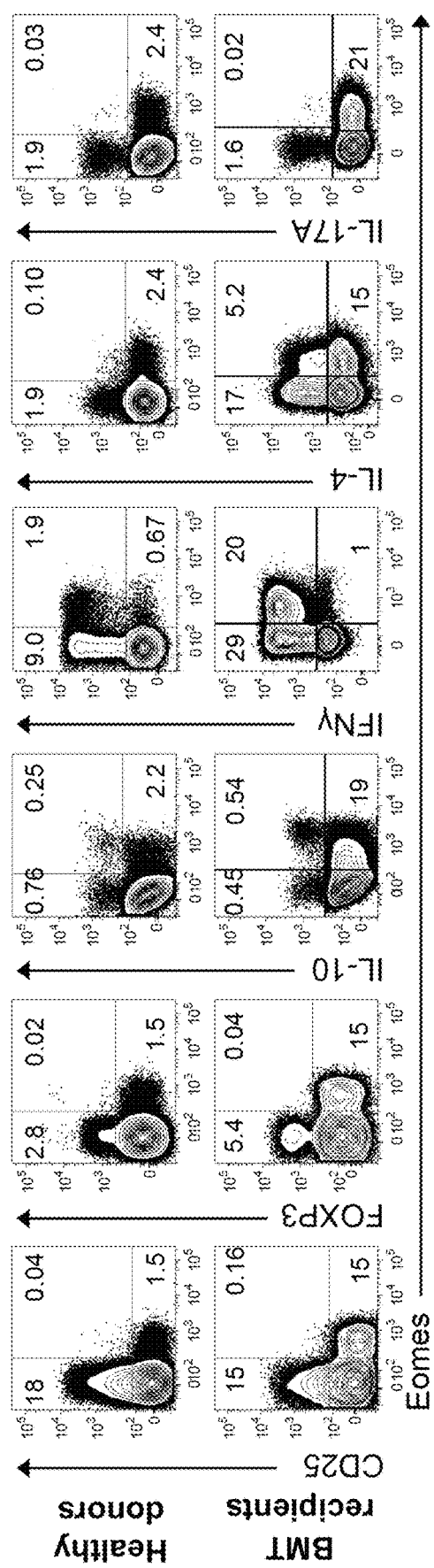
FIG. 8 is a graphical representation showing that co-expression of T-bet and Eomes identifies a $T_R1$ cells enriched population in human CD4$^+$ T cells. (A) Representative plots show the correlation of Eomes to CD25$^{neg}$, FOXP3 and cytokines in CD4$^+$ T cells in healthy individuals and at 060 after clinical allo-BMT. (B) Frequencies of $T_R1$ cells defined as IFNγ$^+$IL-10$^+$ or Eomes$^+$IL-10$^+$ in CD4$^+$ T cells in healthy donors (n=27) or 060 after clinical allo-BMT (n=43). (C-E) Expression of cytokines in the T-bet$^{lo}$Eomes$^{hi}$ population relative to total CD4$^+$ T cells or subpopulations defined with differential expression of Eomes and T-bet in healthy individuals (HD, n=27) and at d60 after allo-BMT (BMT, n=43). Data represents median±interquartile range.
Figure 8B:
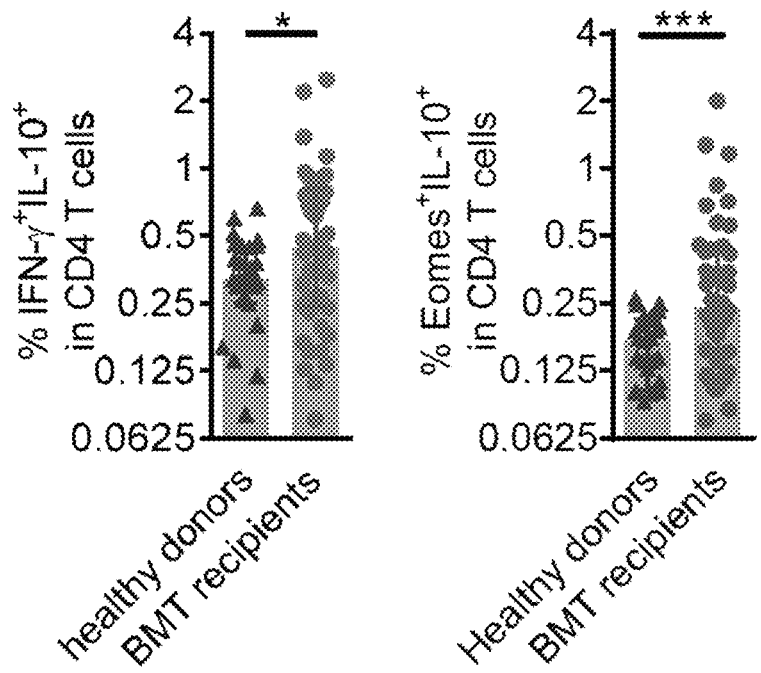
Figure 8C:
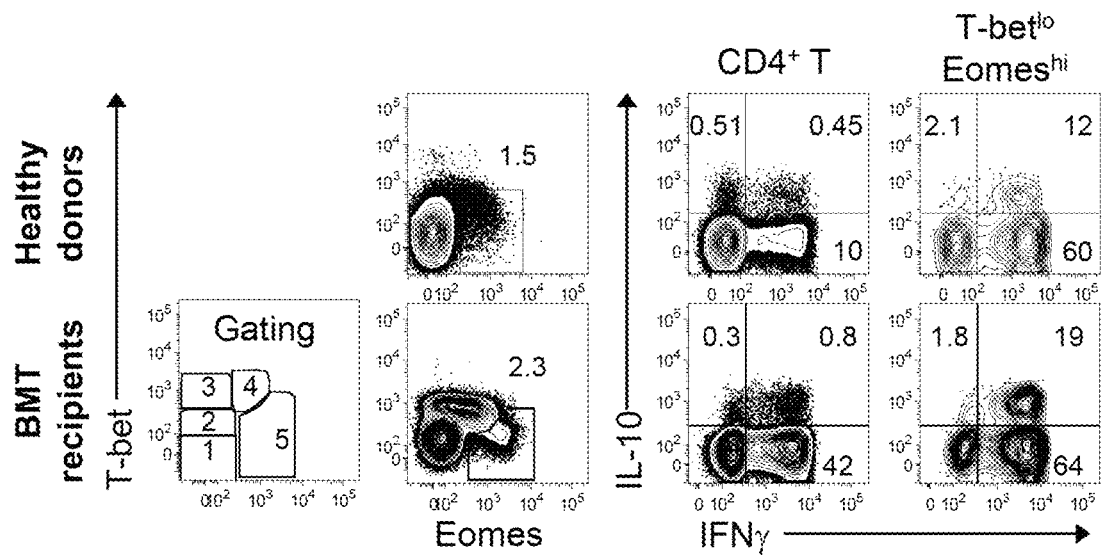
Figure 8D:
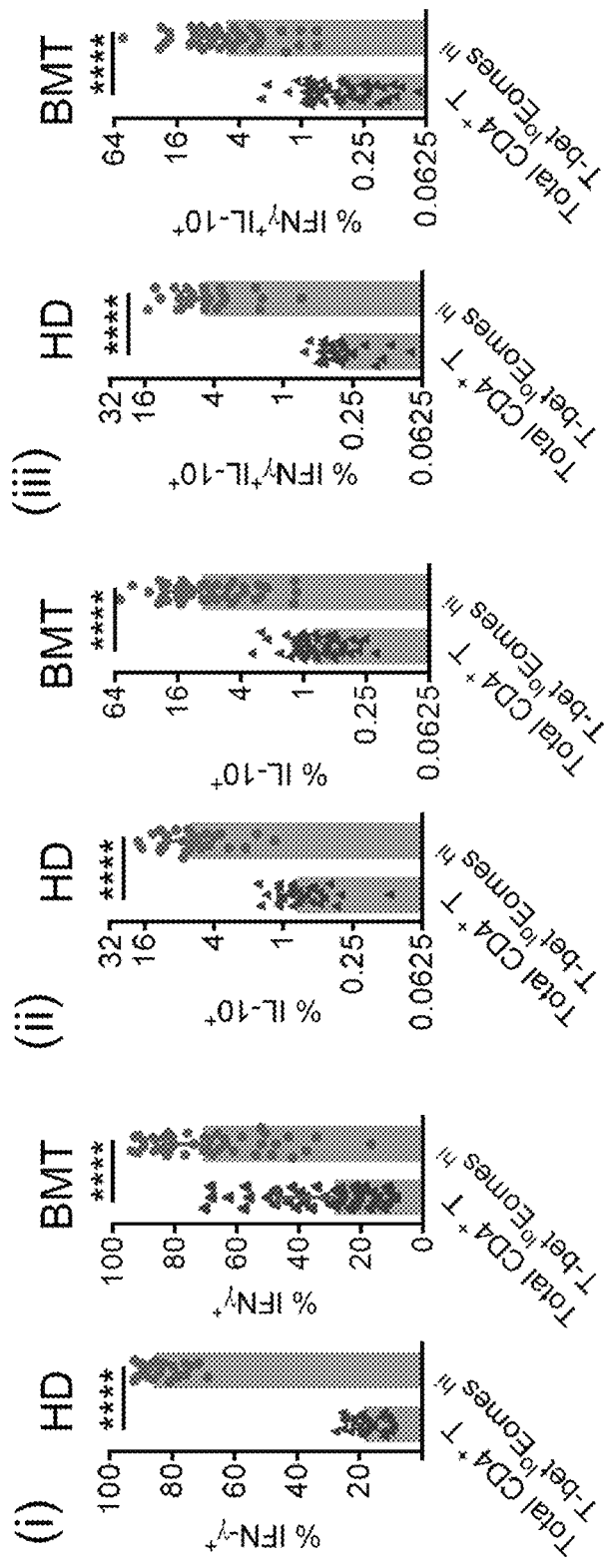
Figure 8E:
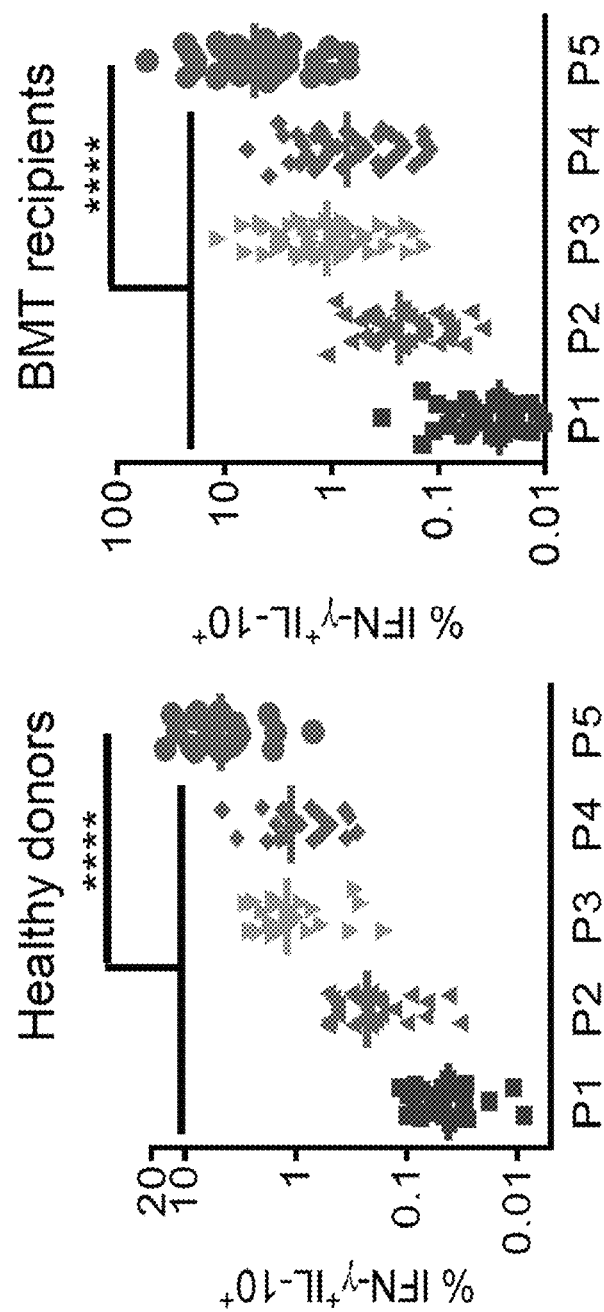

To validate whether the present findings from experimental BMT can be translated into humans, the expression of Eomes, IL-10 and other markers was analyzed in CD4$^+$ T lymphocytes collected from healthy donors and BMT recipients. Eomes$^+$CD4$^+$ cells from healthy individuals as well as BMT recipients were CD25lo, FOXP3neg, IFNγ$^{hi}$, IL-4$^{lo}$ and IL-17A$^{neg}$ and a proportion secreted IL-10 (FIG. 8A). Thus, human Eomes$^+$IL-10$^+$ cells show the characteristics of T$_R$1 cells. Of note, compared to currently utilized IL-10$^+$ IFNγ$^+$ staining methods, the use of Eomes in defining IL-10 positive T$_R$1 cells (Eomes$^+$IL-10$^+$) provides better discrimination of T$_R$1 cells between healthy donors and BMT recipients (FIG. 8B). Furthermore, the use of T-bet and Eomes expression defines populations with increasing proportions of IL-10$^+$IFNγ$^+$ T$_R$1 cells (FIG. 8C-E), consistent with the requirement for these transcription factors at different stages of differentiation both in steady state and after clinical BMT. IL-10$^+$IFNγ$^+$ T$_R$1 cells were enriched (>10 fold) in the T-bet$^{lo}$Eomes$^{hi}$ population, which exhibited an effector memory (CD45RA$^{neg}$CCR7$^{neg}$) phenotype (FIGS. 8C-E, 18). Thus, consistent with the findings in the mouse model, after clinical BMT high Eomes and low T-bet expression in CD4+ T cells can be used to identify a population that is enriched for $T_R1$ cells.

SUMMARY

The present inventors demonstrate that Eomes acts together with Blimp-1 and specifically drives the development of $T_R1$ cells. Based on the data presented herein, a model for the differentiation of $T_R1$ cells after BMT is proposed as illustrated in FIG. 19. In this model, antigen presentation by recipient DC and macrophages-derived IL-27 provide the cellular and molecular cues for the development of $T_R1$ cells, inducing Blimp-1 expression, which initiates the transcription of Il10. Blimp-1 is also required for Eomes expression, and both factors act in concert, enabling stable IL-10 production and $T_R1$ cell differentiation. Concurrently, T-bet is required to suppress GATA3 and RORγt whilst driving IFNγ and Eomes expression ultimately leading to a T-bet$^{lo}$Eomes$^{hi}$ phenotype, which can reliably identify $T_R1$ cells after BMT as well as in steady state in mouse and man.

There is still debate whether $T_R1$ cells constitute an independent lineage or simply represent IL-10 producing $T_H1$ cells. In particular, the lack of a master transcriptional factor for $T_R1$ cells has made progression of the field difficult (5, 13, 33). Multiple transcription factors, including Blimp-1, AhR and c-Maf are induced by IL-27 and have been shown to be critical for $T_R1$ cell differentiation (5-8, 10); however, none of them appear to be specific to the $T_R1$ lineage. Eomes is a T-box transcription factor which is more often than not coupled with T-bet in the biology of CD8+ T cells and NK cells (34, 35). Its roles in regulating functions of CD4+ T cells (36, 37) and suppressing $T_{reg}$ and $T_H17$ cells differentiation have been described recently (38, 39). Here the present inventors demonstrate that IL-10IFNγ+ $T_R1$ cells are uniquely dependent on Eomes. They found that Eomes bound to the Il10 and Ifnγ promoters. Similarly, it has been shown that Eomes also binds to the promoter of Gzmb (35), expression of which is another feature of $T_R1$ cells. Recombinant expression of Eomes was sufficient to promote IL-10 and GzmB and suppress other lineage-characteristic transcription factors (e.g. FoxP3, GATA-3, RORγt and BCL-6) and cytokines (e.g. IL-2, IL-4, IL-13, GM-CSF and IL-17A). Therefore, expression of Eomes and IL-10 within CD4+ T cells is considered by the present inventors to define the $T_R1$ cell lineage.

Increasing data has suggested a dose relationship between $T_R1$ and $T_H17$ cells linked via AhR, c-Maf and IL-21 (10, 23, 24, 40). However, $T_R1$ and $T_H17$ cells require different cytokines for their respective differentiation, IL-27/IL-10 for the former and IL-6/TGF-β/IL-23 for the later (12, 41-43). Multiple groups have independently shown IL-27 opposes the functions of IL-6/IL-23 in $T_H17$ differentiation (8, 28, 44). The data presented herein demonstrate that inhibition of IL-6R signaling favors IL-27 function and subsequent development of Eomes+ $T_R1$ cells. It is further shown that Eomes distinguishes $T_R1$ cells from other $T_H$ lineages including $T_H17$ cells and its over-expression represses polarization to $T_H17$ cells. This is in line with the notion that Eomes suppresses $T_H17$ cell differentiation by directly inactivating Rorc and Il17a promoters (39). A role for IL-27 in inhibiting $T_{reg}$ reconstitution after BMT has also recently been reported (45), consistent with the counter-balanced $T_R1$ expansion seen here. There appears to be significant interplay between IL-6 and IL-27 (28), an effect also seen during GVHD. IL-6 inhibition has an intriguing capacity to enhance IL-27 responses and thereby to promote $T_R1$ cell differentiation, an effect likely contributing to clinical efficacy (46).

Eomes can be regulated by T-bet in a Runx-3 dependent manner and the differential expression of these two T-box transcription factors is critical for the differentiation of CD8+ T cells (47, 48). In line with this notion, the present inventors show that IFNγ signalling and T-bet expression were required for Eomes expression, demonstrating an important role of T-bet in the early phase of $T_R1$ cell development. Downstream of IL-27, Blimp-1 is critical for the expression of IL-10 in CD4+ T cells in various models (6-8, 21, 49). Here it is shown that Eomes+ $T_R1$ cells are regulated by both Blimp-1 and T-bet, consistent with a recent report that demonstrated dose collaboration between Blimp-1 and T-bet in CTL generation (50). In addition, binding of Blimp-1 to the Eomes promoter in CD8+ T cells during viral infection has been described (32), suggesting that Blimp-1 not only regulates IL-10 expression directly but also contributes to the induction or maintenance of Eomes expression in $T_R1$ cells. Notably, both Blimp-1 (6) and Eomes bind to the Il10 locus, and the activity of both is required to promote efficient $T_R1$ differentiation and Il10 expression. Interestingly, similar to Eomes, Blimp-1 is not only required for IL-10 expression but also for granzyme B (51). The present inventors also confirmed that IL-10 itself contributes to $T_R1$ cell differentiation, a T cell extrinsic effect likely via myeloid cells (22, 25). Overall these data suggest that the functional interactions between Blimp-1, T-bet and Eomes are important for the differentiation of CD4+ T cells and $T_R1$ lineage in particular.

The present inventors consider that the identification of the bona fide transcriptional and cellular control of $T_R1$ cell development will permit therapeutic utilization of $T_R1$ cells in transplantation and other diseases where excessive and aberrant immunity results in immune pathology.

Materials and Methods

Study Design.

Female C57BL/6 (B6.WT, H-2b, CD45.2), B6.S3L-Ptprca (PTPrca, H-2b, CD45.1) and B6D2F1 (H-2b/d, CD45.2) mice were purchased from the Animal Resource Center (Perth, WA, Australia). B6 Il27r$^{-/-}$ and Tbx2$^{-/-}$ mice were obtained from the Jackson Laboratory (Bar Harbor, Me., USA). B6 Blimp-1$^{GFP}$ (52), Il10$^{GFP}$×Foxp3$^{RFP}$ (19, 20), Foxp3$^{GFP}$, Foxp3$^{GFP-DTR}$, Il10$^{-/-}$, Ifnγ$^{-/-}$, MHC-II$^{-/-}$, Il10r$^{fl/fl}$×Lck-cre(53), Il10$^{fl/fl}$×Lck-cre(54), Prdm1$^{fl/fl}$×Lck-cre (Blimp-1$^{-/-}$)(51), CD11cDOG and DBA2× B6.CD11cDOG mice were bred at the QIMR Berghofer Medical Research Institute animal facility. B6 Eomes$^{fl/fl}$ mice were derived from the Eomes$^{floxed/mcherry}$ mice previously generated by GTB and described in (55). The Eomes$^{floxed/mcherry}$ mice were crossed to the B6.129S4-Gt (ROSA)26Sor$^{tm2(FLP*)Sor}$/J line which induces FLP-mediated recombination to remove the mCherry/Amp cassette to generate the Eomes$^{floxed}$ line. Removal of the Frt sites (and hence the IRES-Cherry cassette) was detected using primers (a) 5'-ggacttggggagccaaaa-3' (forward) and (b) 5'-catctgtaaccgcagcat-3' (reverse) (deleted allele, 306 bp). The primers (c) 5'-agtcggtttgagctggtgac-3' (forward), (d) 5'-tttggaacagcctccaaatc-3' (reverse) were used to detect the wild-type (339 bp) and foxed allele (421 bp) while primer (e) 5'-AAGGGGAAGGGTGGTTAGAA-3' (reverse) was used to detect the floxed allele (1941 bp) and germline deletion (587 bp). This Eomes$^{floxed}$ line was subsequently crossed with Cd4-cre or Lck-cre mice to generate T cell restricted Eomes$^{-/-}$ offspring. All recipient mice were used between 6 and 10 week of age and age matched female donor mice were used. Mice were housed in microisolator cages and received acidified autoclaved water (pH 2.5) after BMT. All animal studies were performed in accordance with the QIMR Berghofer Medical Research Institute Animal Ethics Committee. The inventors chose sample sizes based on estimates from initial and previously published results in order to ensure appropriate power. As stated in Figure legends and wherever possible, n values were derived from individual mice from replicated experiments.

Bone Marrow Transplantation.

BM (B6.CD45.1$^+$ or where indicated) was T cell depleted and splenocytes processed to CD3$^+$ or CD4$^+$ T cells as described previously (53). On day −1, recipient mice received 1100 cGy (B6D2F1), 1000 cGy (B6), 900 cGy (CD11c-DOG×DBA/2 F1) or otherwise specified doses of total body irradiation ([137Cs] source at 108 cGy/min), split into two doses separated by 3 h. On day 0, recipients were transplanted with 5-10×10$^6$ BM cells with or without 1-2× 10$^6$ T cells (CD3$^+$ or CD4$^+$). Intraperitoneal injections of rat-anti-mouse IFNγ (XMG1.2, produced in house, 1 mg/dose, 3 times per week), hamster-anti-mouse CD40L (MR1, BioXcell, 500 ug/dose, at, +2, +4, +6), rat-anti-mouse IL-6R (MR16-1, Chugai Pharmaceutical Co, Japan, 500 ug/dose, d−1, +3, +7) and control mAb were administered to recipients. In some experiments, CD11c-DOG mice (in which diphtheria toxin (DT) receptor is driven off the CD11c promoter) were used as BM donors. Recipients were given intraperitoneal injections of DT (160 ng/dose, 3 times per week) after BMT to deplete donor DC. For depletion of recipient DC, B6.CD11c-DOG×DBA/2 F1 mice were used as recipients and treated with DT on d−3, −1, 0, +1, +3, +5, +7.

$T_{reg}$ Depletion.

For depletion of $T_{reg}$, age-matched recipients (B6.WT or B6.Foxp3$^{GFP-DTR}$) were given intraperitoneal injections of DT (160 ng/dose, 3 times per week) for up to 2 weeks.

Histology.

GVHD target tissues (skin, liver and small intestine) were taken, preserved in 10% formalin, embedded in paraffin, processed to 5-mm-thick sections and H&E-stained. The sections were examined in a blinded fashion using a semi-quantitative scoring system and images acquired as previously described (56, 57).

Flow Cytometry.

Single cell suspensions were processed and stained, cells were analyzed on a LSR Fortessa cytometer (Beckman Dickinson) and data were processed using FlowJo Version 9.0 (TreeStar). Cell sorting was performed using a FACSAria or Moflo.

Clinical Analysis.

Peripheral blood was collected from healthy donors (n=27) or patients (d60 after BMT) of an observational study (n=18) and a phase III clinical trial (AC-TRN12614000266662) (n=25). All studies were approved by the institutional ethics committee and all subjects signed informed consent. Peripheral blood mononuclear cells (PBMC) were purified from whole blood using Ficoll-paque centrifugation and stained immediately.

Gene Expression Analysis.

Total RNA was extracted with the RNeasy Micro kit (Qiagen, Netherlands) and gene expression determined using TaqMan GE assays (Applied Biosystems, MA, USA). All measurements were run in parallel with the housekeeping gene Hprt. All primers/probe mixtures were purchased from Applied Biosystems.

Statistics.

Results from mouse experiments are presented as mean±SEM and the Mann-Whitney U test used for comparisons. Results from clinical samples are presented as median±interquartile range and Mann-Whitney U test used for comparisons. Survival is estimated and plotted using Kaplan-Meier methods, and the difference between subgroups is estimated using log-rank methods. Ordinary least squares method is used in the linear or semi-log regression analysis. A two-sided p value 0.05 is considered statistically significant. Statistical analyses are performed using Prism Version 6 software (GraphPad). NS=not significant, *P<0.05; P<0.01; *P<0.001; ****P<0.0001.

Lymphocyte Isolation from Small Intestine and Liver.

Small intestine were cut into 3-5 mm pieces, washed with PBS, incubated in Ca/Mg-free PBS containing EDTA (Chem-Supply, 5 mM) for 30 min at 37° C. with constant agitation. Cells were isolated by passing through 100 μm cell strainer and kept as fraction 1. The remaining sample was further treated with RPMI containing DNase (5 μg/mL) and Collagenase 4 (Sigma-Aldrich, 5 μg/mL) for 30 min at 37° C. and cells were isolated as fraction 2. Fraction 1 and 2 were combined and mononuclear cells isolated by Percoll density gradient centrifugation. After removal of gall bladder, liver was perfused with PBS, processed to single cell suspensions and mononuclear cells isolated by Percoll density gradient centrifugation (65).

In Vitro Suppression Assays.

$T_R1$, $T_{reg}$ and $T_{con}$ cells were FACS sorted on the basis of Il10$^{GFP}$ and Foxp3$^{RFP}$ from spleens d14 after BMT and in vitro suppression assays performed as previously described (64), with natural $T_{reg}$ cells from nave animals used as positive control. Percent of suppression is calculated as following: ((percent divided cells of $T_{con}$ alone−percent divided cells of $T_{con}$ with suppressors)/percent divided cells of $T_{con}$ alone)*100.

Analysis of GVHD Suppression.

B6D2F1 recipients were transplanted with FACS sorted CD4$^+$CD25$^{neg}$ T cells (B6.WT or and BM (Il10$^{-/-}$) and monitored for systemic GVHD as described before (64). When acute GVHD was established (d7 after BMT), $T_R1$ cells FACS sorted from spleens and liver of a concurrently performed BMT (d14) were infused to one group of recipients (1×10$^6$ per mouse), which were devoid of $T_R1$ cells (FIG. 1H).

Characterisation of Sorted $T_R1$ Cells.

B6D2F1 were transplanted with CD3$^+$ T cells (Il10$^{GFP}$ Foxp3$^{RFP}$) and spleens processed and sorted for $T_R1$, $T_{reg}$ and $T_{con}$ cells 14 days after BMT. Cells were stained for transcription factors immediately after sort and cytokines analysed by ICS. Sorted cells (10$^6$/mL) were stimulated in 96 well plates with PMA (50 ng/mL) and ionomycin (500 ng/mL) for 24 hours and cytokines in culture supernatant quantified using the BD Cytometric Bead Array system (BD Biosciences).

Intracellular Cytokine Staining.

Before intracellular cytokine staining (ICS) of T cells, single cell suspensions were stimulated for 4 hours with phorbol myristate acetate (PMA) (Sigma-Aldrich, 50 ng/mL) and ionomycin (Sigma-Aldrich, 500 ng/mL for murine cells, 1 μg/mL for PBMC) in the presence of brefeldin A (Biolegend). Before IL-27 staining, the cells were stimulated for 4 hours with lipopolysaccharide (Integrated Sciences, 1 ug/mL) in the presence of brefeldin A. The Live/Dead Fixable Dead Cell staining kit (Molecular Probes) was used to exclude dead cells. The cells were processed using the Foxp3/Transcription Factor Fixation/Permeabilization kit (eBiosciences) as per the manufacturer's instructions.

STAT Phosphorylation.

Spleens were processed to single cell suspensions, surface stained, followed by stimulation with rmIL-6 (100 ng/mL, eBioscience) or rmIL-27 (100 ng/mL, Biolegend) at 37 degrees for 5 or 15 minutes respectively, then processed with BD Phosflow kit (BD Biosciences) before FACS analysis.

mAbs Used in Mouse Experiments.

The following mAbs were purchased from Biolegend: CD44 Brilliant Violet (BV) 421 (IM7), CD62L Alexa Fluor (AF) 700 (MEL-14), CD49b AF647 (HMa2), Integrin α4β7 PE (DATK32), CD69 Pacific Blue (H1.2F3), CD279 (PD-1) PECY7 (RMPI-30), PD-L1 PE (10F.9G2), CXCR3 PE (CXCR3-173), GITR APC (YGITR765), DNAM-1 AF647 (TX42.1), CD223 (LAG3) PE (C9B7W), ICOS PE (7E.17G9), CD103 Pacific Blue (2E7), CD54 PE (3E2), CD11b PerCP/Cy5.5 (M1/70), Ly6C Pacific Blue (HK1.4), Ly6G APCCY7 (1A8), IA/IE FITC (M5/114.15.2), CD11c PE (N418), CD64 PECY7 (X54-5/7.1), F4/80 AF700 (BM8), IL-27 AF647 (MM27-7B1), IL-4 PE (11B11), IL-10 PE or APC (JES55-16E3), IL-2 PE (JES6-5H4), GM-CSF PE (MP1-22E9), IFNγ Pacific Blue (XMG1.2), IL-17A AF700 (TC11-8H10.1), FOXP3 AF647 (150D) or AF700 (FX-16s), T-bet AF647 or PE (4B10), Helios Pacific Blue (22F6). The following mAbs were purchased from BD Bioscience: CD25 PE (7D4), CD28 biotin (37.51), BCL-6 AF647 (K112-91), pSTAT3 (pY705) PE (4/P-STAT3) and pSTAT1 (pY701) PerCP/Cy5.5 (4a). The following mAbs were purchased from eBioscience: GARP PE (YG1C86), TIGIT efluor 660 (GIGD7), CD122 PerCP-eFluor 710 (Tm-β1), AhR (Aryl hydrocarbon receptor) PE (4MEJJ), GATA3 PE (TWAJ), RORγt PE (B2D) and Eomes PECY7 (Dan11mag). The following mAbs were purchased from R&D Systems: Neuropillin PE (761705), CCR2 APC (475301), anti-human TGF-β1 biotin (polyclonal) and Ki-67 PECY7 (B56). Anti-human Granzyme B (GB12) APC was purchased from Invitrogen.

mAbs Used for PBMC Staining.

The flowing mAbs were purchased from Biolegend: TCRαβ PerCP/CY5.5 (IP26), CD4 AF700 (RPA-T4), CD8 APCCY7 (SK1), CD25 PECY7 (BC96), CD197 BV421 (G043H7), CD45RA FITC (HI100), IL-4 BV421 (MP4-25D2), IFN-γ PECY7 (4S.B3), IL-10 PE (JES3-19F1), IL-17A BV605 (BL168), T-bet AF647 (4B10), FOXP3 PE or AF647 (150D) The flowing mAbs were purchased from BD Bioscience: CD3-Brilliant Blue 515 (UCHT2), CD3 V500 (UCHT2), CD45 V500 (HI30) and CD127 BV605 (HIL-7R-M21). The following mAbs were purchased from eBioscience: CD279 (PD-1) PE (12-2799-42) and Eomes PE-eFluor 610 (WD1928).

ChIP and Real-Time PCR Analysis.

Figure 3D:
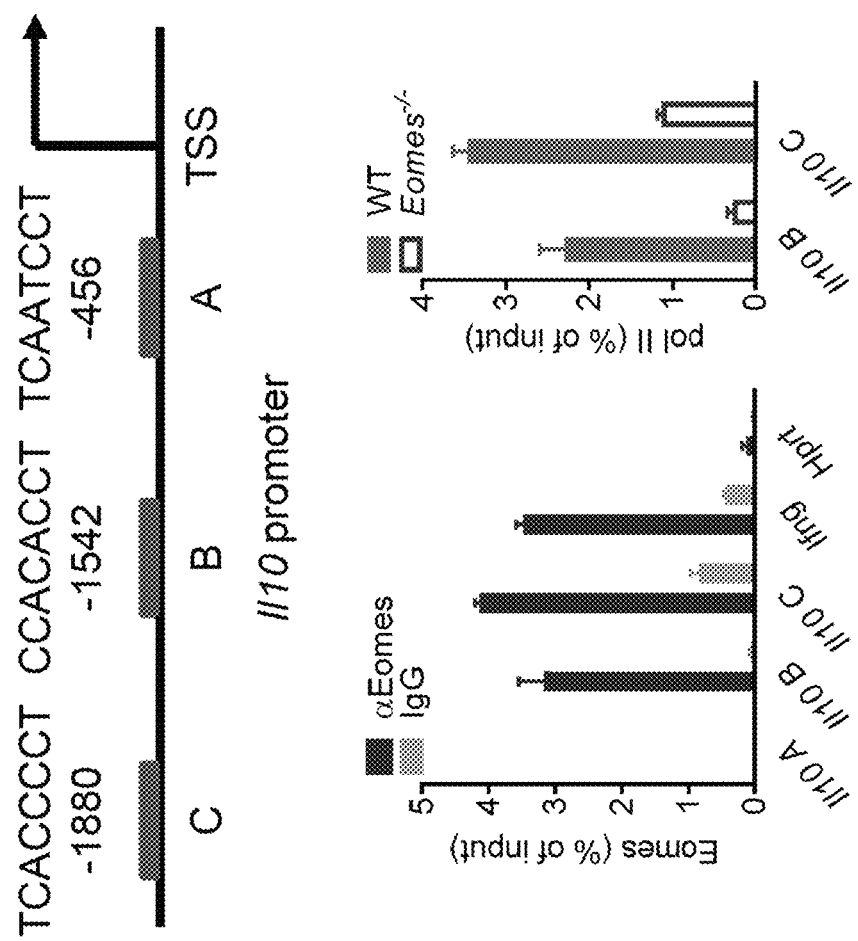

5-7×10$^6$ T$_R$1 cells (Il10$^{GFP+}$Foxp3$^{RFPneg}$) or CD4$^+$ T cells were fixed, lysed and then sonicated to yield 0.5 kb DNA fragments, and 1% of the chromatin preparation was set aside as the input fraction. The chromatin was then immunoprecipitated with anti-Eomes (ab23345, Abcam), anti-pol II (ab817, Abcam) and rabbit IgG (ab37415, Abcam). DNA were isolated using the PCR purification/Gel Extraction kit (QIAGEN) and the SYBR Green PCR Kit was used for real-time PCR detection of the immunoprecipitated targets. Primers (A-C) were designed to detect DNA sequences containing T-box conserved sites (TCACACCT) flanking 0-2 kb upstream of the transcription start site (TSS) of the Il10 promoter (FIG. 3D). The primer sets are listed in table S1. The data are presented as percent of immunoprecipitated target sequences relative to input chromatin.

T$_H$ Cell Polarization.

MACS purified CD4$^+$ T cells (>90% pure) were resuspended in IMDM (10$^6$ cells/mL) with 10% FBS, 2 mM L-glutamine, 50 mM 2-ME, 100 U/mL penicillin, and 100 mg/mL streptomycin sulfate, and stimulated with plate-bound CD3 (3 ug/mL) and CD28 (1 ug/mL) for 4 days. The following combinations of cytokines were added for the polarization of T$_H$1: rhIL-2 (100 U/mL), IL-12p70 (10 ng/mL) and anti-IL-4 (clone 11B11, 10 µg/mL); T$_H$2: rhIL-2 (100 U/mL), rmIL-4 (eBioscience, 40 ng/mL) and anti-IFNγ (clone XMG1.2, 10 ug/mL); T$_H$17: IL-6 (30 ng/mL), TGFβ1 (5 ng/mL), IL-23 (15 ng/mL), IL-113 (20 ng/mL), TNFα (20 ng/mL), anti-IL-2 (clone JES6-1A12, 10 µg/mL), anti-IL-4 (10 µg/mL) and anti-IFNγ (10 µg/mL); T$_R$1 cells: rmIL-27 (Biolegend, 50 ng/mL) and TGFβ (1 ng/mL); induced T$_{reg}$: rhIL-2 (100 U/mL), TGFβ1 (10 ng/mL), Rapamycin (100 ng/mL). Cells were collected for analysis between day 4 and 7.

Retrovirus Production and Retroviral Transduction.

Envelope expressing plasmid (EcoPak) and vectors (MSCV-IRES-GFP or MSCV-Eomes-IRES-GFP) were used to transiently transfect HEK293T cells in the presence of GeneJuice (Novagen), and viral supernatants stored in −80° C. Retrovirus was centrifuged onto RetroNectin (Takara, 32 µg/mL)-coated plates for 1 h at 3000 g at 4° C. CD4$^+$ T cells were stimulated with plate-bound CD3 (2C11, produced in house, 10 µg/mL) and CD28 (N3751, produced in house, 1 µg/mL) for 20-24 h before cultivating with the retrovirus in the presence of rhIL-2 (Aldesleukin, 100 U/mL) and Polybrene (Sigma-Aldrich, 16 µg/mL) for 4 h. Cells were then washed and cultured in the presence of rhIL-2 (100 U/mL) for 3-4 days, FACS sorted to GFP$^{hi}$ population and allowed for further expansion 1-2 days for subsequent experiments.

In Vitro Generation of Eomes Transduced T$_R$1 Cells.

Retrovirally transduced CD4$^+$ T cells were resuspended in IMDM (10$^6$ cells/mL) with 10% FBS, 2 mM L-glutamine, 50 mM 2-ME, 100 U/mL penicillin, and 100 mg/mL streptomycin sulfate, and stimulated with plate-bound CD3 (1 µg/mL) and CD28 (1 ug/mL) in the presence of rhIL-2 (50 U/mL) and rmIL-27 (50-100 ng/mL) for 20-24 h and then rested in culture with IL-2 and IL-27 as above for 4-5 days.

Experimental 2

IL-27 is a critical cytokine for the generation of T$_R$1 cells both in vivo and in vitro (59, 60) which functions through the induction of Eomes expression (59). The present inventors hypothesized that CD4$^+$ T cells in which Eomes expression is upregulated can be polarized to T$_R$1 cells in the absence of IL-27. Indeed, the expression of IL-10$^+$IFNγ$^+$ T$_R$1 cells in Eomes-RV transduced CD4$^+$ T cells becomes independent of IL-27 (FIG. 20). In contrast, IL-27 is still required for the induction of T$_R$1 cells in Empty-RV transduced cells (FIG. 20). In addition to the simplification of generating the T$_R$1 cells product, the removal of IL-27 from cell culture also avoids unwanted effects of this multifaceted cytokine.

Next, the presented inventors generated alloantigen specific T$_R$1 cells by expression of a recombinant Eomes coding sequence in CD4$^+$ T cells and stimulation of these cells with allogenic DC (allo-DC). Stimulation with allo-DC with or without concurrent use of soluble CD3 demonstrates similar efficiency of retroviral transduction compared to stimulation with plate bound CD3 and CD28 (FIG. 21). Retrovirally transduced CD4+ T cells will be FACS sorted to GFP$^{hi}$ cells and polarized to T$_R$1 cells.

Materials and Methods

Retrovirus Production.

Retrovirus production was performed as described before (59).

Retroviral Transduction.

Empty or Eomes expressing Retrovirus (RV) was centrifuged onto RetroNectin (Takara, 32 µg/mL)-coated non-tissue culture treated plates for 1 h at 3000 g at 4° C. B6.WT CD4+ T cells (purified with MACS selection) were stimulated with plate-bound CD3 (2C11, produced in house, 2.5-10 µg/mL) and CD28 (N3751, produced in house, 0.5-1 ug/mL) for 20-24 hours, with allogenic dendritic cells (allo-DC, CD11c+MHCII+, MACS purified from spleens of B6D2F1 mice) and soluble CD3 (1 µg/mL) for 20-24 hours, or with allo-DC only for 48 hours before cultivating with the retrovirus in the presence of rhIL-2 (Aldesleukin, 100 U/mL) for 4-6 h. Cells were then washed and cultured in the presence of rhIL-2 (100 U/mL) for 3-4 days, FACS sorted to GFP$^{hi}$ population and allowed for further expansion 1-2 days for in vitro generation of T$_R$1 populations.

Flow Cytometry.

Surface staining, intracellular cytokine staining, and flow cytometric analysis were performed as described before (59).

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

1. M. G. Roncarolo et al., Interleukin-10-secreting type 1 regulatory T cells in rodents and humans. *Immunological reviews* 212, 28-50 (2006).
2. R. Bacchetta et al., High levels of interleukin 10 production in vivo are associated with tolerance in SCID patients transplanted with HLA mismatched hematopoietic stem cells. *The Journal of experimental medicine* 179, 493-502 (1994).
3. S. Gregori, K. S. Goudy, M. G. Roncarolo, The cellular and molecular mechanisms of immuno-suppression by human type 1 regulatory T cells. *Frontiers in immunology* 3, 30 (2012).
4. H. Groux et al., A CD4+ T-cell subset inhibits antigen-specific T-cell responses and prevents colitis. *Nature* 389, 737-742 (1997).
5. C. Pot, L. Apetoh, V. K. Kuchroo, Type 1 regulatory T cells (Tr1) in autoimmunity. *Seminars in immunology* 23, 202-208 (2011).
6. C. Neumann et al., Role of Blimp-1 in programming Th effector cells into IL-10 producers. *The Journal of experimental medicine* 211, 1807-1819 (2014).
7. M. Montes de Oca et al., Blimp-1-Dependent IL-10 Production by Tr1 Cells Regulates TNF-Mediated Tissue Pathology. *PLoS pathogens* 12, e1005398 (2016).
8. C. Heinemann et al., IL-27 and IL-12 oppose pro-inflammatory IL-23 in CD4+ T cells by inducing Blimp1. *Nature communications* 5, 3770 (2014).
9. N. Gagliani et al., Coexpression of CD49b and LAG-3 identifies human and mouse T regulatory type 1 cells. *Nature medicine* 19, 739-746 (2013).
10. L. Apetoh et al., The aryl hydrocarbon receptor interacts with c-Maf to promote the differentiation of type 1 regulatory T cells induced by IL-27. *Nature immunology* 11, 854-861 (2010).
11. A. Vasanthakumar, A. Kallies, IL-27 paves different roads to Tr1. *European journal of immunology* 43, 882-885 (2013).
12. A. Awasthi et al., A dominant function for interleukin 27 in generating interleukin 10-producing anti-inflammatory T cells. *Nature immunology* 8, 1380-1389 (2007).
13. A. Cope, G. Le Friec, J. Cardone, C. Kemper, The Th1 life cycle: molecular control of IFN-gamma to IL-10 switching. *Trends in immunology* 32, 278-286 (2011).
14. J. L. Ferrara, J. E. Levine, P. Reddy, E. Holler, Graft-versus-host disease. *Lancet* 373, 1550-1561 (2009).
15. B. R. Blazar, W. J. Murphy, M. Abedi, Advances in graft-versus-host disease biology and therapy. *Nature reviews. Immunology* 12, 443-458 (2012).
16. K. Matsuoka et al., Altered regulatory T cell homeostasis in patients with CD4+ lymphopenia following allogeneic hematopoietic stem cell transplantation. *The Journal of clinical investigation* 120, 1479-1493 (2010).
17. B. R. Blazar et al., Interleukin-10 dose-dependent regulation of CD4+ and CD8+ T cell-mediated graft-versus-host disease. *Transplantation* 66, 1220-1229 (1998).
18. E. S. Morris et al., Donor treatment with pegylated G-CSF augments the generation of IL-10-producing regulatory T cells and promotes transplantation tolerance. *Blood* 103, 3573-3581 (2004).
19. M. Kamanaka et al., Expression of interleukin-10 in intestinal lymphocytes detected by an interleukin-10 reporter knockin tiger mouse. *Immunity* 25, 941-952 (2006).
20. Y. Y. Wan, R. A. Flavell, Identifying Foxp3-expressing suppressor T cells with a bicistronic reporter. *Proceedings of the National Academy of Sciences of the United States of America* 102, 5126-5131 (2005).
21. E. Cretney et al., The transcription factors Blimp-1 and IRF4 jointly control the differentiation and function of effector regulatory T cells. *Nature immunology* 12, 304-311 (2011).
22. L. Gabrysova et al., Negative feedback control of the autoimmune response through antigen-induced differentiation of IL-10-secreting Th1 cells. *The Journal of experimental medicine* 206, 1755-1767 (2009).
23. F. J. Quintana et al., Control of T(reg) and T(H)17 cell differentiation by the aryl hydrocarbon receptor. *Nature* 453, 65-71 (2008).
24. I. D. Mascanfroni et al., Metabolic control of type 1 regulatory T cell differentiation by AHR and HIF1-alpha. *Nature medicine* 21, 638-646 (2015).
25. E. Zigmond et al., Macrophage-restricted interleukin-10 receptor deficiency, but not IL-10 deficiency, causes severe spontaneous colitis. *Immunity* 40, 720-733 (2014).

26. G. R. Hill et al., Total body irradiation and acute graft-versus-host disease: the role of gastrointestinal damage and inflammatory cytokines. *Blood* 90, 3204-3213 (1997).
27. K. A. Markey, K. P. MacDonald, G. R. Hill, The biology of graft-versus-host disease: experimental systems instructing clinical practice. *Blood* 124, 354-362 (2014).
28. J. S. Stumhofer et al., A role for IL-27p28 as an antagonist of gp130-mediated signaling. *Nature immunology* 11, 1119-1126 (2010).
29. J. M. Kim, J. P. Rasmussen, A. Y. Rudensky, Regulatory T cells prevent catastrophic autoimmunity throughout the lifespan of mice. *Nature immunology* 13, 191-197 (2007).
30. A. McNally, G. R. Hill, T. Sparwasser, R. Thomas, R. J. Steptoe, CD4+CD25+ regulatory T cells control CD8+ T-cell effector differentiation by modulating IL-2 homeostasis. *Proceedings of the National Academy of Sciences of the United States of America* 108, 7529-7534 (2011).
31. K. Lahl et al., Selective depletion of Foxp3+ regulatory T cells induces a scurfy-like disease. *The Journal of experimental medicine* 204, 57-63 (2007).
32. H. M. Shin et al., Epigenetic modifications induced by Blimp-1 Regulate CD8(+) T cell memory progression during acute virus infection. *Immunity* 39, 661-675 (2013).
33. A. O'Garra, P. Vieira, T(H)1 cells control themselves by producing interleukin-10. *Nature reviews. Immunology* 7, 425-428 (2007).
34. S. M. Gordon et al., The transcription factors T-bet and Eomes control key checkpoints of natural killer cell maturation. *Immunity* 36, 55-67 (2012).
35. A. M. Intlekofer et al., Effector and memory CD8+ T cell fate coupled by T-bet and eomesodermin. *Nature immunology* 6, 1236-1244 (2005).
36. B. J. Raveney et al., Eomesodermin-expressing T-helper cells are essential for chronic neuroinflammation. *Nature communications* 6, 8437 (2015).
37. M. A. Curran et al., Systemic 4-1BB activation induces a novel T cell phenotype driven by high expression of Eomesodermin. *The Journal of experimental medicine* 210, 743-755 (2013).
38. E. Lupar et al., Eomesodermin Expression in CD4+ T Cells Restricts Peripheral Foxp3 Induction. *Journal of immunology* 195, 4742-4752 (2015).
39. K. Ichiyama et al., Transcription factor Smad-independent T helper 17 cell induction by transforming-growth factor-beta is mediated by suppression of eomesodermin. *Immunity* 34, 741-754 (2011).
40. N. Gagliani et al., Th17 cells transdifferentiate into regulatory T cells during resolution of inflammation. *Nature* 523, 221-225 (2015).
41. P. P. Ahern et al., Interleukin-23 drives intestinal inflammation through direct activity on T cells. *Immunity* 33, 279-288 (2010).
42. M. J. McGeachy et al., TGF-beta and IL-6 drive the production of IL-17 and IL-10 by T cells and restrain T(H)-17 cell-mediated pathology. *Nature immunalogy* 8, 1390-1397 (2007).
43. D. Jankovic, D. G. Kugler, A. Sher, IL-10 production by CD4+ effector T cells: a mechanism for self-regulation. *Mucosal immunology* 3, 239-246 (2010).
44. M. Batten et al, Interleukin 27 limits autoimmune encephalomyelitis by suppressing the development of interleukin 17-producing T cells. *Nature immunology* 7, 929-936 (2006).
45. L. Belle et al., Blockade of interleukin 27 signaling reduces GVHD in mice by augmenting Treg reconstitution and stabilizing FOXP3 expression. *Blood*, (2016).
46. G. A. Kennedy et al., Addition of interleukin-6 inhibition with tocilizumab to standard graft-versus-host disease prophylaxis after allogeneic stem-cell transplantation: a phase ½ trial. *The Lancet. Oncology* 15, 1451-1459 (2014).
47. V. Lazarevic, L. H. Glimcher, G. M. Lord, T-bet: a bridge between innate and adaptive immunity. *Nature reviews. Immunology* 13, 777-789 (2013).
48. F. Cruz-Guilloty et al., Runx3 and T-box proteins cooperate to establish the transcriptional program of effector CTLs. *The Journal of experimental medicine* 206, 51-59 (2009).
49. Y. Iwasaki et al., Egr-2 transcription factor is required for Blimp-1-mediated IL-10 production in IL-27-stimulated CD4$^+$ T cells. *European journal of immunology* 43, 1063-1073 (2013).
50. A. Xin et al., A molecular threshold for effector CD8(+) T cell differentiation controlled by transcription factors Blimp-1 and T-bet. *Nature immunology* 17, 422-432 (2016).
51. A. Kallies, A. Xin, G. T. Belz, S. L. Nutt, Blimp-1 transcription factor is required for the differentiation of effector CD8(+) T cells and memory responses. *Immunity* 31, 283-295 (2009).
52. A. Kallies et al., Plasma cell ontogeny defined by quantitative changes in blimp-1 expression. *The Journal of experimental medicine* 200, 967-977 (2004).
53. M. C. Pils et al., Monocytes/macrophages and/or neutrophils are the target of IL-10 in the LPS endotoxemia model. *European journal of immunology* 40, 443-448 (2010).
54. A. Roers et al., T cell-specific inactivation of the interleukin 10 gene in mice results in enhanced T cell responses but normal innate responses to lipopolysaccharide or skin irritation. *The Journal of experimental medicine* 200, 1289-1297 (2004).
55. E. E. Kara et al, CCR2 defines in vivo development and homing of IL-23-driven GM-CSF-producing Th17 cells. *Nature communications* 6, 8644 (2015).
56. P. Zhang et al., Induced regulatory T cells promote tolerance when stabilized by rapamycin and IL-2 in vivo. *Journal of immunology* 191, 5291-5303 (2013).
57. A. C. Burman et al., IFNgamma differentially controls the development of idiopathic pneumonia syndrome and GVHD of the gastrointestinal tract. *Blood* 110, 1064-1072 (2007).
58. M. Koyama et al., Donor colonic CD103+ dendritic cells determine the severity of acute graft-versus-host disease. *J Exp Med* 212, 1303-1321 (2015).
59. P. Zhang et al. Eomesodermin promotes the development of type 1 regulatory T ($T_R$1) cells. *Sci Immunol* 2017; 2(10). doi: 10.1126/sciimmunol.aah7152
60. A. Vasanthakumar et al. IL-27 paves different roads to Tr1. *European journal of immunology* 2013; 43(4): 882-885. doi: 10.1002/eji.201343479

What is claimed is:

1. A method of producing a population of immunosuppressive regulatory T cells, the method comprising: isolating a heterogenous population of cells comprising regulatory T cells; enriching for IL-10$^+$ CD4$^+$ T cells that are optionally positive or high for at least one of CD122, α4β7, LAG-3, Ly6C and TIGIT, and/or optionally negative or low for one or more of CD25, CD69 and FoxP3; and introducing into the IL-10$^+$ CD4$^+$ T cells a construct comprising an Eomes coding sequence in operable connection with a regulatory sequence that is operable in the IL-10$^+$ CD4$^+$ T cells, to thereby produce a population of immunosuppressive regulatory T cells comprising Eomes$^+$IL-10$^+$ CD4$^+$ T cells.

2. The method claim 1, further comprising expanding the Eomes$^+$IL-10$^+$ CD4$^+$ T cells.

3. The method of claim 2, wherein the Eomes$^+$IL-10$^+$ CD4$^+$ T cells are expanded by a process comprising contacting the Eomes$^+$IL-10$^+$ CD4$^+$ T cells with an agent selected from the group consisting of an antigen, an alloantigen, an anti-CD3 antibody and an anti-CD28 antibody.

4. The method of claim 2, wherein the Eomes$^+$IL-10$^+$ CD4$^+$ T cells comprise Eomes$^+$IL-10$^+$ CD4$^+$ T cells that are antigen-specific.

5. The method of claim 1, wherein the Eomes$^+$IL-10$^+$ CD4$^+$ T cells comprise Eomes$^{hi}$ T cells.

6. The method of claim 1, wherein the Eomes$^+$IL-10$^+$ CD4$^+$ T cells comprise Tbet$^{lo}$ T cells.

7. The method of claim 1, wherein the Eomes$^+$IL-10$^+$ CD4$^+$ T cells comprise IFNγ$^+$ T cells.

8. The method of claim 1, wherein the Eomes$^+$IL-10$^+$ CD4$^+$ T cells are high for one or both of IL-10 and IFNγ.

9. The method of claim 1, wherein the Eomes$^+$IL-10$^+$ CD4$^+$ T cells are negative or low for $T_H2$ cytokines.

10. The method of claim 1, wherein the Eomes$^+$IL-10$^+$ CD4$^+$ T cells are capable of suppressing at least one immune function selected from the group consisting of IL-2 production, cell proliferation, cytokine production, cell migration, and effector functions, killing, and T-cell proliferation.

11. A method of eliciting immune tolerance in a subject, the method comprising preparing a population of immunosuppressive regulatory T cells produced according to the method of claim 1 and administering the immunosuppressive regulatory T cells to the subject to thereby suppress an immune response in the subject.

12. The method of claim 11, wherein the population of immunosuppressive regulatory T cells is autologous or allogeneic to the subject.

13. The method of claim 11, wherein the subject has an immune or autoimmune disorder.

* * * * *

UNITED STATES PATENT AND TRADEMARK OFFICE
CERTIFICATE OF CORRECTION

| | | |
|---|---|---|
| PATENT NO. | : 11,662,343 B2 | |
| APPLICATION NO. | : 16/603454 | |
| DATED | : May 30, 2023 | |
| INVENTOR(S) | : Hill et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 662 days.

Signed and Sealed this
Twelfth Day of November, 2024

*Katherine Kelly Vidal*

Katherine Kelly Vidal
*Director of the United States Patent and Trademark Office*